(12) United States Patent
Giese et al.

(10) Patent No.: US 10,071,966 B2
(45) Date of Patent: Sep. 11, 2018

(54) DRUG FOR INHIBITING AGGREGATION OF PROTEINS INVOLVED IN DISEASES LINKED TO PROTEIN AGGREGATION AND/OR NEURODEGENERATIVE DISEASES

(71) Applicants: Ludwig-Maximilians-Universität München, München (DE); Max-Planck-Gesellschaft zur Förderung der Wissenschaften e.V., München (DE)

(72) Inventors: Armin Giese, München (DE); Uwe Bertsch, Scheuring (DE); Hans Kretzschmar, Hohenschäftlarn (DE); Matthias Habeck, München (DE); Thomas Hirschberger, Stuttgart (DE); Paul Tavan, München (DE); Christian Griesinger, Göttingen (DE); Andrei Leonov, Göttingen (DE); Sergey Ryazanov, Göttingen (DE); Petra Frick, München (DE); Markus Geissen, Buchholz i.d. Nordheide (DE); Martin H. Groschup, Weitenhagen (DE); Jens Wagner, München (DE)

(73) Assignees: LUDWIG-MAXIMALIANS-UNIVERSITAT MUNCHEN, Munich (DE); MAX-PLANCK-GESELLSCHAFT ZUR FORDERUNG DER WISSENSCHAFTEN E.V., Munich (DE)

(*) Notice: Subject to any disclaimer, the term of this patent is extended or adjusted under 35 U.S.C. 154(b) by 0 days.

(21) Appl. No.: 14/978,964

(22) Filed: Dec. 22, 2015

(65) Prior Publication Data
US 2016/0185730 A1 Jun. 30, 2016

Related U.S. Application Data

(63) Continuation of application No. 12/996,833, filed as application No. PCT/EP2009/004144 on Jun. 9, 2009.

(30) Foreign Application Priority Data

Jun. 9, 2008 (EP) .................................. 08010458

(51) Int. Cl.
| | |
|---|---|
| C07D 231/12 | (2006.01) |
| A61K 31/4155 | (2006.01) |
| A61K 31/4164 | (2006.01) |
| A61K 31/42 | (2006.01) |
| A61K 31/4245 | (2006.01) |
| G01N 33/68 | (2006.01) |
| A61K 31/40 | (2006.01) |
| A61K 31/415 | (2006.01) |
| C07D 207/333 | (2006.01) |
| C07D 405/04 | (2006.01) |

(Continued)

(52) U.S. Cl.
CPC ............ *C07D 231/12* (2013.01); *A61K 31/40* (2013.01); *A61K 31/415* (2013.01); *A61K 31/4155* (2013.01); *A61K 31/4164* (2013.01); *A61K 31/42* (2013.01); *A61K 31/4245* (2013.01); *C07D 207/333* (2013.01); *C07D 231/06* (2013.01); *C07D 233/64* (2013.01); *C07D 261/08* (2013.01); *C07D 271/06* (2013.01); *C07D 405/04* (2013.01); *C07D 413/04* (2013.01); *G01N 33/6896* (2013.01); *G01N 2800/2828* (2013.01)

(58) Field of Classification Search
CPC ........................ C07D 231/12; C07D 207/333; C07D 405/04; C07D 271/06; C07D 261/08; C07D 233/64; C07D 413/04; C07D 231/06; A61K 31/4155; A61K 31/4164; A61K 31/42; A61K 31/4245; A61K 31/40; A61K 31/415; G01N 33/6896; G01N 2800/2828
See application file for complete search history.

(56) References Cited

U.S. PATENT DOCUMENTS

| | | | |
|---|---|---|---|
| 3,257,203 | A | 6/1966 | Sus et al. |
| 7,220,745 | B2 | 5/2007 | Singh et al. |

(Continued)

FOREIGN PATENT DOCUMENTS

| | | |
|---|---|---|
| CH | 426848 | 12/1966 |
| EP | 1 719 767 A1 | 11/2006 |

(Continued)

OTHER PUBLICATIONS

Glabe, C.G.,"Common mechanisms of amyloid oligomer pathogenesis in degenerative disease." Neurobiology of aging 27.4 (2006): 570-575.*

(Continued)

*Primary Examiner* — John M Mauro
(74) *Attorney, Agent, or Firm* — Foley & Lardner LLP

(57) ABSTRACT

The present invention relates to a compound represented by formula (E). The present invention also relates to a compound represented by the formula (E) for use in the treatment or prevention of diseases linked to protein aggregation and/or neurodegenerative diseases. Moreover, the present invention relates to pharmaceutical and diagnostic compositions comprising the compound of the invention as well as to a kit. Furthermore, the present invention relates to a method of imaging deposits of aggregated protein. A kit for preparing a detectably labelled compound of the present invention is also disclosed.

13 Claims, 32 Drawing Sheets

(51) Int. Cl.
  *C07D 271/06*  (2006.01)
  *C07D 261/08*  (2006.01)
  *C07D 233/64*  (2006.01)
  *C07D 413/04*  (2006.01)
  *C07D 231/06*  (2006.01)

(56) References Cited

U.S. PATENT DOCUMENTS

| | | | |
|---|---|---|---|
| 2004/0019113 | A1 | 1/2004 | Jozefiak et al. |
| 2005/0271584 | A1 | 12/2005 | Kung et al. |
| 2006/0183790 | A1 | 8/2006 | Cole et al. |
| 2007/0197532 | A1 | 8/2007 | Cao et al. |
| 2009/0111863 | A1* | 4/2009 | Esposito ............ C07C 37/16 514/383 |

FOREIGN PATENT DOCUMENTS

| | | |
|---|---|---|
| FR | 2104932 | 4/1972 |
| JP | 04-124178 A | 4/1992 |
| JP | 04-124178 A | 4/1992 |
| JP | 2009-203166 A | 9/2009 |
| WO | WO-02/16333 A2 | 2/2002 |
| WO | WO-03/057225 A2 | 7/2003 |
| WO | WO-03/079973 A2 | 10/2003 |
| WO | WO-03/093252 A1 | 11/2003 |
| WO | WO-2004/080972 A1 | 9/2004 |
| WO | WO-2006/109680 A1 | 4/2005 |
| WO | WO-2005/097759 A1 | 10/2005 |
| WO | WO-2007/061923 A2 | 5/2007 |
| WO | WO-2007/063946 A1 | 6/2007 |
| WO | WO-2007/149395 A2 | 12/2007 |
| WO | WO-2008/131148 A1 | 10/2008 |
| WO | WO 2009/146343 A1 | 12/2009 |
| WO | WO-2009/146343 A1 | 12/2009 |
| WO | WO-2009/151529 | 12/2009 |

OTHER PUBLICATIONS

Database Registry [Online] Retrieved from STN, Sep. 21, 2006, Searched on Oct. 18, 2016, CAS Registry No. 908083-75-0.

Database Registry [Online] Retrieved from STN, Oct. 22, 2001, Searched on Oct. 18, 2016, CAS Registry No. 363614-19-1, 363614-18-0, 363614-17-9, 363614-16-8, 363614-15-7, 363614-14-6, 363613-84-7, 363613-83-6, 363613-82-5, 363613-81-4.

Database Registry [Online] Retrieved from STN, Oct. 15, 2001, Searched on Oct. 18, 2016, CAS Registry No. 362019-99-6, 362019-96-3, 362019-90-7, 362019-90-7, 362019-86-1, 362019-83-8, 362019-82-7, 362019-79-2, 362019-76-9, 362019-65-6, 362019-58-7, 362019-55-4, 362019-50-9, 362019-44-1, 362019-38-3, 362019-32-7, 362019-30-5, 362019-28-1, 362019-25-8, 362019-21-4, 362019-17-8, 362019-13-4, 362019-09-8, 362019-05-4, 362019-01-0, 362018-97-1, 362018-93-7, 362018-89-1, 362018-87-9, 362018-85-7, 362018-83-5, 362018-81-3, 362018-79-9, 362018-77-7.

Database Registry [Online] Retrieved from STN, Oct. 12, 2001, Searched on Oct. 18, 2016, CAS Registry No. 361573-57-1, 361573-56-0, 361573-55-9, 361573-54-8, 361573-53-7, 361573-52-6, 361573-51-5, 361573-49-1, 361573-47-9, 361573-46-8, 361573-44-6, 361573-43-5, 361573-42-4, 361573-41-3, 361573-40-2, 361573-39-9, 361573-38-8, 361573-37-7, 361573-36-6, 361573-35-5, 361573-34-4, 361573-33-3, 361573-32-2, 361573-31-1, 361573-30-0, 361573-29-7, 361573-28-6, 361573-27-5, 361570-52-7, 361570-50-5, 361570-46-9, 361570-44-7, 361570-42-5, 361570-34-5, 361570-28-7, 361570-26-5, 361570-24-3, 361570-20-9, 361570-18-5, 361570-16-3, 361570-14-1, 361570-12-9, 361570-10-7, 361570-07-2, 361570-05-0, 361570-03-8, 361570-01-6, 361569-99-5, 361569-97-3, 361569-95-1, 361569-93-9, 361569-91-7, 361569-89-3, 361569-87-1.

Japan Patent Office, Notification of Reasons for Rejection issued in Application No. JP 2015-245186 dated Nov. 18, 2016.

Japan Patent Office, Notification of Reasons for Rejection issued in Application No. JP 2015-245187 dated Nov. 8, 2016.

Bendor, "The function of α-synuclein." Neuron, 2013; 1044-1066, 79.6.

Chandra, R. et al., "Design synthesis, and structure—activity relationship of novel thiophene derivatives for beta-amyloid plaque imaging," Bioorganic & Medicinal Chemistry Letters, vol. 16, No. 5, Mar. 1, 2006, pp. 1350-1352.

Chauhan, et al., "Solid phase synthesis of novel pryazole derivatives from diaryl 1.3-diketones under microwave irradiation", J. Indian Chem. Soc., vol. 82, 2005, pp. 1016-1018.

Communication Pursuant to Article 94(3) EPC dated Nov. 11, 2014 issued in European Application No. 09 772 072.6.

Communication pursuant to Article 94(3) EPC in EP Appln No. 13 176 577.8 dated Feb. 5, 2015.

Creutzfeldt-Jakob disease prevention—Mayo Clinic; accessed online May 11, 2015: http://www.mayoclinic.org/diseases-conditions/creutzfeldt-jakob-disease/basics/prevention/con-20028005?p=1, p. 1-7

Database Pubchem [Online] NCBI—2-(3,4-dmethoxyphenyl)-5-(3-fluorophenyl)-1,3,4-oxadiazole—Compound S, (Database Accession No. CID755411) Jul. 8, 2005, 6 pgs.

Database PubChem Chemistry [Online] NCBI; Jun. 4, 2005, Database accession No. CID 655985.

Database PubChem Chemistry [Online] NCBI; Mar. 27, 2005, Database accession No. CID 402002.

Database Pubchem Compound [Online] dated Jul. 31, 2007, ST50758437, Database Accession No. CID 16456861, 3 pages.

Database Pubchem Chemistry [Online] dated Jul. 8, 2005, 2-(1,3-benzodioxol-5-yl)-5-(3-chlorophenyl)-1,3,4-oxadiazole, Database Accession No. CID 694690, 5 pages.

Database Pubchem Compound [Online] dated Jul. 9, 2005, ST50928263, Database Accession No. CID 781488, 5 pages.

Database Pubchem Compound [Online] dated Mar. 27, 2005, 3-(1,3-benzodioxol-5-yl)-5-(2,4-dichloro-5-fluorophenyl)-1H-pyrazole, Database Accession No. CID 402001, 4 pages.

Database Pubchem Compound [Online] dated Nov. 13, 2007, AGN-PC-016U0A, Database Accession No. CID 16824686, 4 pages.

Database Pubchem Compound [Online] dated Nov. 30, 2005, 3-(1,3-benzodioxol-5-yl)-5-(3-fluorophenyl)-1,2,4-oxadiazole, Database Accession No. CID 5303514, 4 pages.

Database Pubchem Compounds [Online] NCBI; Mar. 27, 2005, Database accession No. CID402000.

Database Pubchem Substance [Online] NCBI; dated Mar. 26, 2005, Database accession No. SID533159; 7 pages.

Database Pubchem Substance [Online] NCBI; Jul. 29, 2005 (Jul. 29, 2005), Database accession No. SID3703064; 6 pages.

Database Pubchem Substance [Online] NCBI; Nov. 30, 2005, Database accession No. SID7960351; 5 pages.

European Office Action received in the related European Patent Application No. EP 09772072.6, dated Feb. 12, 2013.

European Patent Office; Communication pursuant to Article 94(3) EPC on application 09 772 072.6 dated Sep. 3, 2015; 8 pages.

European Search Report dated Jan. 2, 2014 in European Application No. 13176577.8, 9 pgs.

Fearnley, "Ageing and Parkinson's disease: substantia nigra regional selectivity." Brain, 1991; 2283-2301, 114.5.

Ghaemmaghami, "Successes and Challenges in Phenotype-Based Lead Discovery for Prion Diseases: Miniperspective." Journal of medicinal chemistry, 2014; 6919-6929, 57.16.

Golde, "Thinking laterally about neurodegenerative proteinopathies." The Journal of clinical investigation, 2013; 1847-1855, 123.5.

Jellinger, "The Role of α-Synuclein in Neurodegeneration—an Update." Translational Neuroscience, 2012; 75-122, 3(2).

Kostka, "Single particle characterization of iron-induced pore-forming α-synuclein oligomers." Journal of Biological Chemistry, 2008; 10992-11003, 283.16.

Manna, F. et al., "Anti-inflammatory, analgesic and antipyretic N-acetyl- 2-pyrazolines and dihydrothienocoumarines," European Journal of Medicinal Chemistry, 1992, vol. 27, No. 6, pp. 633-639.

Meredith, "MPTP mouse models of Parkinson's disease: an update." Journal of Parkinson's disease, 2011; 19-33, 1.1.

(56) References Cited

OTHER PUBLICATIONS

NCBI Protein Database 2015; accessed online May 11, 2015; http://www.ncbi.nlm.nih.gov/protein/?term=(amyloid%20precursor%20and%20(homo%; p. 1-2.
Notification of Reasons for Rejection dated Nov. 18, 2013 in Japan Appliation No. 2011-512038, 4 pgs.
Office Action received in the related Chilean Application No. CL 1369-2010, dated Jan. 15, 2013.
Ono, Masahiro et al., "Development of novel beta-amyloid probes based on 3,5-diphenyl-1,2,4-oxadiazole," Bioorganic & Medicinal Chemistry, vol. 16, No. 14, Jul. 15, 2008, pp. 6867-6872.
Restrepo, "Feasibility of an early Alzheimer's disease immunosignature diagnostic test." Journal of neuroimmunology, 2013; 154-160, 254.1.
Stedmans's Online Medical Dictionary 2015, accessed May 12, 2015; http://www.stedmansonline.com/popup.aspx?aid=5230247; p. 1.
Stella, "Prodrugs." Drugs, 1985; 455-473, 29.5.
UBHI, "Multiple system atrophy: a clinical and neuropathological perspective." Trends in neurosciences, 2011; 581-590, 34.11.
Vekrellis, "Targeting intracellular and extracellular alpha-synuclein as a therapeutic strategy in Parkinson's disease and other syncleinopathies." Expert opinion on therapeutic targets, 2012; 421-432, 16.4.
Wagner, "Anle138b: a novel oligomer modulator for disease-modifying therapy of neurodegenerative diseases such as prion and Parkinson's disease." Acta neuropathological, 2013; 795-813, 125. 6.
WebMD, Prevention of Parkinson's Disease, http://www.webmd.com/parkinsons-disease/guide/parkinsons-disease-prevention, p. 1-4; accessed online Jun. 18, 2014.
Database PubChem Assay [Online] NCBI; Aug. 15, 2004, Database accession No. AID119.
Database PubChem Chemistry [Online] NCBI; Aug. 15, 2004, Database accession No. CID 402002.
European Office Action issued in corresponding application No. 13 176 577 dated Jan. 14, 2016.
Examination Report issued in corresponding Indian application No. 6419/CHENP/2010 dated Mar. 14, 2017.

\* cited by examiner

A)

DPP_1 substance_id: 30142_H04
tp3_reduktion: 1.0
tp3_reduktion_mue: 0.5
tp3_scn2a: 1.0 substance_id: 30136_B06
tp1_sift: 0.318
tp3_reduktion: 1.0
tp3_reduktion_mue: 0.0
tp3_scn2a: 1.0 substance_id: 30131_A02
tp1_sift: -0.341
tp3_reduktion: 0.0
tp3_scn2a: 0.0 substance_id: 30143_D02
tp1_sift: -0.685
tp3_reduktion: 0.0
tp3_scn2a: 0.0

B)

DPP_2 substance_id: 30131_C10
tp1_sift: 0.049
tp3_reduktion: 1.0
tp3_reduktion_mue: 1.0
tp3_scn2a: 0.5 substance_id: 30139_H04
tp1_sift: -0.809
tp3_reduktion: 1.0
tp3_reduktion_mue: 1.0
tp3_scn2a: 1.0 substance_id: 30142_E08
tp1_sift: 0.304
tp3_reduktion: 1.0
tp3_reduktion_mue: 1.0
tp3_scn2a: 0.5 substance_id: 30139_E02
tp1_sift: 0.067
tp3_reduktion: 1.0
tp3_reduktion_mue: 0.5
tp3_scn2a: 1.0

C)

substance_id: 10353_F11
tp1_sift: 1.039
tp1_sift_validation: -1.0
tp3_reduktion: 1.0
tp3_reduktion_mue: 1.0
tp3_scn2a: 1.0 substance_id: 30134_F02
tp1_sift: -0.587
tp3_reduktion: 1.0
tp3_reduktion_mue: 0.5
tp3_scn2a: 0.5 substance_id: 10353_B07
tp3_reduktion: 0.0 substance_id: 10353_C08
tp1_sift: 0.964
tp3_reduktion: 0.0 substance_id: 30135_G10
tp1_sift: 0.505
tp3_reduktion: 1.0
tp3_reduktion_mue: 0.5
tp3_scn2a: 0.0 substance_id: 30131_A08
tp1_sift: -0.141
tp3_reduktion: 1.0
tp3_reduktion_mue: 0.0
tp3_scn2a: 0.0 substance_id: 10353_H11
tp1_sift: 0.76
tp3_reduktion: 0.0 substance_id: 30140_A08
tp1_sift: -0.324
tp3_reduktion: 0.0
tp3_scn2a: 0.0

DPP_4 substance_id: 10353_G08
tp1_sift: 0.675
tp3_reduktion: 1.0
tp3_reduktion_mue: 1.0
tp3_scn2a: 1.0 substance_id: 30139_B02
tp1_sift: 0.071
tp3_reduktion: 1.0
tp3_reduktion_mue: 0.5
tp3_scn2a: 1.0 substance_id: 10353_E03
tp1_sift: 1.303
tp1_sift_validation: -1.0
tp3_reduktion: 1.0
tp3_reduktion_mue: 0.0 substance_id: 10354_H03
tp1_sift: -0.093
tp3_reduktion: 1.0
tp3_reduktion_mue: 1.0
tp3_scn2a: 1.0 substance_id: 30137_A03
tp1_sift: 0.153
tp3_reduktion: 1.0
tp3_reduktion_mue: 1.0
tp3_scn2a: 0.5 substance_id: 30142_C08
tp1_sift: 0.349
tp3_reduktion: 1.0
tp3_reduktion_mue: 0.0
tp3_scn2a: 1.0

DPP_5 substance_id: 10353_C11
tp1_sift: 0.717
tp3_reduktion: 1.0
tp3_reduktion_mue: 1.0
tp3_scn2a: 0.0 substance_id: 30132_A07
tp1_sift: 0.718
tp3_reduktion: 1.0
tp3_reduktion_mue: 0.5
tp3_scn2a: 0.5 substance_id: 30134_F11
tp1_sift: -0.107
tp3_reduktion: 1.0
tp3_reduktion_mue: 0.0
tp3_scn2a: 0.5 substance_id: 30133_D04
tp1_sift: 0.273
tp3_reduktion: 1.0
tp3_reduktion_mue: 1.0
tp3_scn2a: 0.5 substance_id: 30138_F05
tp1_sift: -0.154
tp3_reduktion: 1.0
tp3_reduktion_mue: 1.0
tp3_scn2a: 1.0 substance_id: 30136_B07
tp1_sift: 0.4
tp3_reduktion: 1.0
tp3_reduktion_mue: 0.0
tp3_scn2a: 1.0

F) DPP_6 substance_id: 30165_G11
tp3_reduktion: 1.0 not classified substance_id: 30142_D07
tp1_sift: -0.034
tp3_reduktion: 0.0
tp3_scn2a: 0.0 substance_id: 30141_A07
tp1_sift: -0.193
tp3_reduktion: 0.0
tp3_scn2a: 0.0 substance_id: 30133_G10
tp1_sift: 0.143
tp3_reduktion: 0.0
tp3_scn2a: 0.0 substance_id: 30233_E03
tp1_sift: -0.517 sery260b
$C_{15}H_{10}BrClN_2O$
Mol. Wt.: 349,61 sery261a
$C_{78}H_{59}Br_4Cl_2FN_{10}O_5$
Mol. Wt.: 1625,89 sery269b
$C_{16}H_{13}ClN_2O$
Mol. Wt.: 284,74 sery301
$C_{16}H_{13}ClN_2O$
Mol. Wt.: 284,74 sery278b
$C_{15}H_{10}ClN_3O_2$
Mol. Wt.: 299,71 sery279b
$C_{17}H_{16}N_2O_3$
Mol. Wt.: 296,32 sery289
$C_{16}H_{13}ClN_2O$
Mol. Wt.: 284,74 sery290b
$C_{17}H_{16}N_2O_3$
Mol. Wt.: 296,32 sery300a
$C_{16}H_{13}BrN_2O_3$
Mol. Wt.: 361,19 sery302c
$C_{16}H_{11}N_3O_4$
Mol. Wt.: 309,28 sery275b
$C_{15}H_{12}ClN_3$
Mol. Wt.: 269,73 sery140
$C_{14}H_9FN_2O_3$
Mol. Wt.: 272,23 anle138b
$C_{16}H_{11}BrN_2O_2$
Mol. Wt.: 343,17 sery363b
$C_{18}H_{14}BrFN_2O_2$
Mol. Wt.: 389,22 sery319
$C_{16}H_{10}F_2N_2O_2$
Mol. Wt.: 300,26 sery145
$C_{17}H_{17}FN_2O_2$
Mol. Wt.: 300,33 sery345
$C_{16}H_{11}BrN_2O_2$
Mol. Wt.: 343,17 sery256b
$C_{16}H_{13}BrN_2O$
Mol. Wt.: 329,19 sery161
$C_{17}H_{15}FN_2O_2$
Mol. Wt.: 298,31 sery315b
$C_{17}H_{13}BrN_2O_2$
Mol. Wt.: 357,2 sery292b
$C_{19}H_{13}BrN_2$
Mol. Wt.: 349,22 sery329
$C_{18}H_{15}BrN_2O_3$
Mol. Wt.: 387,23 sery316b
$C_{16}H_{10}F_2N_2O_2$
Mol. Wt.: 300,26

DRUG FOR INHIBITING AGGREGATION OF PROTEINS INVOLVED IN DISEASES LINKED TO PROTEIN AGGREGATION AND/OR NEURODEGENERATIVE DISEASES

CROSS-REFERENCE TO RELATED PATENT APPLICATIONS

European Patent Office Priority Application 08010458.1 filed Jun. 9, 2008 including the specification, drawings, claims and abstract, is incorporated herein by reference in its entirety. This application is a Continuation of U.S. application Ser. No. 12/996,833 filed Aug. 9, 2011 which is the US National Stage of PCT/EP2009/004144 filed Jun. 9, 2009. All of the aforesaid applications are incorporated herein by reference in their entirety.

SUMMARY OF THE INVENTION

The present invention relates to a compound represented by formula (E). The present invention also relates to a compound represented by the formula (E) for use in the treatment or prevention of diseases linked to protein aggregation and/or neurodegenerative diseases. Moreover, the present invention relates to pharmaceutical and diagnostic compositions comprising the compound of the invention as well as to a kit. Furthermore, the present invention relates to a method of imaging deposits of aggregated protein. A kit for preparing a detectably labelled compound of the present invention is also disclosed.

Several documents are cited throughout the text of this specification. The disclosure content of the documents cited herein (including any manufacturer's specifications, instructions, etc.) is herewith incorporated by reference.

BACKGROUND OF THE INVENTION

M. Ono et al. (Bioorganic & Medicinal Chemistry 16 (2008) 6867-6872) describe certain beta-amyloid probes based on 3,5-diphenyl-1,2,4-oxadiazoles.

US 2007/0276034 discloses certain bis- and tris-dihydroxyaryl compounds and their methylenedioxy analogs and pharmaceutically acceptable esters, which are allegedly suitable for treating synucleinopathies.

WO 2008/131148 describes specific diphenyl-heteroaryl derivatives and their use for binding and imaging amyloid plaques.

Heterocyclic compounds which are useful as NURR-1 activators are disclosed in WO 2004/072050.

Radiolabeled ethylene glycol or polyethylene glycol is used as a labelling group on compounds that can be useful for imaging tissues in WO 2007/002540.

WO 98/17652 describes certain oxadiazole derivatives that a stated to be suitable for treating neurodegenerative disorders and cerebral ischaemia.

A large number of neurological and neurodegenerative diseases are known, many of which are presently not curable. These diseases include medical conditions such as Parkinson's disease, Chorea Huntington, Hallervorden-Spatz disease, Alzheimer's disease, senile dementia, Creutzfeldt-Jakob disease, artheriosclerotic dementia, cerebral thrombangitis obliterans, dementia with Lewy bodies (DLB), multiple system atrophy (MSA) and many others.

Prion diseases, which include diseases such as Creutzfeldt-Jakob disease (CJD), scrapie and bovine spongiform encephalopathy (BSE) are pathologically characterized by a spongiform degeneration of the brain. Prion diseases are caused by an unconventional infectious agent which consists primarily of the misfolded, aggregated, beta-sheet rich PrPSc isoform of the membrane glycoprotein PrPC.

Prion diseases have caused a major concern in regard to public health due to the emergence of BSE. Scientific evidence suggests that BSE has been transmitted to humans causing a new variant of Creutzfeldt-Jakob disease (vCJD) (Will et al. 1996, Bruce et al. 1997). It is not known how many people are currently incubating the disease and will be affected by vCJD in the future. The available evidence does not exclude an impending epidemic affecting a large number of patients (Andrews et al. 2000). This heightens the need to develop effective therapeutics in addition to implementing measures preventing further spread of the disease. In addition, recent evidence suggests that secondary transmission by blood transfusion may occur (LLewelyn et al., 2004).

The central event in the pathogenesis of prion diseases is the conversion of the cellular prion protein PrPC into the pathological PrPSc isoform, which aggregate into large protein aggregates. This formation of PrPSc aggregates is a hallmark of the pathogenesis of prion diseases. The available evidence suggests that PrPSc acts both as a template for this conversion and as a neurotoxic agent causing neuronal dysfunction and cell death (Prusiner 1998, Giese and Kretzschmar 2001). Therefore, the most promising therapeutic approach for prion diseases is interference with PrPSc amplification. Evidence derived from cell culture and in vivo studies suggests that once formation of PrPSc is inhibited, clearance of PrPSc can take place (Mallucci 2003). Thus, this therapeutic strategy could also be effective late in the incubation period and even after manifestation of clinical signs of disease, which is essential to be of use in addressing human prion disease.

There are a number of compounds which have been shown to be effective in interfering with PrPSc amplification in vitro such as acridin derivatives, Congo Red, porphyrins/phthalocyanines, Cp-60, beta-sheet breaker peptides and variants of PrP (Caughey et al. 1998, Chabry et al. 1998, Demaimay et al. 2000, Horiuchi et al. 2000, Perrier et al. 2000, Rudyk et al. 2000, Soto et al. 2000). However, none of these compounds have so far been used successfully for disease treatment or as lead compounds for developing compounds with increased therapeutic potency and pharmacological properties.

The substances identified so far as potential therapeutics have mainly been discovered by chance. Few in vitro assays suitable for high-throughput screening of large compound libraries for potential anti-prion drugs have been established so far. Two different approaches for systematic screening have been proposed in recently published studies: one being yeast-based (Bach et al. 2003) and the other using infected ScN2a cell cultures (Kocisko et al. 2004, Kocisko et al. 2003). However, these approaches allowed the screening of libraries limited to 2500 and 2000 compounds, respectively, and turned out to be time-consuming.

In addition to low molecular weight substances, three further potential approaches are tested currently. First, antibodies against PrP are being used to suppress the formation of PrPSc. This method has successfully been used in cell culture as well as in mice injected intraperitoneally (Enari et al., 2001; White et al., 2003). Another approach is the application of CpG oligonucleotides, which where found to increase the incubation period in scrapie-infected mice (Sethi et al., 2002). However, the mechanism of action of this method has not been elucidated so far. Finally, suppression of the expression of PrPC in neurons of infected animals or humans by siRNA is under discussion. This method has been shown to inhibit PrPSc formation in cell cultures (Daude et al., 2003). All three methods face the same problem, namely passage of the molecules through the blood-brain barrier. Due to this drawback, these approaches are only suitable for post exposition prophylaxis in peripheral organs but not for therapy of the disease in the central nervous system.

Another class of neurodegenerative diseases, the so-called synucleinopathies are characterized by intracellular accumulation of protein aggregates, oligomers, protofibrils and fibrils, containing mainly α-synuclein. In the cases of synucleinopathies it is believed that the pathological effects on nerve cells are induced by the formation of oligomeric aggregates of α-synuclein and the subsequent formation of membrane pores. Examples of synucleinopathies are Parkinson's disease (PD), dementia with Lewy bodies (DLB) and multiple system atrophy (MSA). So far, no therapeutic strategies are available for the inhibition of aggregation of α-synuclein.

Hence, there is a need to identify novel compounds suitable for the treatment of diseases linked to aggregating proteins, such as prion diseases and synucleinopathies.

Thus, the technical problem underlying the present invention is the provision of compounds for treating prion diseases, synucleinopathies and other diseases characterized by aggregating proteins, in particular Parkinson's disease. Furthermore, there is a need to provide compounds which are suitable probes for imaging deposits of aggregated proteins in the above mentioned disorders.

DESCRIPTION OF THE FIGURES

In FIG. 2 F a further cluster, DPP_6, is shown, which is not contained in the SAR-map in FIG. 1 and contains a single cell culture active compound with an N-atom attached to the pyrazole ring. In FIG. 2 F, additionally those 4 of the 33 DPP compounds from DIVERSet 1 and 2 are shown, which were found inactive in cell culture and which the DM program judged to be dissimilar to the six DPP classes. We have identified these compounds by a library search of the DPP motif.

DETAILED DESCRIPTION OF THE INVENTION

Figure 1:
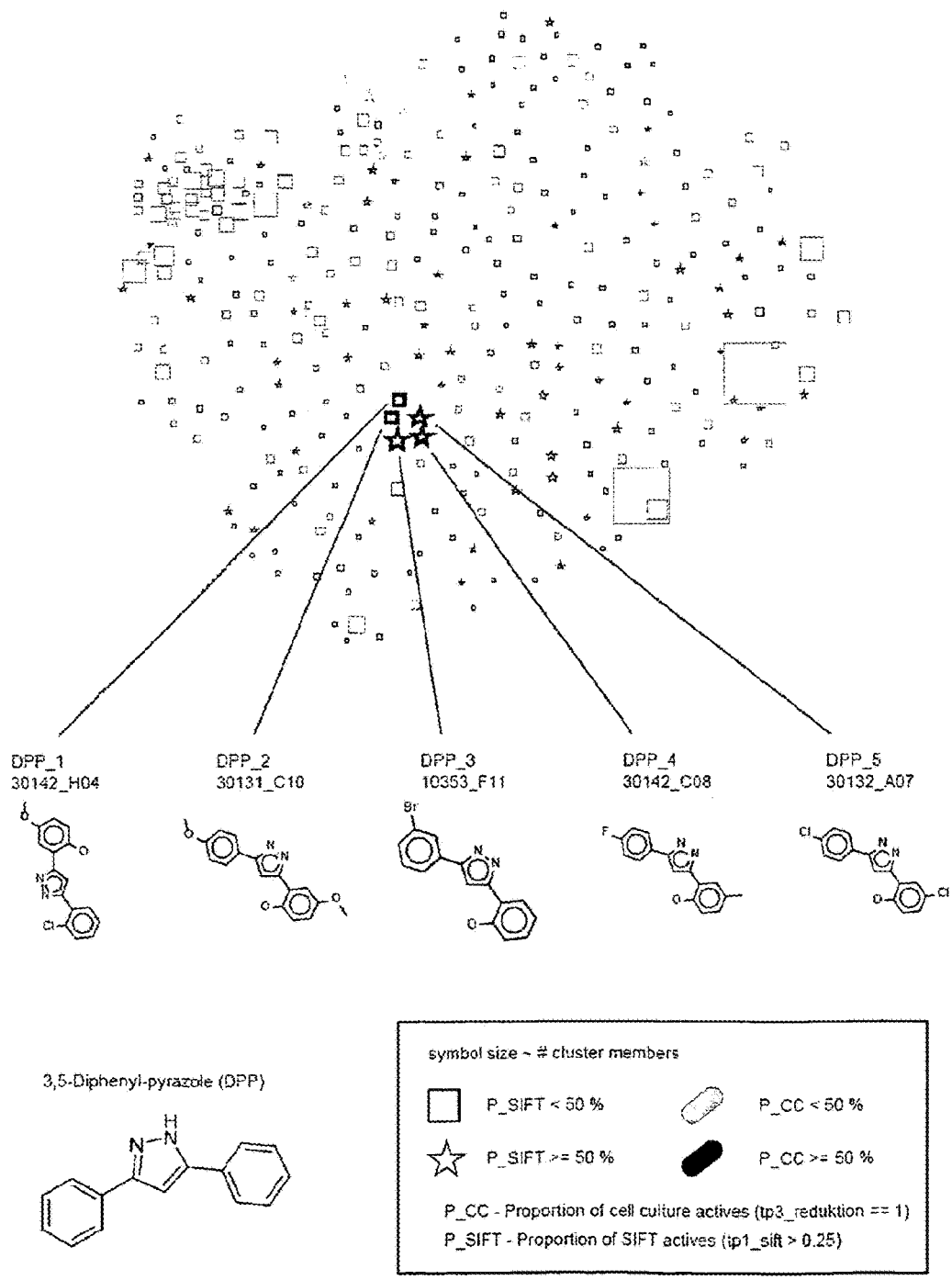
FIG. 1: SAR-Map generated for DIVERSet 1 and 2, screened by 2D-SIFT and in cell culture. The map shows clusters of structurally similar compounds (represented by stars or boxes) built from the 837 hit compounds of the primary cell culture screening of DIVERSet 1 and 2. The clusters in turn are arranged such that similar clusters are close to eachother. The symbols representing the clusters are scaled, shaped and colored according to their size and the proportions of SIFT-actives and cell culture actives, respectively, as explained in the legend. Thus larger clusters, containing large proportions of SIFT and cell culture actives are symbolized by large red stars. Five clusters, termed DPP_1 through DPP_5 are selected and prototypical compounds representing these clusters are displayed.
Figure 2:
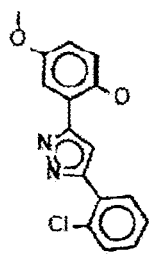
FIG. 2: All compounds sorted into the clusters identified (FIG. 1) are shown in FIG. 2 A to F together with their activities in the various assays. All of them belong to the chemical compound class of 3,5-Diphenyl-pyrazole (DPP) derivatives (cf. the DPP motif shown in FIG. 1).
Figure 2:
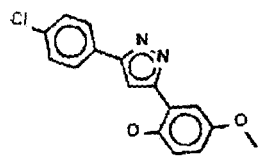
Figure 2:
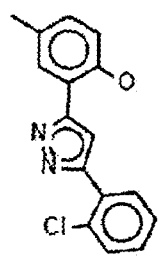
Figure 2:
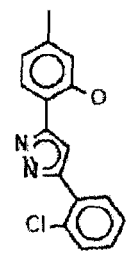
Figure 2:
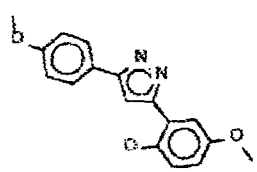
Figure 2:
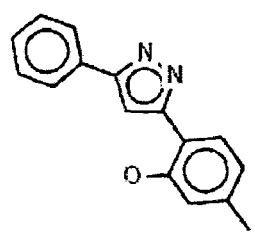
Figure 2:
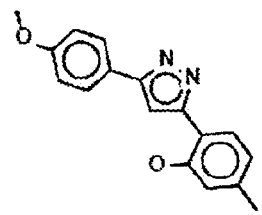
Figure 2:
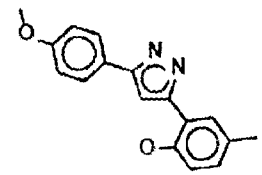
Figure 2:
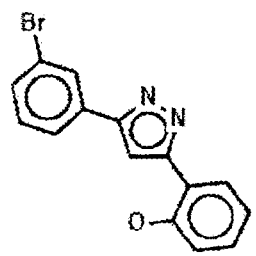
Figure 2:
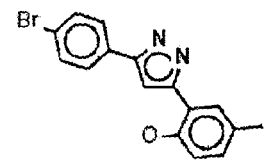
Figure 2:
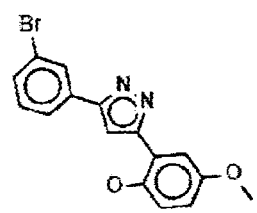
Figure 2:
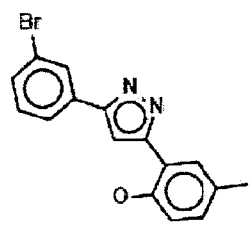
Figure 2:
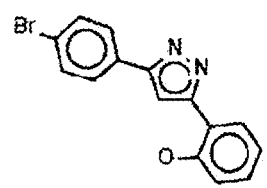
Figure 2:
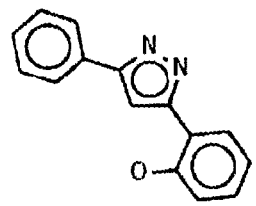
Figure 2:
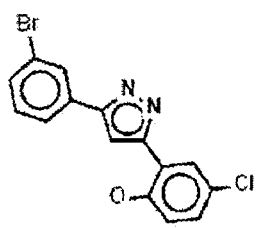
Figure 2:
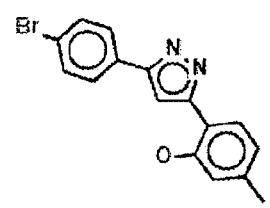
Figure 2:
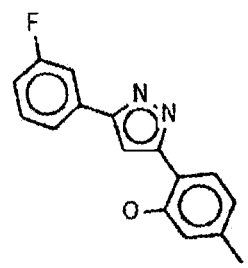
Figure 2:
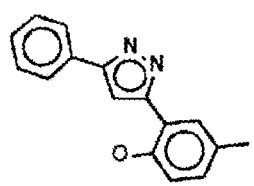
Figure 2:
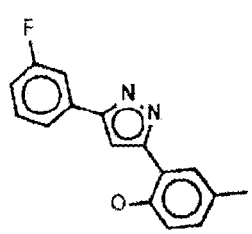
Figure 2:
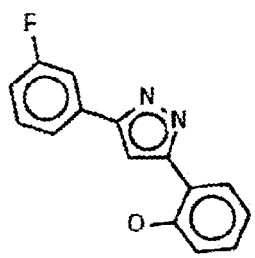
Figure 2:
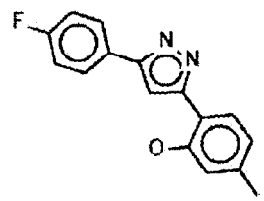
Figure 2:
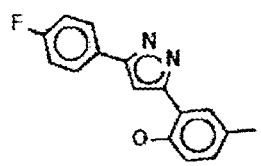
Figure 2:
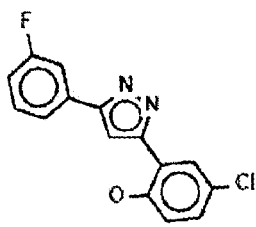
Figure 2:
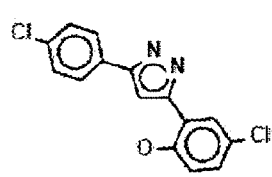
Figure 2:
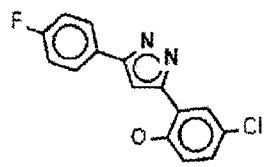
Figure 2:
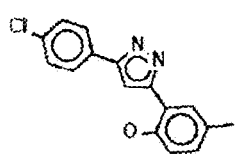
Figure 2:
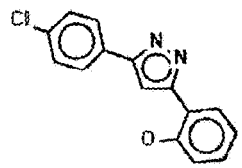
Figure 2:
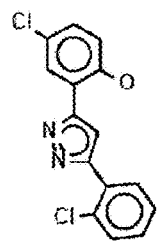
Figure 2:
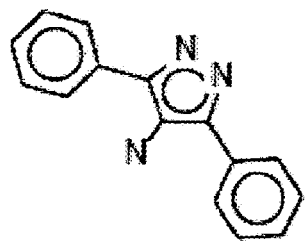
Figure 2:
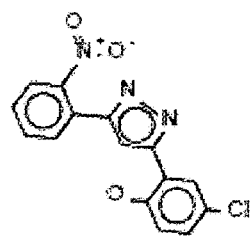
Figure 2:
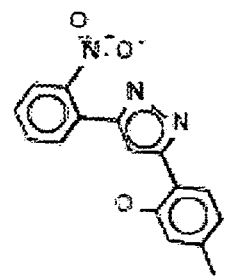
Figure 2:
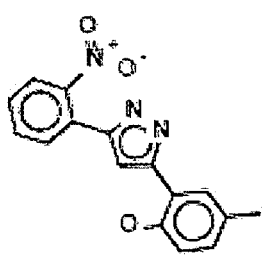
Figure 2:
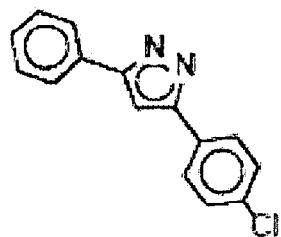

The invention is summarized by the embodiments listed in the claims. It is understood that combinations of all of the preferred embodiments listed hereinafter and in the claims are contemplated as being within the scope of the present invention.

The present invention relates to a compound represented by the general formula (E)

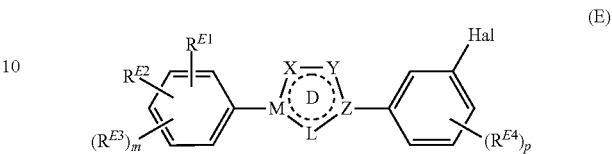

In the ring D X, Y and L are independently nondirectionally selected from —C($R^1$)($R^2$)—, —C($R^3$)=, —N($R^4$)—, —N=, —$N^+$($R^5$)=, —O— and —S—;

M and Z are independently nondirectionally selected from

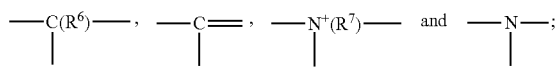

- - - - represents an optional double bond.

It is self evident that X, Y, Z, L and M will be selected as valency and stability permits.

$R^1$, $R^2$, $R^3$, $R^4$, $R^5$, $R^6$ and $R^7$ are independently selected from hydrogen; $C_{1-4}$ alkyl; —$C_{1-4}$ alkylene-halogen; —$C_{1-4}$ alkylene-OH; —$C_{1-4}$ alkylene-$C_{1-4}$ alkoxy; —C(O)—$C_{1-4}$ alkyl; and $C_{6-10}$ aryl, wherein the aryl ring can be optionally substituted by $C_{1-4}$ alkyl or halogen. The $C_{6-10}$ aryl group is not particularly limited and can be, e.g., selected from phenyl and naphthyl. The halogen atom can be F, Cl, Br or I and is typically F or Cl.

Preferably $R^1$, $R^2$, $R^3$, $R^4$, $R^5$, $R^6$ and $R^7$ are independently selected from hydrogen; $C_{1-4}$ alkyl; —$C_{1-4}$ alkylene-halogen; —$C_{1-4}$ alkylene-OH; —$C_{1-4}$ alkylene-$C_{1-4}$ alkoxy; and —C(O)—$C_{1-4}$ alkyl.

More preferably $R^1$, $R^2$, $R^3$, $R^4$, $R^5$, $R^6$ and $R^7$ are selected from hydrogen; $C_{1-4}$ alkyl; and —$C_{1-4}$ alkylene-halogen.

The choice of the substituent can depend on the intended use of the compounds of the formula (E). In one preferred embodiment at least one of $R^1$, $R^2$, $R^3$, $R^4$, $R^5$, $R^6$ and $R^7$ (more preferably at least one of $R^4$, $R^5$ and $R^7$) is —$C_{1-4}$ alkylene-halogen. This is particularly useful if the compounds are to be employed as a probe for for imaging deposits of aggregated proteins because it is then possible to label them quickly and efficiently with a detectable label such as a detectable halogen isotope. Examples of detectable halogen isotopes include $^{18}F$, $^{125}I$, $^{123}I$, $^{131}I$, $^{77}Br$ and $^{76}Br$, in particular $^{18}F$. It is of course possible to use a detectable halogen isotope as any of the other halogen atoms present in the compounds of the present invention, such as the halogen atoms attached to the phenyl ring.

Alternatively $^{11}C$ can be used to detectably label the compounds of the present invention. $^{11}C$ can be present in at least one of $R^1$, $R^2$, $R^3$, $R^4$, $R^5$, $R^6$ and $R^7$ (more preferably at least one of $R^4$, $R^5$ and $R^7$) or any other part of the compound of the present invention.

In an alternative preferred embodiment $R^1$, $R^2$, $R^3$, $R^4$, $R^5$, $R^6$ and $R^7$ are independently selected from hydrogen and $C_{1-4}$ alkyl, preferably hydrogen.

The ring D is not particularly limited. Typical examples thereof include

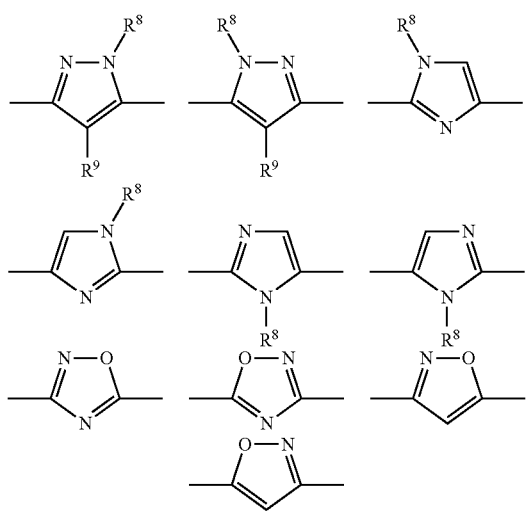

Particularly preferred examples of ring D are

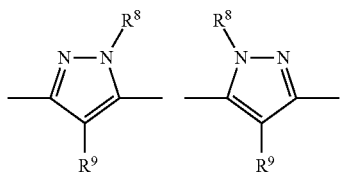

In the above formulae, $R^8$ is selected from hydrogen; $C_{1-4}$ alkyl; —$C_{1-4}$ alkylene-halogen; —$C_{1-4}$ alkylene-OH; —$C_{1-4}$ alkylene-$C_{1-4}$ alkoxy; —C(O)—$C_{1-4}$ alkyl; and $C_{6-10}$ aryl, wherein the aryl ring can be optionally substituted by $C_{1-4}$ alkyl or halogen. Preferably $R^8$ is selected from hydrogen; $C_{1-4}$ alkyl; —$C_{1-4}$ alkylene-halogen; —$C_{1-4}$ alkylene-OH; —$C_{1-4}$ alkylene-$C_{1-4}$ alkoxy; and —C(O)—$C_{1-4}$ alkyl. More preferably $R^8$ is selected from hydrogen; $C_{1-4}$ alkyl; —$C_{1-4}$ alkylene-halogen. In one embodiment $R^8$ is selected from hydrogen; and $C_{1-4}$ alkyl, more preferably hydrogen. In an alternative embodiment $R^8$ is —$C_{1-4}$ alkylene-halogen. As was explained above, $R^8$ can be detectably labelled, if desired.

In the above formulae, $R^9$ is selected from hydrogen; $C_{1-4}$ alkyl; —$C_{1-4}$ alkylene-halogen; —$C_{1-4}$ alkylene-OH; —$C_{1-4}$ alkylene-$C_{1-4}$ alkoxy; —C(O)—$C_{1-4}$ alkyl; and $C_{6-10}$ aryl, wherein the aryl ring can be optionally substituted by $C_{1-4}$ alkyl or halogen. Preferably $R^9$ is selected from hydrogen; $C_{1-4}$ alkyl; —$C_{1-4}$ alkylene-halogen; —$C_{1-4}$ alkylene-OH; —$C_{1-4}$ alkylene-$C_{1-4}$ alkoxy; and —C(O)—$C_{1-4}$ alkyl. More preferably $R^9$ is selected from hydrogen; $C_{1-4}$ alkyl; —$C_{1-4}$ alkylene-halogen. In one embodiment $R^9$ is selected from hydrogen; and $C_{1-4}$ alkyl, more preferably hydrogen. In an alternative embodiment $R^9$ is —$C_{1-4}$ alkylene-halogen. As was explained above, $R^9$ can be detectably labelled, if desired.

In a further embodiment $R^8$ and $R^9$ are hydrogen. In yet another embodiment $R^8$ is —$C_{1-4}$ alkylene-halogen and $R^9$ is hydrogen.

Hal is selected from F, Cl, Br, and I and is preferably F, Cl or Br, more preferably Cl or Br, most preferably Br.

$R^{E1}$ is selected from hydroxy, $C_{1-6}$ alkoxy, and —$NR^{E5}R^{E6}$.

$R^{E2}$ is selected from hydrogen, halogen, hydroxy, $C_{1-6}$ alkoxy, and —$NR^{E5}R^{E6}$, preferably $R^{E2}$ is selected from hydrogen, hydroxy, $C_{1-6}$ alkoxy, and —$NR^{E5}R^{E6}$.

In an alternative embodiment, $R^{E1}$ and $R^{E2}$ together can non-directionally form a structure -T-$(CR^{E7}R^{E8})_n$—V— as well as corresponding structures in which a double bond is present, if they are attached to adjacent carbon atoms. In this structure T is selected from $CR^{E9}R^{E10}$, NH and O and V is selected from $CR^{E9}R^{E10}$, NH and O. Preferably at least one of T and V is NH or O. Examples of such structures include —O—$(CH_2)_n$—O—, —O—$(CF_2)_n$—O—, —O—$(CH_2)_n$—$CH_2$—, —NH—$(CH_2)_n$—NH—, —NH—$(CF_2)_n$—NH—, —NH—$(CH_2)_n$—$CH_2$— or a corresponding structure in which a double bond is present. For instance, if n=1 then —N=CH—NH— is a structure in which a double bond is present and which corresponds to —NH—$CH_2$—NH—. Preferably $R^{E1}$ and $R^{E2}$ together form a structure —O—$(CH_2)_n$—O—. It is assumed that this group might also be hydrolyzed in vivo to the corresponding hydroxy groups.

n is 1 to 3; preferably n is 1 or 2, more preferably n is 1.

$R^{E5}$ and $R^{E6}$ are independently selected from hydrogen and $C_{1-6}$ alkyl; preferably $R^{E5}$ and $R^{E6}$ are independently selected from hydrogen and $C_{1-4}$ alkyl.

$R^{E7}$ and $R^{E8}$ are independently H or F, and are preferably H.

$R^{E9}$ and $R^{E10}$ are independently H or F, and are preferably H.

The position at which $R^{E1}$ and $R^{E2}$ are attached to the phenyl ring can vary.

In one embodiment $R^{E1}$ and $R^{E2}$ are independently hydroxy or alkoxy are attached meta and para compared to the carbon atom which binds the phenyl ring to ring D.

In a second embodiment $R^{E1}$ and $R^{E2}$ are a structure -T-$(CR^{E7}R^{E8})_n$—V— or a corresponding structure in which a double bond is present and are attached meta and para compared to the carbon atom which binds the phenyl ring to ring D. The above preferred definitions for the structure -T-$(CR^{E7}R^{E8})_n$—V— apply analogously to this embodiment.

In a third embodiment $R^{E1}$ is —$NR^{E5}R^{E6}$ and is attached in para position compared to the carbon atom which binds the phenyl ring to ring D.

Further substituents $R^{E3}$ can be optionally present on the phenyl ring in addition to $R^{E1}$, and $R^{E2}$. $R^{E3}$ can be a $C_{1-6}$ alkyl group or a $C_{5-10}$ aryl group (such as a phenyl or naphthyl group), preferably a $C_{1-6}$ alkyl group, more preferably a $C_{1-4}$ alkyl group. The number of substituents, m, is not particularly limited and is typically in the range of 0 to 2, preferably 0 or 1, typically 0.

Further substituents $R^{E4}$ can also be present. They are typically a halogen atom, a $C_{1-6}$ alkyl group or a $C_{5-10}$ aryl group (such as a phenyl or naphthyl group), preferably a halogen atom or a $C_{1-6}$ alkyl group, more preferably a $C_{1-6}$ alkyl group, most preferably a $C_{1-4}$ alkyl group. The number of substituents, p, is not particularly limited and is typically in the range of 0 to 2, preferably 0 or 1, typically 0.

In some embodiments the following compounds are excluded:

3(5)-(2-hydroxy-5-methylphenyl)-5(3)-(4-chlorophenyl) pyrazol (DE 41 26 543: compound 26 in Table 1);

ortho-hydroxyphenyl-5 dichloro-3'-4'phenyl-3 methyl-2 pyrazole (FR 2.104.932: Example IV);

ortho-hydroxyphenyl-5 dichloro-3'-4'phenyl-3 phenyl-2 pyrazole (FR 2.104.932: Example IV);

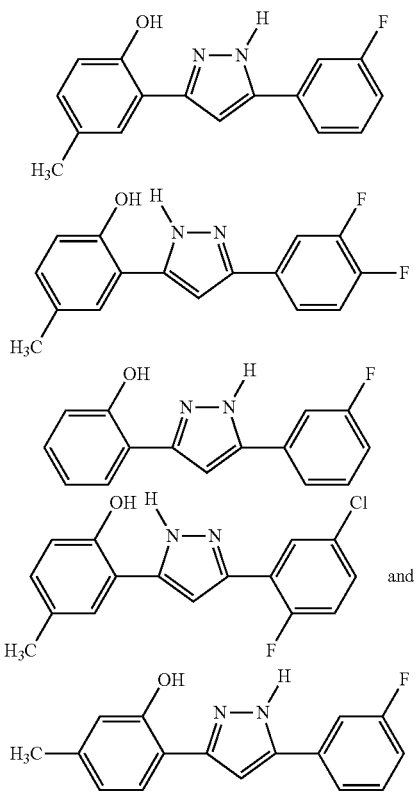

These compounds are disclosed as compounds IA-44, IA-47, IA-81, IA-106, and IA-115 in WO 2004/080972.

In other embodiments of the invention these compounds are not excluded.

Preferred examples of the compound represented by the formula (E) include compounds represented by formula (A)

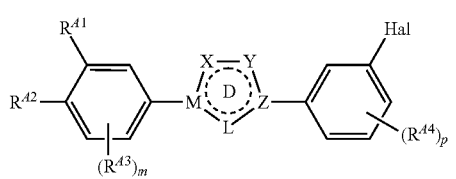

The definitions of X, Y, Z, M, L, ring D, m, p and Hal given above with respect to formula (E) apply analogously to formula (A).

$R^{A1}$ and $R^{A2}$ are each independently selected from hydrogen, halogen, hydroxy, $C_{1-6}$ alkoxy, and $-NR^{A5}R^{A6}$, with the proviso that at least one of $R^{A1}$ and $R^{A2}$ is hydroxy, $C_{1-6}$ alkoxy, or $-NR^{A5}R^{A6}$. Preferably $R^{A1}$ and $R^{A2}$ are independently selected from hydrogen, hydroxy, C16 alkoxy, and $-NR^{A5}R^{A6}$.

Alternatively $R^{A1}$ and $R^{A2}$ can together non-directionally form a structure $-T-(CR^{E7}R^{E8})_n-V-$. The explanations give above with respect to $R^{E1}$ and $R^{E2}$ forming such a structure and in particular the above definitions of $R^{E7}$, $R^{E8}$, T, n and V apply analogously to $R^{A1}$ and $R^{A2}$ forming this structure.

In one embodiment $R^{A1}$ and $R^{A2}$ are independently hydroxy or alkoxy.

In a second embodiment $R^{A1}$ and $R^{A2}$ are a structure $-T-(CR^{E7}R^{E8})_n-V-$ or a corresponding structure in which a double bond is present. The above preferred definitions for the structure $-T-(CR^{E7}R^{E})_n-V-$ apply analogously to this embodiment.

In a third embodiment $R^{A1}$ is $-NR^{A5}R^{A6}$ and $R^{A2}$ is hydrogen.

Further substituents $R^{A3}$ can be optionally present on the phenyl ring in addition to $R^{A1}$, and $R^{A2}$. $R^{A3}$ can be a $C_{1-6}$ alkyl group or a $C_{5-10}$ aryl group (such as a phenyl or naphthyl group), preferably a $C_{1-6}$ alkyl group, more preferably a $C_{1-4}$ alkyl group.

Further substituents $R^{A4}$ can also be present. They are typically a halogen atom, a $C_{1-6}$ alkyl group or a $C_{5-10}$ aryl group (such as a phenyl or naphthyl group), preferably a halogen atom or a $C_{1-6}$ alkyl group, more preferably a $C_{1-6}$ alkyl group, most preferably a $C_{1-4}$ alkyl group.

$R^{A5}$ and $R^{A6}$ are independently selected from hydrogen and $C_{1-6}$ alkyl; preferably $R^{A5}$ and $R^{A6}$ are independently selected from hydrogen and $C_{1-4}$ alkyl.

Preferred examples of the compound represented by the formula (E) include compounds represented by formula (B)

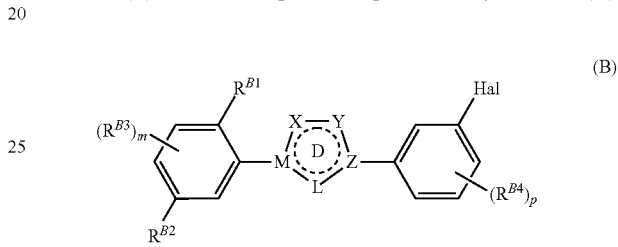

The definitions of X, Y, Z, M, L, ring D, m, p and Hal given above with respect to formula (E) apply analogously to formula (B).

$R^{B1}$ is selected from hydroxy, $C_{1-6}$ alkoxy, and $-NR^{B5}R^{B6}$. Preferably $R^{B1}$ is hydroxy or $C_{1-6}$ alkoxy.

$R^{B2}$ is selected from hydrogen, halogen, hydroxy, $C_{1-6}$ alkoxy; and $-NR^{B5}R^{B6}$, preferably $R^{B2}$ is selected from hydrogen, hydroxy, $C_{1-6}$ alkoxy; and $-NR^{B5}R^{B6}$ In one embodiment $R^{B1}$ is hydroxy or $C_{1-6}$ alkoxy and $R^{B2}$ is hydrogen.

$R^{B5}$ and $R^{B6}$ are independently selected from hydrogen and $C_{1-6}$ alkyl, preferably $R^{B5}$ and $R^{B6}$ are independently selected from hydrogen and $C_{1-4}$ alkyl.

Further substituents $R^{B3}$ can be optionally present on the phenyl ring in addition to $R^{B1}$, and $R^{B2}$. $R^{B3}$ can be a $C_{1-6}$ alkyl group or a $C_{5-10}$ aryl group (such as a phenyl or naphthyl group), preferably a $C_{1-6}$ alkyl group, more preferably a $C_{1-4}$ alkyl group.

Further substituents $R^{B4}$ can also be present. They are typically a halogen atom, a $C_{1-6}$ alkyl group or a $C_{5-10}$ aryl group (such as a phenyl or naphthyl group), preferably a halogen atom or a $C_{1-6}$ alkyl group, more preferably a $C_{1-6}$ alkyl group, most preferably a $C_{1-4}$ alkyl group.

Preferred compounds of the present invention include

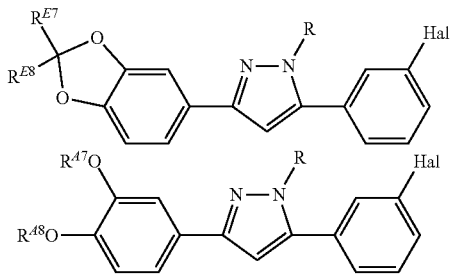

-continued

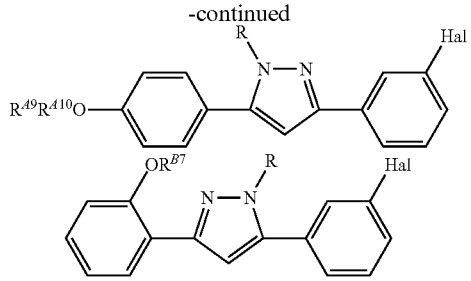

The definitions given above with respect to $R^{E7}$, $R^{E8}$ and Hal apply analogously to these compounds.

R is selected from hydrogen; $C_{1-4}$ alkyl; —$C_{1-4}$ alkylene-halogen; and $C_{6-10}$ aryl (such as phenyl and naphthyl), wherein the aryl ring can be optionally substituted by $C_{1-4}$ alkyl or halogen. Preferably R is selected from hydrogen; $C_{1-4}$ alkyl; —$C_{1-4}$ alkylene-halogen. In one embodiment R is selected from hydrogen; and $C_{1-4}$ alkyl, more preferably hydrogen. In an alternative embodiment R is —$C_{1-4}$ alkylene-halogen. As was explained above, R can be detectably labelled, if desired.

$R^{47}$ is H or $C_{1-6}$ alkyl, preferably H or $C_{1-4}$ alkyl.

$R^{48}$ is H or $C_{1-6}$ alkyl, preferably H or $C_{1-4}$ alkyl.

$R^{49}$ is H or $C_{1-6}$ alkyl, preferably H or $C_{1-4}$ alkyl.

$R^{410}$ is H or $C_{1-6}$ alkyl, preferably H or $C_{1-4}$ alkyl.

$R^{B7}$ is H or $C_{1-6}$ alkyl, preferably H or $C_{1-4}$ alkyl.

The following compounds are particularly preferred because they have been found to have a high efficacy in inhibiting the aggregation of proteins or in imaging aggregated proteins:

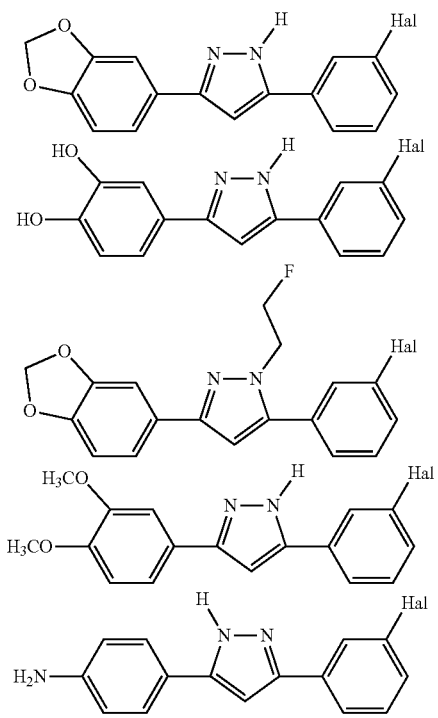

wherein Hal is Cl or Br, preferably Hal is Br.

Most preferred are presently the following compounds

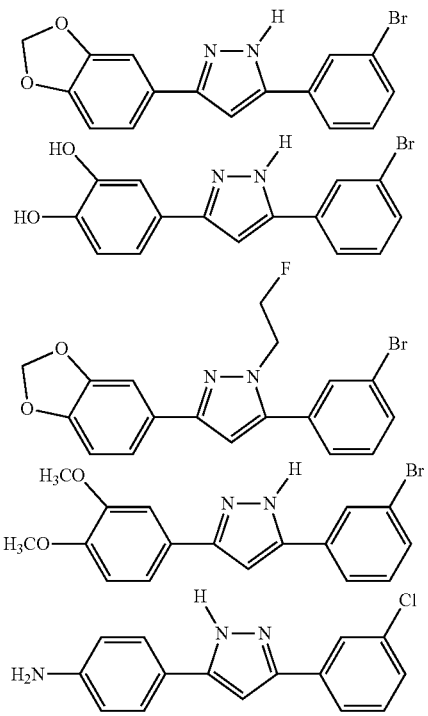

The compounds of the present invention can also be present in the form of prodrugs, esters, solvates or salts thereof.

The compounds of the present invention form salts which are also within the scope of this invention. Reference to a compound of the present invention herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound with an amount of acid or base, such as an equivalent amount, in a medium such as one in which the salt precipitates or in an aqueous medium followed by lyophilization.

The compounds which contain a basic moiety, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (e.g., those formed with sulfuric acid), sulfonates (e.g., those mentioned herein), tartrates, thiocyanates, toluenesulfonates such as tosylates, undecanoates, and the like.

The compounds which contain an acidic moiety, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (e.g., organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of the invention are also contemplated herein. The term "prodrug" as employed herein denotes a compound which, upon administration to a subject, undergoes chemical conversion by metabolic or chemical processes to yield a compound of the present invention or a salt and/or solvate thereof.

Solvates of the compounds of the present invention include, for example, hydrates.

Esters of the compounds of the present invention include $C_{1-6}$, preferably $C_{1-4}$ alkyl esters.

The compounds of the present invention may exist in their tautomeric form (e.g., as an amide or imino ether). All such tautomeric forms are contemplated herein as part of the present invention.

All stereoisomers of the present compounds (e.g., those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the compounds of the present invention may have the S or R configuration as defined by the IUPAC 1974 Recommendations.

The racemic forms can be resolved by physical methods, such as fractional crystallization, separation or crystallization of diastereomeric derivatives or separation by chiral column chromatography. The individual optical isomers can be obtained from the racemates by any suitable method, including without limitation, salt formation with an optically active acid followed by crystallization.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclo rings.

Throughout the specification, groups and substituents thereof may be chosen to provide stable moieties and compounds.

The compounds of the formula (E) can be provided in the form of a pharmaceutical or diagnostic composition which optionally includes a pharmaceutically acceptable carrier.

Applying a biochemical assay system based on the "scanning for intensely fluorescent targets (SIFT)" technique in combination with cellular assays in cell culture models of prion diseases the present inventors have screened large libraries of synthetic compounds in vitro for inhibitors of the aggregation processes accompanying neurodegenerative diseases and in particular prion diseases and synucleinopathies at the molecular level. Such inhibitors bear the potential of being novel therapeutics for these diseases.

This assay system surpasses by far all assay systems in use for the search of novel drugs for the inhibition of protein aggregation with respect to the degree of automation, the speed of measurement (75 seconds per sample), the amount of chemical compounds (only 200 picomoles per primary assay) as well as agent used (e.g. only the equivalent of 0.2 mg of brain from a CJD-case per assay) needed. Only these relatively low requirements of resources and time allow the screening of such high numbers (i.e. 20.000) of compounds. Furthermore, the mapping of all screening data onto a centralized data base and their automated analysis allow efficient evaluation and analysis of structure-activity relationships. The combination with cell culture screening procedures, which were included in the present invention, allows the identification of compounds being active both in biochemical as well as cell based assays. Thus, compounds are identified that are not only active in vitro, but also in a cellular context, e.g. ensuring appropriate stability and reactivity of the identified compounds to be further developed for in vivo applications.

Thus, the present inventors identified a number of active compounds in this primary screening, which were subsequently validated in dilution series in order to identify compounds active even at very low concentrations. The compounds characterized as "active" in the primary screening were subjected to a cluster analysis, which revealed a group of five neighbouring clusters (DPP_1 through DPP_5; FIG. 1), comprising highly active compounds, belonging to the chemical compound class of 3,5-diphenyl-pyrazole (DPP) derivatives (cf. the DPP motif shown in FIG. 1).

The present inventors further substituted various substituents of the identified compound class to identify related compounds suitable as inhibitors of the aggregation processes accompanying neurodegenerative diseases and in particular prion diseases and synucleinopathies at the molecular level. Using this medicinal-chemical approach, a number of additional compounds were synthesized. These compounds, together with selected substances of the initial screening, where subjected to further tests, including SIFT assays, cell culture based assays, in vivo experiments on mice as well as biochemical assays directed to α-synuclein aggregation (see Examples). Thus, the activity of these compounds both in vitro as well as in vivo was verified. The finding that these compounds are also capable of efficiently inhibiting the multimer formation of α-synuclein at low micro-molar concentrations in in vitro models for this pathological protein aggregation found in synucleinopathies is a clear indication that the identified compounds cannot only function as anti-prion compounds, but have also therapeutic potential for synucleinopathies, like Parkinson's Disease, DLB, and MSA, by targeting the pathologic mechanism at the molecular level. Furthermore, the inhibitory activity of these compounds on both, prion protein- and α-synuclein-aggregation in vitro, may reflect their general anti-aggregatory activity against a broader range of protein aggregation diseases, where protein misfolding into predominantly β-sheet conformations forms the basis for subsequent protein aggregation into amyloid fibrils. Therefore, these compounds and compounds related to members of the DPP-class of substances have the potential of being useful as therapeutics for the causative treatment of a whole panel of (neurodegenerative) protein aggregation diseases, including, but not limited to, Parkinson's disease, prion disease, Alzheimer's disease, multiple system atrophy, Diffuse Lewy body disease, frontotemporal dementia, amyotrophic lateral sclerosis, Huntington disease's, spinocerebellar ataxias and other Poly-Q diseases, hereditary cerebral amyloid angiopathy, familial amyloid polyneuropathy, primary systemic amyloidosis (AL amyloidosis), reactive systemic amyloidosis (AA amyloidosis), type II diabetes, injection-localized amyloidosis, beta-2 microglobulin amyloidosis, hereditary non-neuropathic amyloidosis, Finnish hereditary systemic amyloidosis.

The present invention further relates to the compound of the present invention as well as a prodrug, ester, solvate or salt thereof for the use in the treatment or prevention of a disease linked to protein aggregation and/or a neurodegenerative disease. Further embodiments are the use of a compound of the present invention for the preparation of a pharmaceutical composition for treating or preventing a disease linked to protein aggregation and/or a neurodegenerative disease as well as a method of treating or preventing a disease linked to protein aggregation and/or a neurodegenerative disease comprising administering a therapeutically effective amount of a compound of the present invention to a patient in need thereof.

The term "aggregation", in accordance with the present invention, refers to the formation of oligomeric or multimeric complexes of typically one or more types of proteins, which may be accompanied by the integration of additional biomolecules, like carbohydrates, nucleic acids and lipids, into the complexes.

The term "protein involved in a disease linked to protein aggregation and/or a neurodegenerative disease" as used herein, refers to those diseases which are characterized by the presence of aggregated proteins. Such aggregated proteins may form deposits in specific tissue, more preferably in nerve tissue or tissue of the brain. The extent of aggregation depends on the particular disease.

The present invention further relates to the use of a compound of the present invention as defined above for the preparation of a pharmaceutical composition for treating or preventing a disease linked to protein aggregation and/or a neurodegenerative disease.

In accordance with the present invention, the term "pharmaceutical composition" relates to a composition for administration to a patient, preferably a human patient. The pharmaceutical composition of the invention comprises the compounds recited above and, optionally, further molecules capable of altering the characteristics of the compounds of the invention thereby, for example, stabilizing, modulating and/or activating their function. The composition may be in solid, liquid or gaseous form and may be, inter alia, in the form of (a) powder(s), (a) tablet(s), (a) solution(s) or (an) aerosol(s). The pharmaceutical composition of the present invention may, optionally and additionally, comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, organic solvents including DMSO etc. Compositions comprising such carriers can be formulated by well known conventional methods.

The pharmaceutical composition will be formulated and dosed in a fashion consistent with good medical practice, taking into account the clinical condition of the individual patient, the site of delivery of the pharmaceutical composition, the method of administration, the scheduling of administration, and other factors known to practitioners. The "effective amount" of the pharmaceutical composition for purposes herein is thus determined by such considerations. The skilled person knows that the effective amount of pharmaceutical compositions administered to an individual will, inter alia, depend on the nature of the compound.

Pharmaceutical compositions of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The pharmaceutical composition is also suitably administered by sustained release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58 481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133 988). Sustained release pharmaceutical composition also include liposomally entrapped compound. Liposomes containing the pharmaceutical composition are prepared by methods known per se: DE 32 18 121; Epstein et al., Proc. Natl. Acad. Sci. (USA) 82:3688-3692 (1985); Hwang et al., Proc. Natl. Acad. Sci. (USA) 77:4030-4034 (1980); EP 52 322; EP 36 676; EP 88 046; EP 143 949; EP 142 641; Japanese Pat. Appl. 83-118008; U.S. Pat. Nos. 4,485,045 and 4,544,545; and EP 102324. Ordinarily, the liposomes are of the small (about 200-800 Angstroms) unilamellar type in which the lipid content is greater than about 30 mol % cholesterol, the selected proportion being adjusted for the optimal therapy.

For parenteral administration, the pharmaceutical composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the components of the pharmaceutical composition uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient.

Examples of such carrier vehicles include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts;

antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The components of the pharmaceutical composition to be used for therapeutic administration must be sterile. Sterility is readily accomplished by filtration through sterile filtration membranes (e.g., 0.2 µm membranes). Therapeutic components of the pharmaceutical composition generally are placed into a container having a sterile access port, for example, an intravenous solution bag or vial having a stopper pierceable by a hypodermic injection needle.

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

The present invention further relates to a method of treating or preventing a disease linked to protein aggregation and/or a neurodegenerative disease comprising administering a therapeutically effective amount of a compound of the present invention to a patient in need thereof.

As used herein the term "therapeutically effective amount" refers to an amount sufficient to elicit the desired biological response. In the present invention the desired biological response is the inhibition of protein aggregation.

The present invention further relates to a method of identifying a compound with enhanced efficacy for inhibiting aggregation of a protein involved in a disease linked to protein aggregation and/or a neurodegenerative disease, comprising the steps of (a) bringing into contact a labeled monomeric protein and a differently labeled aggregate of said protein in the (1) presence and/or (2) absence of a candidate inhibitor of aggregation which is a derivative of a compound as defined above; (b) determining the amount of co-localized labels representing the extent of binding of the monomeric protein to the aggregate of said protein; and (c) comparing the result obtained in the presence and absence of said compound, wherein a decrease of co-localized labels in the presence of said compound is indicative of the compound's ability to inhibit aggregation of said protein.

As used herein, the term "monomeric protein" refers to a molecular unit composed of one single (poly)peptide chain with a three-dimensional conformation specific for each particular protein which is preferably soluble in aqueous solutions up to typically nanomolar, micromolar or milimolar concentrations and may be modified by covalent linkage of one or more carbohydrates, carbohydrate derivatives, lipids, phosphate, sulfate, fatty acids, and nucleotides to individual amino acids in the chain. Preferably, said modification is a phosphorylation, glycosylation, proteolytic processing, glycation, oxidation, and nitration. The term "(poly) peptide" as used herein describes a group of molecules which comprises the group of peptides, consisting of up to 30 amino acids, as well as the group of polypeptides, consisting of more than 30 amino acids. As used throughout the present invention, the term "protein" also refers to (poly)peptides.

The term "aggregated protein" means non-covalently linked oligomers or multimers of one or more types of "monomeric protein(s) or polypeptide(s)", as defined above, which are characterized by an altered three-dimensional conformation of the complexed protein units with respect to the monomeric protein units and a typically low solubility of the complexes in aqueous solutions.

The term "compound for inhibiting protein aggregation" refers to a compound which is capable of preventing the formation of protein aggregates and/or which is capable of disintegrating or breaking down existing protein aggregates, wherein
said compounds are derived from the compounds of the invention by derivatization. Preferably, such compounds are designed by computer modeling, wherein computer modeling means using virtual-screening tools for the search of compounds that bind to the monomeric or the aggregated form of the protein or both. Generally, these methods rely on the three-dimensional structure of proteins, preferably of proteins crystallized together with a substrate. More preferably, the substrate is replaced with a candidate modulator or inhibitor.

The term "labeled . . . protein" refers to a protein to which a label is attached. Said label may be attached directly or indirectly. Indirect labeling particularly refers to labeled (poly)peptides, more particularly labeled antibodies. Attachment of the label can be performed by a number of techniques known to the person skilled in the art and described in standard textbooks (see for example Harlow and Lane "Antibodies, A Laboratory Manual", CSH Press, Cold Spring Harbor, 1998).

The term "differently labeled protein" means that different labels are attached to the aggregated and the monomeric isoform of the protein. A typical example is the attachment of "FITC" to the aggregated protein and of "Texas red" to the monomeric protein. Since these labels are detectable at different wavelengths of light, it is possible to determine the amount and/or the location of the isoforms of the protein. More particularly, the use of different labels allows to quantify the presence of co-localized labels, i.e. of labels which are found in close proximity to each other.

"Determining the amount of co-localized labels" may be performed, e.g. by separately measuring (i.e. wavelength-specific) the number of single photons of at least two different wavelengths coming from the same small volume element of typically less than 1 femtoliter of a sample within a very short time period of typically less than 100 µs followed by the computerized comparison of the respective photon numbers, which may be represented graphically in a multidimensional histogram with one axis for the number of photons of one particular wavelength. In the case of two wavelengths the photon numbers of a particular time period may thus be represented as single dots in a two dimensional fluorescence intensity histogram.

The term "comparing the result obtained in the presence and absence of said compound" means assessing the effect of the compound on the formation and/or amount of protein aggregates. As used herein, a decrease of co-localized labels of more than 10%, more preferably of more than 25%, even more preferably of more than 50% and most preferably of more than 95%, in the presence of a candidate inhibitor compound of aggregation, is indicative of the compounds ability to inhibit protein aggregation. The term "absence of said compound" means that no inhibitor or candidate inhibitor is or has been added to the aggregating protein. In particular cases it may be useful to add negative controls, i.e. compounds which have no effect on protein aggregation. The term "absence of said compound" also refers to these cases. Likewise, any of the compounds of the present application which inhibit protein aggregation may be used as positive controls in assays for identifying novel inhibitor compounds. It is apparent that the term "presence" also refers to quantity. For apparent reasons, the compounds referred to in the present invention have different effective concentrations. Preferably effective concentrations are less than 100 µM, more preferably below 10 µM and even more preferably below 1 µM.

The method of the present invention is particularly useful for identifying novel compounds capable of interfering with protein aggregation with an enhanced efficacy. It allows screening of large libraries of derivatized compounds and permits identifying inhibiting compounds with high fidelity. In one aspect of the present invention, the method is based on fluorescence correlation spectroscopy. In recent years fluorescence correlation spectroscopy (FCS) has been recognized as a method that allows highly sensitive analysis of protein aggregation in neurodegenerative diseases such as prion diseases at the molecular level (Bieschke and Schwille 1997, Bieschke et al. 2000, Giese et al. 2000, Post et al. 1998). Moreover, FCS lends itself to miniaturization and automation and has become an established method for high-throughput screening in the pharmaceutical industry (Koltermann et al. 1998). Fluorescence correlation spectroscopy (FCS) in its current confocal form analyses the signal fluctuations caused by the diffusion of single fluorescently labeled molecules through an open volume element defined by the beam of an excitation laser focused through a high aperture microscope objective and confocally imaged on a single photon counting detector (Schwille et al. 1997). In its most preferred embodiment, the method of the present invention is based on this technology. This method is suited for high-throughput screening based on the inhibition of, for example, PrPC binding to aggregates of PrPSc or the formation of oligomers or protofibrils or fibrils of α-synuclein.

This assay system for the detection of inhibitors of protein aggregation may be used for the search of new therapeutics for any neurodegenerative disease that is linked to aggregation of specific proteins such as Alzheimer's disease and Parkinson's disease. Moreover, it should be possible to search for potential therapeutics for all diseases, where multimer formation plays a crucial role in pathogenesis irrespective of the chemical nature of their components.

In a preferred embodiment of the present invention, said labels are fluorescent labels.

Preferably, the label is selected from the group consisting of fluorochromes, e.g. fluorescein isothiocyanate (FITC), rhodamine, Texas Red, Alexa 488, Alexa 647, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may also be a two stage system, where e.g. the protein or (poly)peptide or compound of the present invention is conjugated to biotin, haptens, etc. having a high affinity binding partner, e.g. avidin, specific antibodies, etc., where the binding partner is conjugated to a detectable label.

In another preferred embodiment of the present invention, said labels are attached to an antibody or a fragment of an antibody specifically bound to said protein.

The term "specific binding" of antibodies may be described, for example, in terms of their cross-reactivity. Preferably, "antibody specifically bound to . . . " refers to antibodies that do not bind (poly)peptides with less than 98%, less than 95%, less than 90%, less than 85%, less than 80%, less than 75%, less than 70% and less than 65% identity (as calculated using methods known in the art) to a (poly)peptide encoded by the aggregating protein. Antibodies may, however, also be described or specified in terms of their binding affinity. Preferred binding affinities include those with a dissociation constant or $K_d$ less than $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

The term "antibody" refers to polyclonal, monoclonal, chimeric, humanized antibodies, single chain, single chain Fv, antibody, or antibody fragments, like, inter alia, Fab fragments. Antibody fragments or derivatives further comprise F(ab')$_2$, Fv or scFv fragments; see, for example, Harlow and Lane (1988) and (1999), loc. cit. Various procedures are known in the art and may be used for the production of such antibodies and/or fragments. Thus, the (antibody) derivatives can be produced by peptidomimetics. Further, techniques described for the production of single chain antibodies (see, inter alia, U.S. Pat. No. 4,946,778) can be adapted to produce single chain antibodies specific for polypeptide(s) and fusion proteins of this invention. Also, transgenic animals may be used to express humanized antibodies specific for polypeptides and fusion proteins of this invention. Most preferably, the antibody of this invention is a monoclonal antibody. For the preparation of monoclonal antibodies, any technique which provides antibodies produced by continuous cell line cultures can be used. Examples for such techniques include the hybridoma technique (Köhler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Surface plasmon resonance as employed in the BIAcore system can be used to increase the efficiency of phage antibodies which bind to an epitope of an polypeptide of the invention (Schier, Human Antibodies Hybridomas 7 (1996), 97-105; Malmborg, J. Immunol. Methods 183 (1995), 7-13). It is also envisaged in the context of this invention that the term "antibody" comprises antibody constructs which may be expressed in cells, e.g. antibody constructs which may be transfected and/or transduced via, amongst others, viruses or plasmid vectors. The skilled person knows that in many cases antibodies can be replaced with other specifically binding compounds such as peptides exposed on the surface of phages (phage display) or with isolated (poly)peptides. The antibody or (poly)peptides may be unlabeled or labeled with any of the labels described in the present invention. Preferably, antibodies are obtainable from human, mouse, rat, goat or rabbit.

In a more preferred embodiment of the present invention, said antibody is capable of discriminating between the aggregated and monomeric protein.

The term "capable of discriminating" refers to an antibody which is specific to either the monomeric or the aggregated isoform of the protein. Preferably, said antibody has a 5 fold decreased $K_d$ for one isoform of the protein, more preferably the $K_d$ is 10 fold decreased. As a consequence, said antibody is capable of binding to one isoform of the protein whereas it essentially fails to bind to the other isoform.

In another preferred embodiment of the present invention, the amount of co-localized label is determined by using the method of "scanning for intensely fluorescent targets (SIFT)" (Bieschke et al. 2000), FRET or high resolution confocal imaging.

Preferably, said high resolution confocal imaging is performed with a confocal laser scanning microscope or with a microscope utilizing spinning disc technology.

In another preferred embodiment of the present invention, said monomeric and aggregating proteins are selected from the group consisting of prion protein, Amyloid precursor protein (APP), alpha-synuclein, superoxide dismutase, tau, immunoglobulin, Amyloid-A, transthyretin, Beta2-microglobulin, cystatin C, Apolipoproteine A1, TDP-43, Islet amyloid polypeptide, ANF, gelsolin, insulin, lysozyme, fibrinogen, huntingtin and ataxin and other proteins with a Poly-Q stretch, and fragments or derivates of said proteins. In a preferred embodiment, the monomeric and aggregating proteins are selected from the group consisting of Amyloid precursor protein (APP) and alpha-synuclein. In a more preferred embodiment, the monomeric and aggregating proteins are alpha-synuclein.

Preferably, said proteins with a Poly-Q stretch are proteins which have at least 36 consecutive glutamine residues. More preferably, said proteins with Poly-Q stretch are selected from the group consisting of huntingtin and ataxin.

Preferably, said fragments or derivatives are selected from the group modified by phosphorylation, glycosylation, proteolytic processing, glycation, oxidation, and nitration. The (poly)peptides mentioned in the present invention may contain one or more carbohydrates, carbohydrate derivatives, lipids, phosphate, sulfate, fatty acids, and nucleotides attached to individual amino acids in the chain. Preferably, said modification is a phosphorylation, glycosylation, proteolytic processing, glycation, oxidation, and nitration.

The protein may be a vertebrate or invertebrate protein. Preferably, the protein is a mammalian or avian protein. More preferably, the mammalian protein is selected from primate, human, mouse, rat, bos (cattle), sus (pig), and sheep. In particular cases it may be preferable to use mixed isoforms, i.e. for example the aggregated form PrPSc derived from human and the monomeric form derived from mouse.

The proteins may be isolated from an animal or from tissue culture or may be prepared recombinantly. It is envisaged by the inventors, that the proteins may be chemically modified or treated by enzymes such as proteases or glycosidases in order to improve handling in the assay system.

In another more preferred embodiment of the present invention, the monomeric protein is prion protein and the aggregated protein is PrPSc (Prusiner, 1998).

In another more preferred embodiment of the present invention, the monomeric protein is alpha-Synuclein and said aggregated protein is selected from the group consisting of oligomers or protofibrils or fibrils of alpha-Synuclein.

The present invention also relates to a method of selecting compounds with improved in vivo efficacy in the treatment of diseases linked to protein aggregation and/or neurodegenerative diseases, comprising (a) administering a candidate compound which is a derivative of the compound as defined in the present invention to a cell culture or an animal having the aggregatable isoform of the protein as defined in the present invention; (b) quantifying the amount of observable aggregates; and (c) identifying and selecting a compound which is capable of reducing aggregates or the formation of aggregates of said protein.

This method of the present invention allows testing candidate compounds in vivo, i.e. in cells within or outside of a living organism. Testing candidate compounds in vivo is for example shown in the examples (vide infra). Testing candidate compounds in vivo gives important additional information including data regarding toxicity, stability in the presence of a complex chemical environment, and ability to reach the location where a desired molecular effect is achieved.

Preferably, the compound is administered in various concentrations in order to determine a concentration at which an effect on protein aggregation can be observed and in order to calculate the $EC_{50}$, wherein the term $EC_{50}$ refers to the (molar) concentration of a compound, which produces 50% of the maximum possible response for that compound.

The present invention also relates to the use of a compound as defined above for inhibiting protein aggregation in an animal, in vitro or ex vivo.

In a preferred embodiment the animal is a non-human animal.

The present invention further relates to a pharmaceutical or diagnostic composition comprising the compound of the invention and optionally a pharmaceutically acceptable carrier or excipients.

In accordance with the present invention, the term "diagnostic composition" relates to compositions for diagnosing individual patients for their potential response to or curability by the pharmaceutical compositions of the invention. The term "diagnostic composition" also relates to compositions for the determination of the presence of aggregated proteins underlying the diseases recited above. The diagnostic composition of the invention comprises the compounds recited above. The diagnostic composition may further comprise appropriate buffer(s), and enzymes such as reverse transcriptase, thermostable polymerases etc. The diagnostic compositions may be packaged in a container or a plurality of containers.

In a more preferred embodiment of the invention, efficacy of said compound is further improved by derivatization.

The term "derivatization" in accordance with the present invention refers to the generation of chemically related compounds which have modifications in at least one position of the molecule.

In a preferred embodiment of the present invention, said compound is detectable or detectably labeled. It is understood in accordance with the present invention that a compound is detectable or detectably labeled if its presence can be monitored by conventional techniques such as NMR spectroscopy, optical detection, positron emission tomography (PET), electron microscopy, magnetic resonance imaging (MRI), spectrometry, chromatography, ELISA assay, detection of radioactive emission, preferably by scintillation counting or gamma counting, preferably PET.

When the compounds of the present invention are to be used as probes for imaging aggregated proteins, in particular amyloid deposits, they must be labelled. The specific nature of the label will depend on the method which is to be used for imaging. Typically radioactive labels which emit positrons (PET) and which have a short half life such as $^{18}F$, $^{11}C$, $^{125}I$, $^{123}I$, $^{131}I$, $^{77}Br$ and $^{76}Br$, in particular $^{18}F$ and $^{11}C$, will be useful. Due to their short half lifes the labelled compounds of the present invention should be prepared shortly before they are used for testing. Consequently, the diagnostic composition of the present invention can also be provided in the form of a kit, which consists of precursors of the compounds of the present invention, which are reacted to form the desired compound. Such a kit is particularly convenient, if the compound of the present invention contains at least one moiety which is X, Y or L that is —N(R⁴)— and R⁴ comprises a detectable label.

In a preferred embodiment of the present invention the compound which is used for imaging possesses a moiety —N(R⁴)— as X, Y or L, in which R⁴ is —C$_{1-4}$ alkylene-halogen, wherein the halogen atom is radioactive. In another preferred embodiment of the present invention the compound which is used for imaging possesses a moiety —N(R⁴)— as X, Y or L, in which R⁴ is —C$_{1-4}$ alkyl, which contains at least one $^{11}$C isotope.

A skilled person will be able to devise methods with which the detectable label can be attached to the compounds of the present invention. The following schemes can serves as illustrative examples.

2-[$^{18}$F]Fluoroethyl tosylate 2 is a useful precursor for incorporating $^{18}$F (half-life 109.8 min) via fluoroethylation of compounds containing oxygen, sulphur, and nitrogen nucleophiles or via various metal mediated methylations (R. Schirrmacher et al., J. Label. Compd. Radiopharm. 2002, 45, 763-774). 2-[$^{18}$F]fluoroethyltosylate can be synthesized in a two-step synthesis by direct nucleophilic substitution of ethylene glycol-1,2-ditosylate 1 by direct nucleophilic substitution with K[$^{18}$F]/Kryptofix 2.2.2 to yield the $^{18}$F-fluoroethylating agent 2. Non-radioactive reagent 2 was used for the synthesis of non-radioactive sery 363A, sery 363B, and sery 388B according to scheme A. The same conditions can be used for the synthesis of radioactive analogs of these compounds.

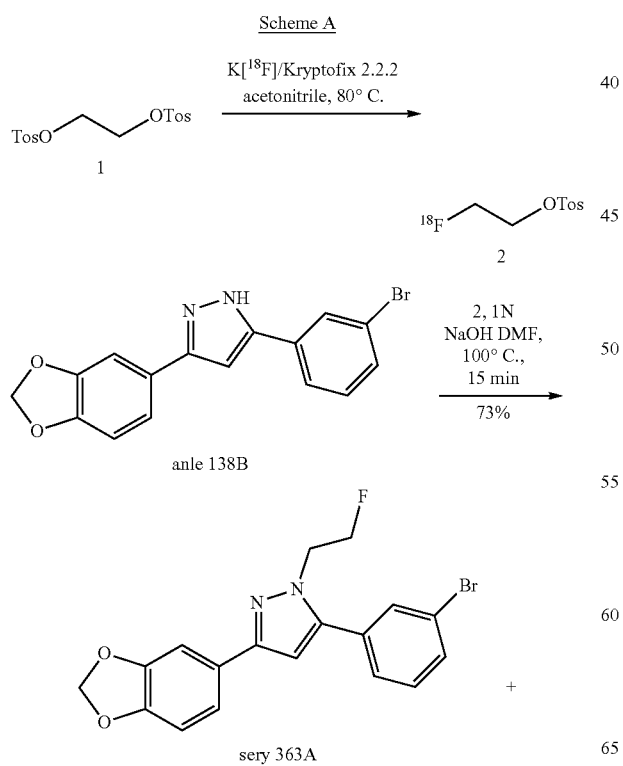

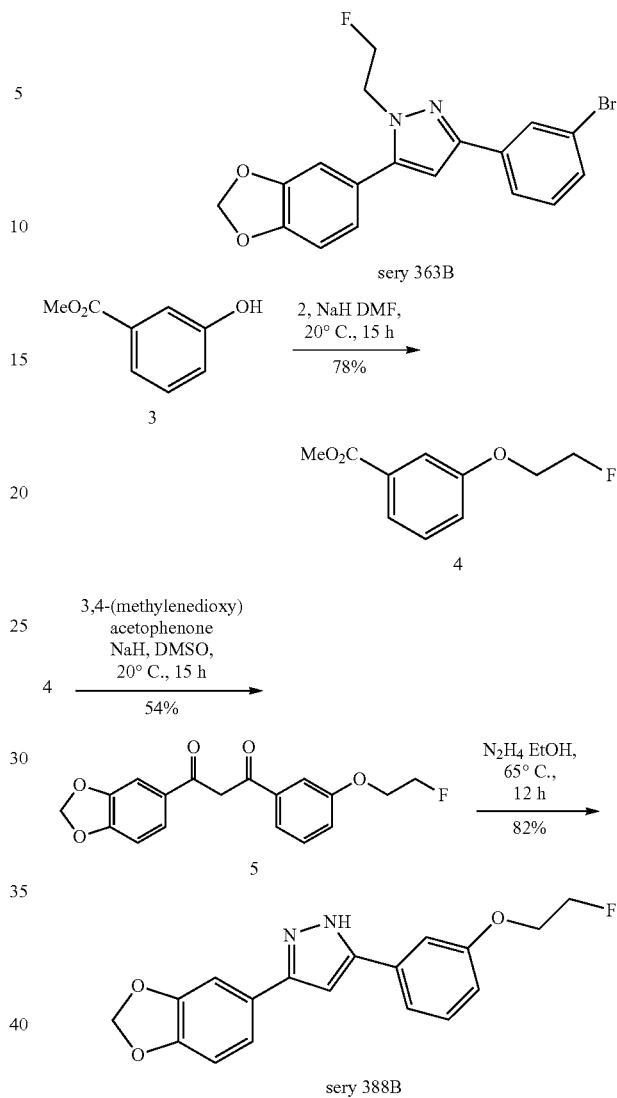

A further useful positron emitter $^{11}$C (half-life 20.38 min) can be introduced via [$^{11}$C]methyl iodide (J. Eriksson et al., J. Label. Compd. Radiopharm. 2006, 49, 1177-1186) with the same type of nucleophilic substitution. Non-radioactive methyl iodide was used for the synthesis of non-radioactive sery 392A, and sery 392B according to scheme B. The same conditions can be used for the synthesis of radioactive analogs of these compounds.

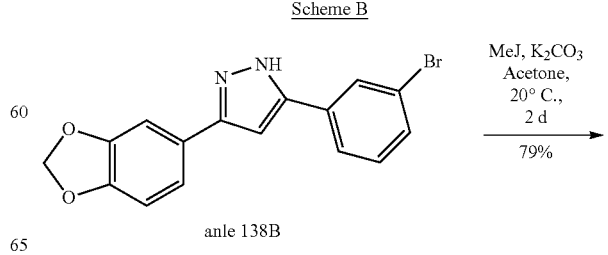

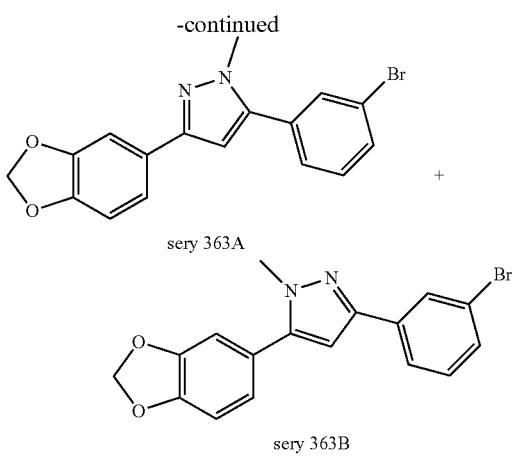

sery 363A sery 363B

Although it is preferred to attach the detectable moiety to the ring D because these compounds are particularly easy to synthesize, this is not essential. It is equally possible to provide compounds of the invention in which the detectable moiety is at a different position in the molecule.

The present invention provides a method of imaging deposits of aggregated protein, which comprises the steps of:
(i) introducing a detectable quantity of a composition comprising a detectably labelled compound of the present invention into a subject;
(ii) allowing sufficient time for the compound to be associated with the aggregated protein; and
(iii) detecting the compound associated with the aggregated protein.

In a preferred embodiment of the method of imaging, the aggregated protein is selected from the group consisting of Amyloid precursor protein (APP) and alpha-synuclein. In a more preferred embodiment, the aggregated protein is alpha-synuclein.

The composition comprising the detectably labelled compound may be introduced into the subject by any of the administrations described above, such as for example orally or parenterally. The labelled compound can be introduced into a patient and after a time span sufficient for the compound to become associated with the aggregated protein, the labelled compound is detected noninvasively inside the patient. Alternatively, the labeled compound can be introduced into a patient, sufficient time is allowed for the compound to become associated with the aggregated protein, and then a sample of tissue from the patient is taken and the labelled compound is detected in the tissue apart from the patient. A tissue sample can also be removed from a patient before introducing the labelled compound into the tissue sample. After allowing for a sufficient amount of time for the compound to become bound to the aggregated protein, the compound can be detected.

Methods for the detection of the labelled compound associated with the aggregated protein are well known in the art and include, without being limiting, magnetic resonance imaging (MRI), positron emission tomography (PET), or single photon emission computed tomography (SPECT) for the detection of radiolabelled compounds. The label that is introduced into the compound depends on the detection method to be used. Thus, for example, if PET is selected as a detection method, the compound must possess a positron-emitting atom, such as $^{11}C$ or $^{18}F$.

The imaging of aggregated proteins can also be carried out quantitatively so that the amount of aggregated protein can be determined.

In a preferred embodiment of the invention, said disease linked to protein aggregation is characterized by the presence of aggregated forms of at least one protein or a fragment or derivative thereof, wherein this protein is selected from the group consisting of prion protein, Amyloid precursor protein (APP), alpha-synuclein, superoxide dismutase, tau, immunoglobulin, Amyloid-A, transthyretin, Beta2-microglobulin, cystatin C, Apolipoproteine A1, TDP-43, Islet amyloid polypeptide, ANF, gelsolin, insulin, lysozyme, fibrinogen, huntingtin and ataxin and other proteins with a Poly-Q stretch. In a preferred embodiment, the protein is selected from the group consisting of Amyloid precursor protein (APP) and alpha-synuclein. In a more preferred embodiment, the protein is alpha-synuclein.

Preferably, said proteins with a Poly-Q stretch are proteins which have at least 36 consecutive glutamine residues. More preferably, said proteins with Poly-Q stretch are selected from the group consisting of huntingtin and ataxin.

It is known to the skilled person that said proteins may exist in various isoforms including proteins modified by phosphorylation, glycosylation, proteolytic processing and the like. The term "at least one . . ." refers to the fact known to the skilled person that diseases can be linked to the presence of more than one protein in the aggregated form. For example, in Alzheimer's disease aggregates of fragments of amyloid precursor protein (APP) and aggregates of tau are usually detectable.

As used herein, the term "neurodegenerative diseases" comprises diseases such as Parkinson's disease, prion disease, Alzheimer's disease, multiple system atrophy, Diffuse Lewy body disease, frontotemporal dementia, amyotrophic lateral sclerosis, Huntington disease, spinocerebellar ataxias and other Poly-Q diseases, hereditary cerebral amyloid angiopathy, familial amyloid polyneuropathy. Moreover, as used herein, the term "protein aggregation disease" refers to diseases manifested predominantly outside the nervous system and includes diseases such as primary systemic amyloidosis (AL amyloidosis), reactive systemic amyloidosis (AA amyloidosis), type II diabetes, injection-localized amyloidosis, beta-2 microglobulin amyloidosis, hereditary non-neuropathic amyloidosis and finnish hereditary systemic amyloidosis.

In another preferred embodiment of the invention, the disease is selected from the group consisting of Parkinson's disease, prion disease, Alzheimer's disease, multiple system atrophy, Diffuse Lewy body disease, frontotemporal dementia, amyotrophic lateral sclerosis, Huntington disease's, spinocerebellar ataxias and other Poly-Q diseases, hereditary cerebral amyloid angiopathy, familial amyloid polyneuropathy, primary systemic amyloidosis (AL amyloidosis), reactive systemic amyloidosis (AA amyloidosis), type II diabetes, injection-localized amyloidosis, beta-2 microglobulin amyloidosis, hereditary non-neuropathic amyloidosis, Finnish hereditary systemic amyloidosis. In a more preferred embodiment, the disease is Parkinson's disease.

In a preferred embodiment of the invention, said prion disease is selected from Creutzfeldt-Jakob disease, variant Creutzfeldt-Jakob disease, genetic human prion disease, Bovine Spongiform Encephalopathy (BSE) and Scrapie.

Finally, the present invention relates to a kit comprising the compound as defined in the present invention and, in addition, an antibody or antibody fragment specifically binding to said compound; and/or monomeric or aggregated protein as defined in the present invention; and/or monomeric or aggregated protein as defined in the present invention, optionally complexed with said compound and instructions for use, in one or more container.

GENERAL EXPERIMENTAL PROCEDURES

The compounds of the present invention can be prepared by any of the applicable techniques of organic synthesis. Many such techniques are elaborated in L. F. Tietze, Th. Eicher "Reaktionen und Synthesen", 2. Auflage (Georg Thieme Verlag, Stuttgart, N Y, 1991), T. W. Greene, P. G. M. Wuts "Protective Groups in Organic Synthesis", Third Edition (John Wiley & Sons, N Y, 1999), as well as J. March "Advanced Organic Chemistry", Third Edition (John Wiley & Sons, N Y, 1985).

A number of exemplary methods for the preparation of the compounds of the invention are provided below. These methods are intended to illustrate the nature of such preparations and are not intended to limit the scope of applicable methods.

Generally, the reaction connotations such as temperature, reaction time, solvents, workup procedures, and the like, will be those common in the art for the particular reaction to be performed. The cited reference material, together with the material cited therein, contains detailed descriptions of such conditions. Typically the temperatures will be −80° C. to 150° C., solvents will be aprotic or protic, and reaction times will be 10 seconds to 10 days. Workup typically consists of quenching any unreacted reagents followed by partition between a water/organic layer system (extraction) and separating the layer containing the product.

Standard synthetic techniques such as use of anhydrous reaction conditions (e.g., inert gas environments) are common in the art and will be applied, when applicable.

Modifications of each of the below schemes leads to various analogs of the specific exemplary materials produced below. The citations given below describing suitable methods of organic synthesis are applicable to such modifications.

In each of the below exemplary schemes it may be advantageous to separate reaction products from one another and/or from starting materials. The desired products of each step are separated and/or purified (hereinafter separated) to the desired degree of homogeneity by the techniques common in the art. Typically such separations involve multiphase extractions, crystallisation from a solvent or solvent mixture, distillation, sublimation, or chromatography. Chromatography can involve any number of methods including, for example, size exclusion or ion exchange chromatography, high, medium or low pressure chromatography, small scale and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction, or the like.

Selection of a appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

In particular, the compounds of the present invention can be prepared in an manner which is analogous to procedures which are disclosed, for instance, in M. Ono et al. (Bioorganic & Medicinal Chemistry 16 (2008) 6867-6872), WO 2008/131148, WO 2004/080972, WO 2004/072050, and WO 98/17652. Alternative routes are also exemplified in the example section of the present invention.

The following examples are intended to illustrate the invention. However, they are not be construed as limiting.

EXAMPLES

Example 1: Identification of a Novel Class of Compounds for Inhibiting Protein Aggregation Two subsets of the commercial compound library DIVERSet (ChemBridge Corp., San Diego, Calif., USA), each containing 10,000 compounds, and called DIVERSet 1 and 2 by us, have been screened for inhibitors of prion propagation using the 2D-SIFT anti-prion assay (Bertsch et al. 2005) and a cell culture model of prion disease. In both assays primary hits were obtained by testing compounds at a single concentration and subsequently verified in dilution series. Additionally, cell culture hits were tested using another cell line.

2DSIFT Screening

To test the inhibitory effect of drugs on the association between PrPC and PrPSc in a high-throughput and high-content screening assay, we applied the "Scanning for Intensely Fluorescent Targets" (SIFT-) technique, which utilises an inverted dual color confocal microscope setup with single photon detectors for two colors of fluorescent light. Samples are prepared in 96- or 384-well microtiter plates with cover slide glass bottoms. The assay mixture consists of recombinant mouse PrP (rPrP), the monoclonal antibody (mAb) L42, which does not recognize mouse PrP but human PrP, and PrPSc aggregates prepared from human CJD brain. The rPrP and mAb molecules are labeled with green and red fluorophores, respectively. Binding of several rPrP and mAb molecules to the PrPSc aggregates will result in the formation of ternary complexes exhibiting many red and green attached fluorophores. Such aggregates can be identified and analyzed by the SIFT method, because they simultaneously cause high intensities in both fluorescence channels. The distribution of the red and green fluorescence intensities can be assessed by a two-dimensional fluorescence intensity histogram. Whenever an inhibitor of the association between rPrP and PrPSc is included in the assay, the green fluorescence intensity of the ternary aggregates should decrease. The color distribution of the aggregates in the 2D-histogram will then be shifted towards the "red" sectors of that histogram.

Primary SIFT-Screening of 20 000 Compounds

The above described assay system was applied to two libraries, each containing 10.000 diverse, drug-like compounds (ChemBridge; "DIVERSet1" and "DIVERSet2") in 96-well microtiter plates for a primary screening including negative controls without any additional compounds and positive controls containing 17 μM DOSPA as well as controls without CJD-rods and compounds (serving to check the absence of aggregation in the antibody and rPrP mixture).

The samples containing DOSPA showed reduced SIFT signal in those sectors which monitor signals of aggregates predominantly labelled with green rPrP. This indicates that in these controls less rPrP had bound to CJD prion rods. Because the prion rods are marked by the red antibody labels, their fluorescence still generates SIFT signal in the "red" sectors. Most of the compounds did not influence the distribution of the SIFT signal. But some of the DIVERSet compounds lowered the number of aggregates detected in the "green" sectors. The SIFT curves of these samples are shifted towards the DOSPA controls. Thus, the corresponding compounds can be considered as primary hits for potential anti-prion drugs. Occasionally some technical problems generated artifacts, which obscured an entire measurement of a whole microtiter plate. Apart form this, only about 7% of the undisturbed measurements had to be treated as outliers and were unsuitable for the automated SIFT analysis, mostly because of intrinsic fluorescence of the tested compounds. This rather low percentage of compounds untreatable by the SIFT assay was unexpected and underscores the versatility and robustness of the assay. The identification of problematic measurements and compounds is facilitated by the high-content nature of the SIFT assay data. For each sample several fluorescence parameters are recorded simultaneously, like for instance the mean fluorescence intensities for each color channel. These are displayed together with the sums of the high-intensity events in each sector of the color distribution histogram. Therefore samples with high intrinsic fluorescence can easily be sorted out.

SIFT Primary Hits and Validation by Dilution Series

For a compound to be classified as a primary hit, we analyzed the sum of bins in the "green" sectors 1 to 5 and defined a cut-off value of approximately 50% of the effect of DOSPA compared to the untreated controls as the minimum effect necessary. DIVERSet compounds were assigned scalar SIFT-activity values (tp1_sift) from the SIFT screening data characterizing their inhibitory effect on prion aggregation as described by Bertsch et al. 2005. Activity values smaller than zero reflect no inhibitory effect, whereas values larger than zero reflect an inhibitory effect. Here, values around one indicate an inhibitory effect equally large as that of the positive control measurements on a given plate.

The primary hits were checked for dose-dependent inhibition of PrPC-PrPSc association using duplicate six point dilution series (0.1-100 μM) of each compound in the SIFT assay. Dose-response curves confirmed the concentration dependent inhibitory activity of these compounds. Compared to the effect of 17 μM DOSPA, half-maximal inhibition of binding of rPrP to prion rods was observed at $EC_{50}$ values in the range of 0.3 to 60 μM.

Cell Culture Primary Hits and Validation by Dilution Series

In addition to the SIFT assay, the DIVERSet libraries were also screened in cell culture models of prion diseases. In these assays, the anti-prion activity of DIVERSet compounds was initially tested at a concentration of 20 μM. The results of the primary cell culture screening (on SMB cells at 20 μM) are encoded by a binary variable (tp3_reduktion), where a value of "1.0" encodes "active" and "0.0" encodes "inactive". Active compounds identified in the primary screening were validated, wherein the aim was to identify compounds active even at very low concentrations. The verification of primary cell culture hits was done in dilution series at four concentrations (1 μM, 4 μM, 10 μM, 40 μM) for DIVERSet 1 and only at two concentrations (0.2 μM, 2 μM) for DIVERSet 2. Results (tp3_reduktion_mue) are denoted by "1.0" for active at 1 μM (DS1) or at 0.2 μM (DS2) and by "0.5" for active at 2 μM (DS2). Compounds inactive at concentrations above 20 μM are denoted by "0.0" (DS1+2). Additionally, primary SMB cell culture hits were validated at single concentrations on ScN2a cells (tp3_scn2a), where again "0.0" and "1.0" denote inactive and active compounds, respectively.

Diphenylpyrazoles (DPP) and Related Compounds as New Anti-Prion Compounds

SAR-Map Generation

The DIVERSet compounds characterized as "active" in the primary cell culture screening were subjected to a cluster analysis using the software package Benchware HTS DataMiner (DM; Tripos Inc., St. Louis, Mo., USA) resulting in the SAR-map shown in FIG. 1. As the large number of compounds contained in the two libraries (20.000) is too large as a starting point for cluster analysis using DataMiner, the analysis was initially restricted to the primary hits (837 compounds) of the cell culture screening of DIVERSet 1 and 2. Thus, clusters were determined for the active compounds only. Here, the DM program grouped structurally similar and active compounds into clusters and is thus suitable to identify potentially relevant new lead structures. In a second step, the thus established classification was applied to the rest of the library covering the compounds inactive in cell culture. Here, the DM program added further (inactive) compounds to the generated clusters, if the employed measure indicated a high structural similarity.

The result of the cluster analysis is graphically displayed by DateMiner in form of a SAR-map, in which the substance clusters S are represented by symbols. DM arranges the symbol such that they are located closer together if the represented clusters are structurally similar. Size, form and colour of the symbols is allocated based on cluster-specific properties, that can be selected by the user.

Thus, it was selected that the size of the symbols is proportional to the size of the cluster /S/, i.e. to the number of compounds C contained therein. The form of the symbols was determined based on the fraction $$P_{SIFT}(\mathcal{S}) = \frac{|\{C \in \mathcal{S} | a(C) \geq a_{min}\}|}{|\mathcal{S}|}$$

of those substances C in the corresponding clusters S, whose primary activity a(C) as determined in the SIFT screening was above a selected threshold of $a_{min}$=0.25. Thus, clusters whose fraction $P_{SIFT}(S)$ is above 50% are shown as stars whereas the remaining, mainly non-active clusters are shown as squares. Analogously, the colour of the symbods encodes the fractions of the clusters $$P_{ZK}(\mathcal{S}) = \frac{|\{C \in \mathcal{S} | C^{is\ primary\ hit}\}|}{|\mathcal{S}|}$$

according to the primary hits of the cell culture based screening, wherein the symbols of clusters with more than 50% active substances are red and the remaining clusters are grey. FIG. 1 shows the SAR-map resulting from the above described cluster analysis. Large red stars symbolise clusters with a high proportion of SIFT- and cell culture positive substances. These clusters represent potential lead structures. Using DataMiner, clusters of interest were further analysed and a group of five neighbouring clusters was identified (termed DPP_1 through DPP_5), which are shown in FIG. 1 in bold. All compounds sorted into these clusters are shown in FIG. 2 together with their activities in the various assays. The fact that these clusters are located in close relation with each other indicates that they contain substances that are structurally similar, i.e. all of them belong to the chemical compound class of 3,5-Diphenyl-pyrazole (DPP) derivatives (cf. the DPP motif shown in FIG. 1).

Example 2: Synthesis of New Drugs for Inhibiting Aggregation Under Medicinal-Chemical Aspects Based on the discovery of the new lead structure as described above, a number of further substances were synthesised by selective substitution of different substituents, as outlined below.

Scheme 1: Synthesis of isoxazoles

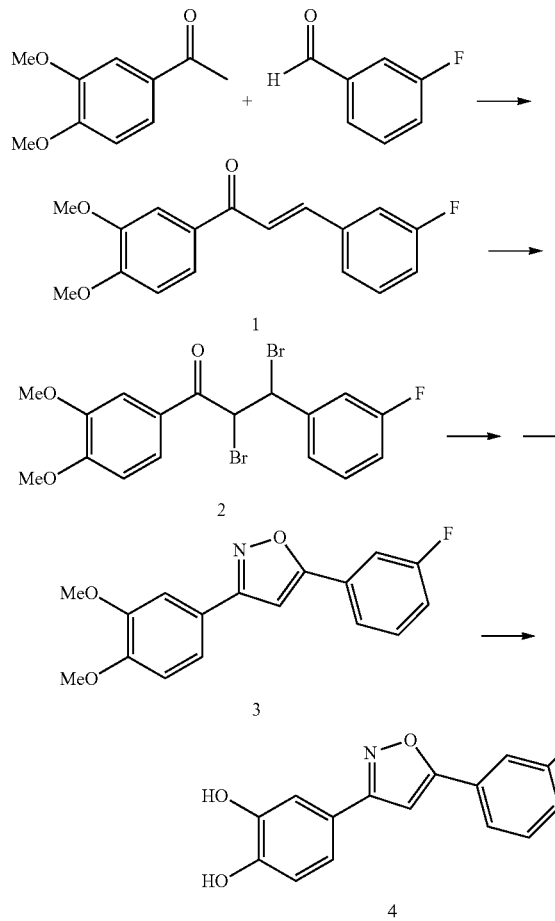

(E)-1-(3,4-Dimethoxyphenyl)-3-(3-fluorophenyl)-2-propene-1-one (1) [Nam et al., 2004]

A solution of 3,4-dimethoxyacetophenone (1.8 g, 10 mmol), 3-fluorobenzadehyde (1.24 g, 10 mmol), NaOH (50 mg, 1.25 mmol) and Ba(OH)$_2$.8H$_2$O (100 mg, 0.32 mmol) in methanol (10 ml) was stirred at room temperature for 24 h. The reaction was cooled to +4° C., resulting precipitate was collected by filtration, recrystallized from methanol and dried to provide 1 (1.65 g, 58%) as a yellow powder.

2,3-Dibromo-1-(3,4-dimethoxyphenyl)-3-(3-fluoro-phenyl)-propan-1-one (2) [Harris et al., 1977]

To a solution of 1 (715 mg, 2.5 mmol) in chloroform (11 ml) was added dropwise a solution of bromine (400 mg, 2.5 mmol) in chloroform (4 ml) at 00° C. After being stirred for 2 h at 00° C. the reaction was diluted with petroleum benzin (20 ml) and the mixture was refrigerated (−24° C.) for 10 hours, resulting precipitate was collected by filtration, washed with n-hexane (10 ml) and dried to provide 2 (780 mg, 70%) as a white powder.

3-(3,4-Dimethoxyphenyl)-5-(3-fluorophenyl)isox-azole (3) [Harris et al., 1977]

A solution of 2 (450 mg, 1 mmol) in ethanol (6 ml) was treated with hydroxylamine hydrochloride (306 mg, 4.4 mmol) followed by a solution of NaOH (460 mg, 11.5 mmol) in water (1.5 ml). The mixture was heated under reflux for 2 h, cooled down and treated with water (3 ml). After refrigeration (4° C.) overnight the product was collected by filtration, washed with water (5 ml) and dried to provide 3 (180 mg, 60%) as a white powder.

3-(3,4-Dihydroxyphenyl)-5-(3-fluorophenyl)isox-azole (4) [Vanelle et al., 2000]

A solution of 3 (100 mg, 0.33 mmol) in dichloromethane (5 ml) was cooled down to −78° C., treated with boron tribromide (0.16 ml, 1.7 mmol), stirred at −78° C. for 3 h and then overnight at room temperature. The mixture was cooled down to −78° C. and quenched with methanol (5 ml). After stirring for 3 h at room temperature solvents were evaporated under reduced pressure, the residue was co-evaporated four times with methanol (10 ml). The resulting precipitate was refluxed in 5 ml chloroform, after cooling the product was collected by filtration and dried to provide 4 (60 mg, 67%) as a white powder.

Scheme 2: Synthesis of pyrazoles

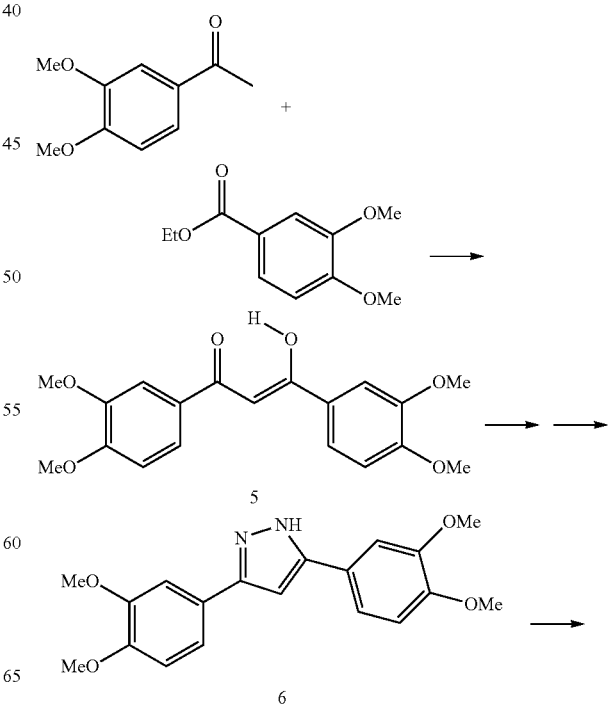

-continued

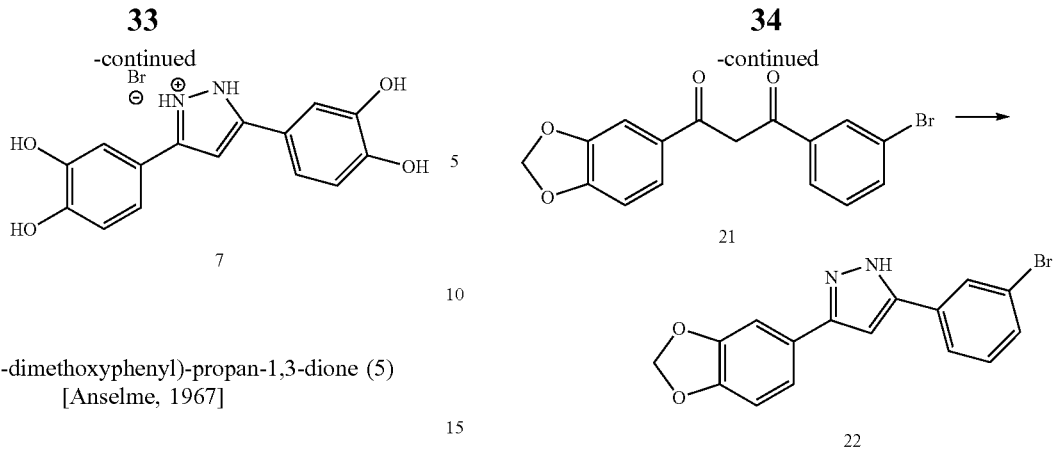

1-(1,3-Benzodioxol-5-yl)-3-(3-bromophenyl)-propan-1,3-dione (21) [Anselme, 1967]

1. Procedure

A dry, 500-mL, three-necked flask is fitted with a Teflon®-coated magnetic stirring bar, a rubber septum, a thermometer, and a reflux condenser to which is attached a T-tube connected to a source of pure nitrogen. The remaining joint of the T-tube is connected to a bubbling device so that the rate of nitrogen flow can be observed throughout of the reaction. The apparatus is arranged so that the flask may be cooled intermittently with a water bath. After the reaction vessel has been flushed with nitrogen a static nitrogen atmosphere is maintained in the reaction vessel for the remainder of the reaction. The flask is charged with ca. 60% dispersion of sodium hydride (5 g, 0.125 mole) in mineral oil (Note 1). The mineral oil is washed from the hydride with petroleum benzine 40/60 (3×40 mL) (Note 2). The supernatant petroleum benzine layer is removed using a Luer-lock hypodermic syringe with a stainless-steel needle inserted through the rubber septum. The residual sodium hydride is mixed with 80 mL of dimethyl sulfoxide (Note 3), and the rubber septum is replaced with a pressure-equalizing dropping funnel. A solution of 16.4 g (0.1 mole) of 1-(1,3-benzodioxol-5-yl)ethanone (Note 4) and 26.9 g (0.125 mole) of methyl 3-bromobenzoate (Note 5) in 60 mL of dimethyl sulfoxide is placed in the dropping funnel. The funnel is stoppered, stirring is begun and the contents of the flask are cooled in a water bath to 15° C. The solution of 1-(1,3-benzodioxol-5-yl)ethanone and methyl 3-bromobenzoate is added slowly so that hydrogen evolution is maintained at the controllable rate and the temperature did not rise above 20° C. over a period of 60 minutes (Note 6). After the addition is completed, the bath is removed, and the reaction mixture is stirred at room temperature (23° C.) for 15 hours. The resulting red-brown homogeneous reaction mixture is poured slowly into 500 mL of an ice and water containing 5 mL of 85% orthophosphoric acid (Note 7) with stirring. After 1 hour stirring the product is removed by filtration (Note 8), washed by suction filtration with water (2×100 mL), and vacuum dried to constant weight at 40° C. for 6 hours to give 34.4 g of the crude (Note 9) product. Recrystallization from 200 mL of 99.9% ethanol and 200 mL ethyl acetate (Note 10) and drying in vacuum to constant weight at 40° C. for 6 hours gives 28.5 g (82% yield) of pure (Note 11) 1-(1,3-benzodioxol-5-yl)-3-(3-bromophenyl)propane-1,3-dione, m.p. 136-137° C. The filtrate is concentrated under reduced pressure to a volume ca. 30 mL, the crystalline solid that separates is collected on a filter, washed by suction 1,3-Bis(3,4-dimethoxyphenyl)-propan-1,3-dione (5) [Anselme, 1967]

A 60% suspension of sodium hydride in mineral oil (0.4 g, 10 mmol) was washed with petroleum benzin (20 ml) two times, anhydrous DMSO (10 ml) was added. After being stirred for 30 min at room temperature under argon, THF (5 ml) was added, the flask was cooled down to 15° C. and ethyl 3,4-dimethoxybenzoate (2.1 g, 10 mmol) was added. The temperature was allowed to drop to 10° C. and a solution of 3,4-dimethoxyacetophenone (1.08 g, 6 mmol) in DMSO (4 ml) was added at such a rate that the temperature didn't rise above 15° C. Upon completion of addition the reaction mixture was stirred 72 h at room temperature, then poured slowly into crushed ice (250 g) containing 85% phosphoric acid (1 ml). Resulting precipitate was collected by filtration, washed with water (50 ml) and dried to provide 5 (2.1 g, 99%) as a yellow powder.

3,5-Bis(3,4-dimethoxyphenyl)pyrazole (6) [Hauser et al., 1957]

A solution of 5 (1.0 g, 2.9 mmol) and hydrazine hydrate (218 mg, 4.4 mmol) in ethanol (15 ml) was heated under reflux 3 h with stirring. The clear yellow solution was evaporated under reduced pressure, water was added and resulting precipitate was collected by filtration, washed with water and dried to provide 6 (960 mg, 97%) as a yellow powder.

3,5-Bis(3,4-dihydroxyphenyl)pyrazole hydrobromide (7) [Vanelle et al., 2000]

A solution of 6 (120 mg, 0.35 mmol) in dichloromethane (5 ml) was cooled down to −78° C., treated with boron tribromide (0.34 ml, 3.5 mmol), stirred at −78° C. for 3 h and then overnight at room temperature. The mixture was cooled down to −78° C. and quenched with methanol (5 ml). After stirring for 3 h at room temperature solvents were evaporated under reduced pressure, the residue was co-evaporated four times with methanol (10 ml). The resulting precipitate was reflux in 5 ml chloroform, after cooling the product was collected by filtration and dried to provide 7 (108 mg, 85%) as a yellow powder.

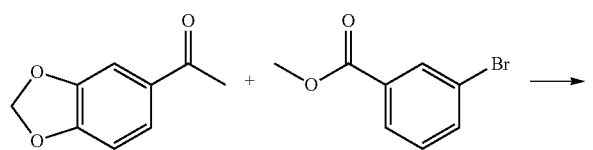

filtration with ethanol (2×10 mL) and vacuum dried to constant weight at 40° C. for 6 hours, yielding an additional crop (3.15 g) of the crude product. The crude product is recrystallized twice from 20 mL of 99.9% ethanol and 20 mL ethyl acetate and vacuum dried to constant weight at 40° C. for 6 hours to afford additional 1.8 g (5% yield) of pure 1-(1,3-benzodioxol-5-yl)-3-(3-bromophenyl)propane-1,3-dione (Note 12). The total yield of the product is 30.3 g (87%).

2. Notes
1. Sodium hydride, 57-63% oil dispersion, order number 13431 available from Alfa Aesar GmbH & Co KG, Karlsruhe was used.
2. Petroleum benzine GR for analysis boiling range 40-60° C., order number 101775 from Merck KGaA, Darmstadt was used.
3. The dimethyl sulfoxide GR for analysis, order number 102952 from Merck KGaA, Darmstadt was used without further purification.
4. 1-(1,3-Benzodioxol-5-yl)ethanone, 98%, order number A13597 available from Alfa Aesar GmbH & Co KG, Karlsruhe was used.
5. Methyl 3-bromobenzoate, 98%+, order number A16174 available from Alfa Aesar GmbH & Co KG, Karlsruhe was used.
6. A foaming is observed during the addition of the solution. The usage of mechanical stirrer and an antifoaming agent like polyethylene glycol dimethyl ether may be necessary at the upscaling.
7. The orthophosphoric acid, 85% w/w aq. solution, GR for analysis, order number 100573 from Merck KGaA, Darmstadt was used.
8. The pH-value of the reaction mixture is pH=7. By acidification with additionally 15 mL ortophosphoric acid to pH=2, 1.3 g of 3-bromobenzoic acid may be obtained.
9. Purity of the product determined by HPLC is 96.3%.
10. The ethanol 99.9% absolute GR for analysis, order number 100983, and ethyl acetate GR for analysis, order number 109623 available from Merck KGaA, Darmstadt was used.
11. Purity of the product determined by HPLC is 99.3%. Analytical HPLC is performed by using a Waters HPLC system with a Waters 996 Photodiode Array Detector. All separations involved a mobile phase of 0.1% v/v trifluoroacetic acid (TFA) in water (solvent A) and 0.1% v/v TFA in acetonitrile (solvent B) by using a reversed phase (RP) column Eurospher RP 18, 100 Å, 5 μm, 250×4.6 mm at flow rates of 1 mL/min. The compound is dissolved in acetonitrile GR for HPLC at a concentration 1 mg/mL. Peaks with retention times (RT) 20.9 and 10.3 min are enol and keto forms respectively of the ANLE 138A. Reinjection of separately collected peaks 20.9 or 10.3 min gives again the same two peaks with identical RTs.
12. Purity of the product determined by HPLC is 98.4%.

3-(1,3-Benzodioxol-5-yl)-5-(3-bromophenyl)-1H-pyrazole (22) [Hauser et al., 1957]

1. Procedure

A mixture of 28.4 g (81.8 mmole) of 1-(1,3-benzodioxol-5-yl)-3-(3-bromophenyl)propane-1,3-dione (Note 1) and 200 mL of n-butyl alcohol (Note 2) is placed in a 500-mL round-bottomed flask fitted with a Teflon®-coated magnetic stirring bar, a reflux condenser, and an electrical heating mantle. Stirring and heating is started, 6 mL (6.2 g, 123.4 mmole) of hydrazine monohydrate (Note 3) is added upon dissolution of the solid, and the reaction mixture is heated under reflux with stirring for 4 hours. The reaction mixture is cooled down to 20° C., stored 1 hour at 0° C., and the product that separates is collected by suction filtration. Washing with water (100 mL) and drying in vacuum to constant weight at 40° C. for 36 hours gives 26.8 g (95% yield) of 3-(1,3-benzodioxol-5-yl-5-(3-bromophenyl)-1H-pyrazole (Note 4) m. p. 195-197° C.

2. Notes
1. The 1-(1,3-benzodioxol-5-yl)-3-(3-bromophenyl)propane-1,3-dione is prepared according to protocol for ANLE 138A.
2. The n-butyl alcohol 99.4% GR "Baker analyzed", order number 8017 available from J. T. Baker B. V., Deventer, Holland was used.
3. The hydrazine monohydrate GR purum, order number 53850 available from Sigma-Aldrich Chemie GmbH, Taufkirchen was used.
4. Purity of the product determined by HPLC is 99.3%. Analytical HPLC is performed by using a Waters HPLC system with a Waters 996 Photodiode Array Detector. All separations involved a mobile phase of 0.1% v/v trifluoroacetic acid (TFA) in water (solvent A) and 0.1% v/v TFA in acetonitrile (solvent B) by using a reversed phase (RP) column Eurospher RP 18, 100 Å, 5 μm, 250×4.6 mm at flow rates of 1 mL/min. The compound is dissolved in acetonitrile GR for HPLC at a concentration 1 mg/mL.

Scheme 3: Synthesis of imidazoles

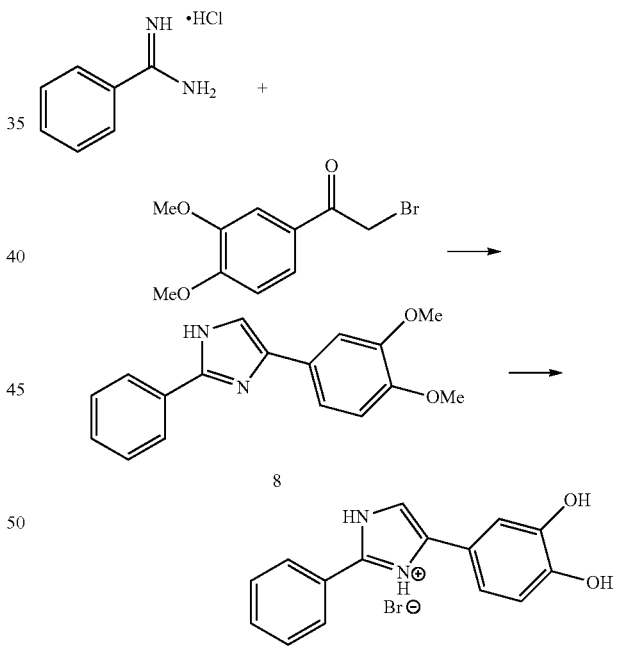

4-(3,4-Dimethoxyphenyl)-2-phenylimidazole (8) [Li et al., 2000]

A mixture of benzamidine hydrochloride (313 mg, 2 mmol) and sodium bicarbonate (672 mg, 8 mmol) in THF (6 ml) and water (1.5 ml) was heated under reflux. A solution of α-bromo-3,4-dimethoxyacetophenone (518 mg, 2 mmol) in THF (1.5 ml) was added over a period of 30 min, while keeping the reaction under reflux. After addition, the reaction was heated under reflux for 2 h, THF was evaporated under reduced pressure. Ethyl acetate (20 ml) was added to the mixture, organic phase was separated, washed with the brine (5 ml), dried with sodium sulfate and evaporated under reduced pressure. The resulting crude product was purified by column chromatography on silica gel (chloroform/methanol 100:1) to provide 8 (470 mg, 84%) as a solid.

4-(3,4-Dihydroxyphenyl)-2-phenylimidazole hydrobromide (9) [Vanelle et al., 2000]

A solution of 8 (190 mg, 0.68 mmol) in dichloromethane (5 ml) was cooled down to −78° C., treated with boron tribromide (0.32 ml, 3.4 mmol), stirred at −78° C. for 3 h and then overnight at room temperature. The mixture was cooled down to −78° C. and quenched with methanol (5 ml). After stirring for 3 h at room temperature solvents were evaporated under reduced pressure, the residue was co-evaporated four times with methanol (10 ml). The resulting precipitate was reflux in 5 ml chloroform, after cooling the product was collected by filtration and dried to provide 9 (192 mg, 85%) as a powder.

Scheme 4: Synthesis of pyrroles

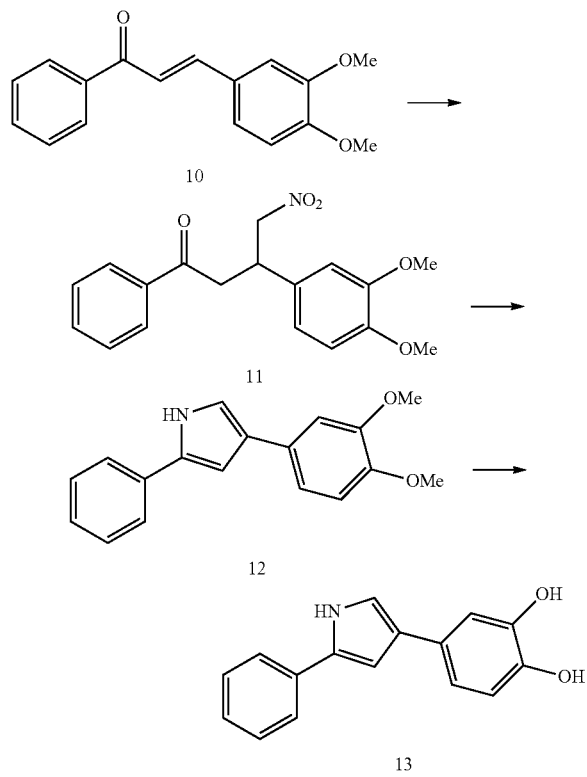

(E)-1-Phenyl-3-(3,4-dimethoxyphenyl)-2-propene-1-one (10)

Compound 10 was prepared according to the procedure described the preparation of 1. Yield 90%.

3-(3,4-Dimethoxyphenyl)-4-nitro-1-phenylbutan-1-one (11) [Hall et al., 2005]

A solution of 10 (774 mg, 2.9 mmol) in MeOH (30 ml) was treated with diethylamine (1.55 ml, 15 mmol) and nitromethane (0.81 ml, 15 mmol) and heated under reflux for 24 h. The solution was cooled down, partitioned between dichloromethane (60 ml) and water (50 ml) and acidified with 1 M hydrochloric acid. The organic layer was separated, the aqueous layer was extracted with dichloromethane (20 ml). The combined organic layers were washed with water (50 ml) and brine (50 ml) and dried with sodium sulfate. The solvent was removed under reduced pressure, and the resulting oil was purified by column chromatography on silica gel (n-hexane/ethyl acetate 3:2) to provide 11 (780 mg, 82%) as a solid.

4-(3,4-Dimethoxyphenyl)-1-phenylpyrrole (12) [Hall et al., 2005]

A stirred solution of 11 (400 mg, 1.22 mmol) in methanol (13 ml) and THF (26 ml) at room temperature was treated with potassium hydroxide (343 mg, 6.1 mmol). After 1 h the reaction mixture was added dropwise to a solution of sulfuric acid (2.44 ml) in methanol (13 ml) at 0° C. and stirred 1 h at room temperature. Water (20 ml) and ice (20 ml) were added, and the mixture was neutralized with aqueous 1 M sodium hydroxide and extracted with dichloromethane (2×50 ml). Combined organic fractions were washed with brine (25 ml), dried over sodium sulfate and evaporated under reduced pressure. The resulting oil was treated with acetic acid (8 ml) and ammonium chloride (470 mg), the solution was heated at 100° C. for 1 h. The reaction mixture was cooled down, ice (50 ml) was added, and the mixture was neutralized with aqueous 1 M sodium hydroxide. The solution was extracted with dichloromethane (2×50 ml). Combined organic fractions were washed with brine (25 ml), dried over sodium sulfate and evaporated under reduced pressure. The crude product was purified by column chromatography on silica gel (n-hexane/ethyl acetate 3:1) and then recrystallized from a mixture n-hexane/ethyl acetate (2:1) to provide 12 (150 mg, 44%) as a solid.

4-(3,4-Dihydroxyphenyl)-1-phenylpyrrole (13) [Vanelle et al., 2000]

A solution of 12 (80 mg, 0.29 mmol) in dichloromethane (5 ml) was cooled down to −78° C., treated with boron tribromide (0.13 ml, 1.4 mmol), stirred at −78° C. for 3 h and then overnight at room temperature. The mixture was cooled down to −78° C. and quenched with methanol (5 ml). After stirring for 3 h at room temperature solvents were evaporated under reduced pressure, the residue was co-evaporated four times with methanol (10 ml). The resulting crude product was purified by column chromatography on silica gel (chloroform/methanol 95:5) and then recrystallized from chloroform with a few drops of acetonitril to provide 13 (36 mg, 50%) as a solid.

Scheme 5: Synthesis of pyrazolines

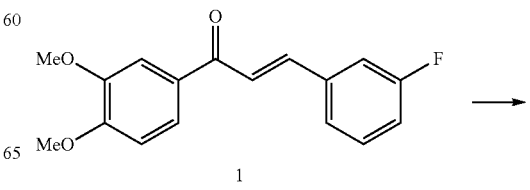

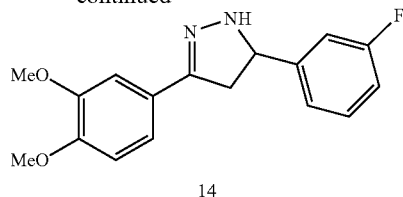

3-(3,4-Dimethoxyphenyl)-5-(3-fluorophenyl)-4,5-dihydro-1H-pyrazole (14)

A suspension of 1 (57 mg, 0.2 mmol) and hydrazine hydrate (0.5 ml, 10 mmol) in water (0.14 ml) was heated at 100° C. for 1.5 h with stirring. The reaction mixture was cooled down, water (0.2 ml) was added and resulting precipitate was collected by filtration, washed with water and dried to provide 14 (37 mg, 62%) as a white solid.

Scheme 6: Synthesis of N-Ac-pyrazolines

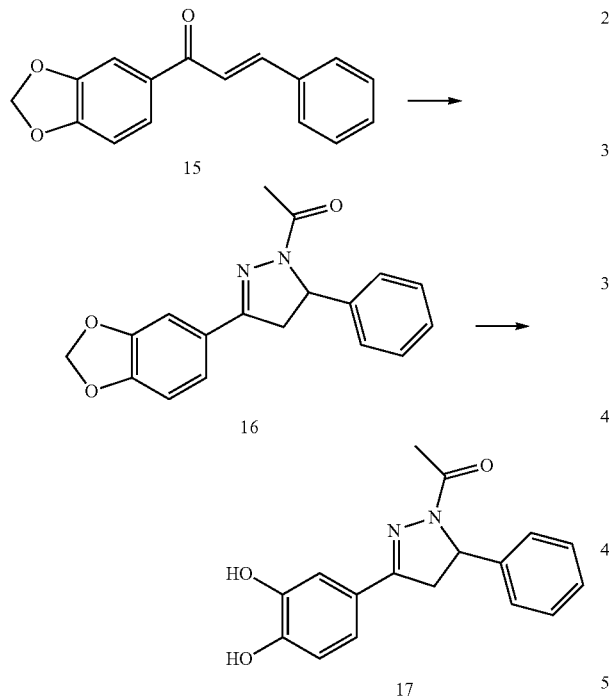

(E)-1-(3,4-Methylenedioxyphenyl)-3-phenyl-2-propene-1-one (15)

Compound 15 was prepared according to the procedure described the preparation of 1. Yield 64%.

1-Acetyl-3-(3,4-methylenedioxyphenyl)-5-phenyl-4,5-dihydropyrazole (16) [Chimenti et al., 2004]

A solution of 15 (504 mg, 2 mmol) and hydrazine hydrate (250 mg, 5 mmol) in acetic acid (12 ml) was heated at 120° C. for 24 h with stirring. The reaction mixture was cooled down, cold water (40 ml) was added and resulting precipitate was collected by filtration, recrystallized from ethanol and dried to provide 16 (458 mg, 74%) as a white solid.

1-Acetyl-3-(3,4-dihydroxyphenyl)-5-phenyl-4,5-dihydropyrazole (17) [Vanelle et al., 2000]

A solution of 17 (70 mg, 0.23 mmol) in dichloromethane (3 ml) was cooled down to −78° C., treated with boron tribromide (0.11 ml, 1.16 mmol), stirred at −78° C. for 3 h and then overnight at room temperature. The mixture was cooled down to −78° C. and quenched with methanol (5 ml). After stirring for 3 h at room temperature solvents were evaporated under reduced pressure, the residue was co-evaporated four times with methanol (10 ml). The resulting crude product was purified by column chromatography on silica gel (n-hexane/ethyl acetate 1:1) to provide 17 (25 mg, 37%) as a solid.

Scheme 7: Synthesis of 1,2,4-oxadiazoles

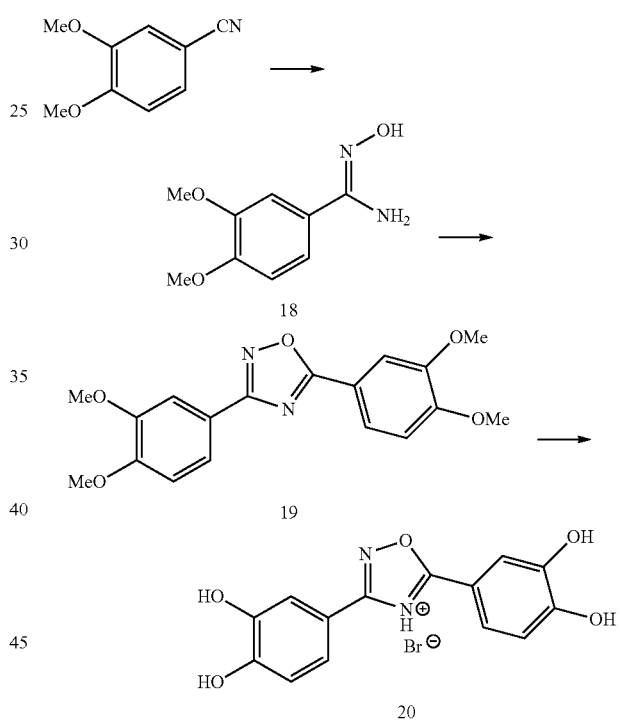

3,4-Dimethoxybenzamidoxime (18) [Chalquest, 2001]

A solution of 3,4-dimethoxybenzonitrile (4.0 g, 24.5 mmol), hydroxylamine hydrochloride (2.0 g, 28.8 mmol), N,N-diisopropylethylamine (5.0 ml, 29.2 mmol) in ethanol (70 ml) was stirred at room temperature for 48 h. Ethanol was evaporated under reduced pressure, cold water (60 ml) was added and resulting precipitate was collected by filtration and dried to provide 18 (3.4 g, 71%) as a white powder.

3,5-Bis(3,4-dimethoxyphenyl)-1,2,4-oxadiazole (19) [Korbonits, 1982]

To a solution of 18 (700 mg, 3.57 mmol) and ethyl 3,4-dimethoxybenzoate (834 mg, 3.97 mmol) in ethanol (12 ml) potassium tert-butoxide (425 mg, 3.79 mmol) was added and reaction mixture was heated under reflux for 12 h. The mixture was cooled down and precipitate was collected by filtration, washed with hot ethanol and dried to provide 19 (540 mg, 44%) as a white powder.

3,5-Bis(3,4-dihydroxyphenyl)-1,2,4-oxadiazole hydrobromide (20) [Vanelle et al., 2000]

A solution of 19 (220 mg, 0.64 mmol) in dichloromethane (6 ml) was cooled down to −78° C., treated with boron tribromide (0.59 ml, 6.1 mmol), stirred at −78° C. for 3 h and then overnight at room temperature. The mixture was cooled down to −78° C. and quenched with methanol (5 ml). After stirring for 3 h at room temperature solvents were evaporated under reduced pressure, the residue was co-evaporated four times with methanol (10 ml). The resulting precipitate was reflux in 5 ml chloroform, after cooling the product was collected by filtration and dried to provide 20 (190 mg, 81%) as a powder.

Figure 3:
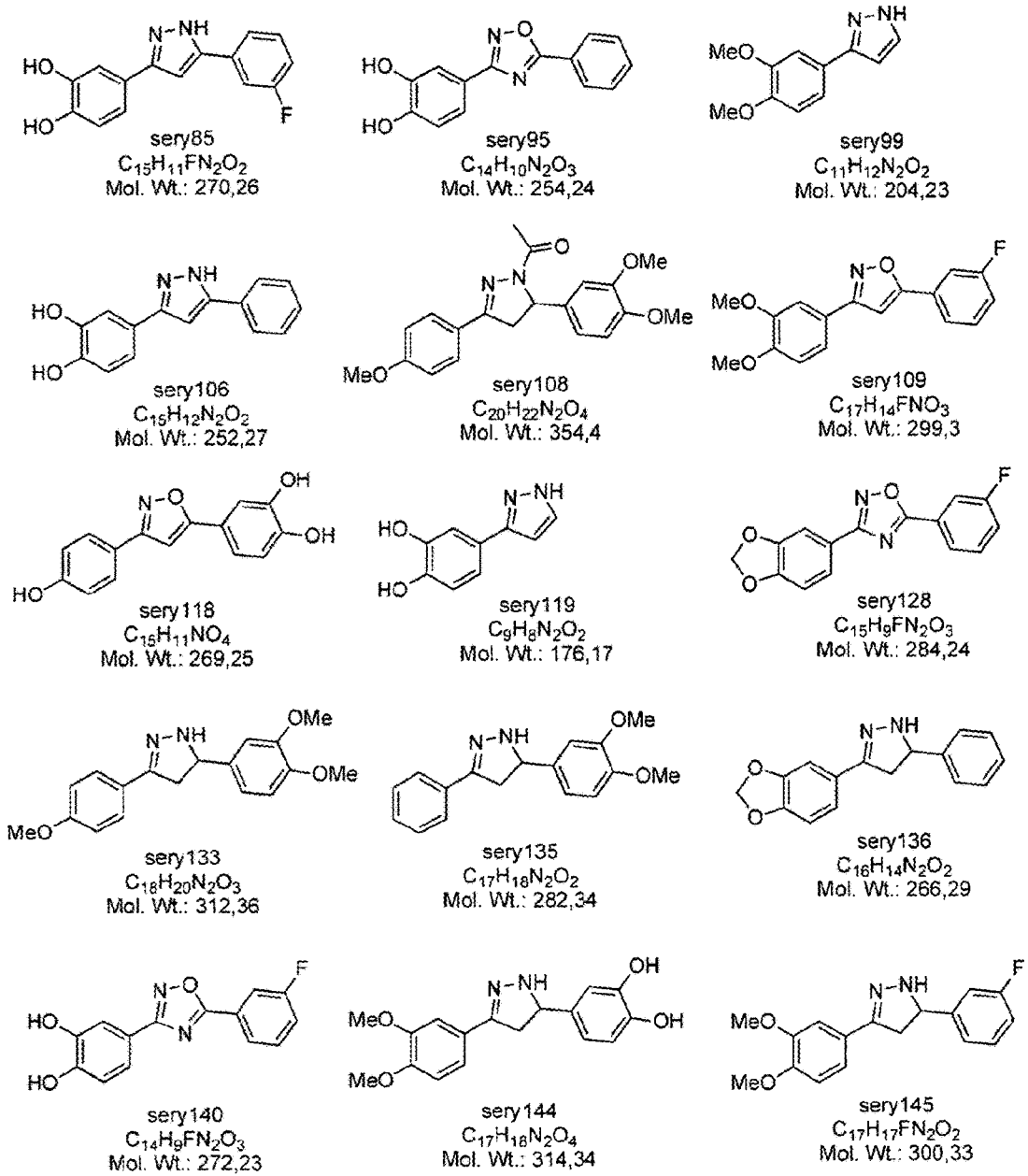
FIG. 3: List of compounds that were synthesized according to the methods described in example 2 based on the results of the initial screening and medicinal chemical considerations. These compounds were analysed using various test assays (i.e. SIFT, assays in cell culture models of prion diseases, in vivo animal tests or biochemical assays of α-synuclein aggregation).
Figure 3:
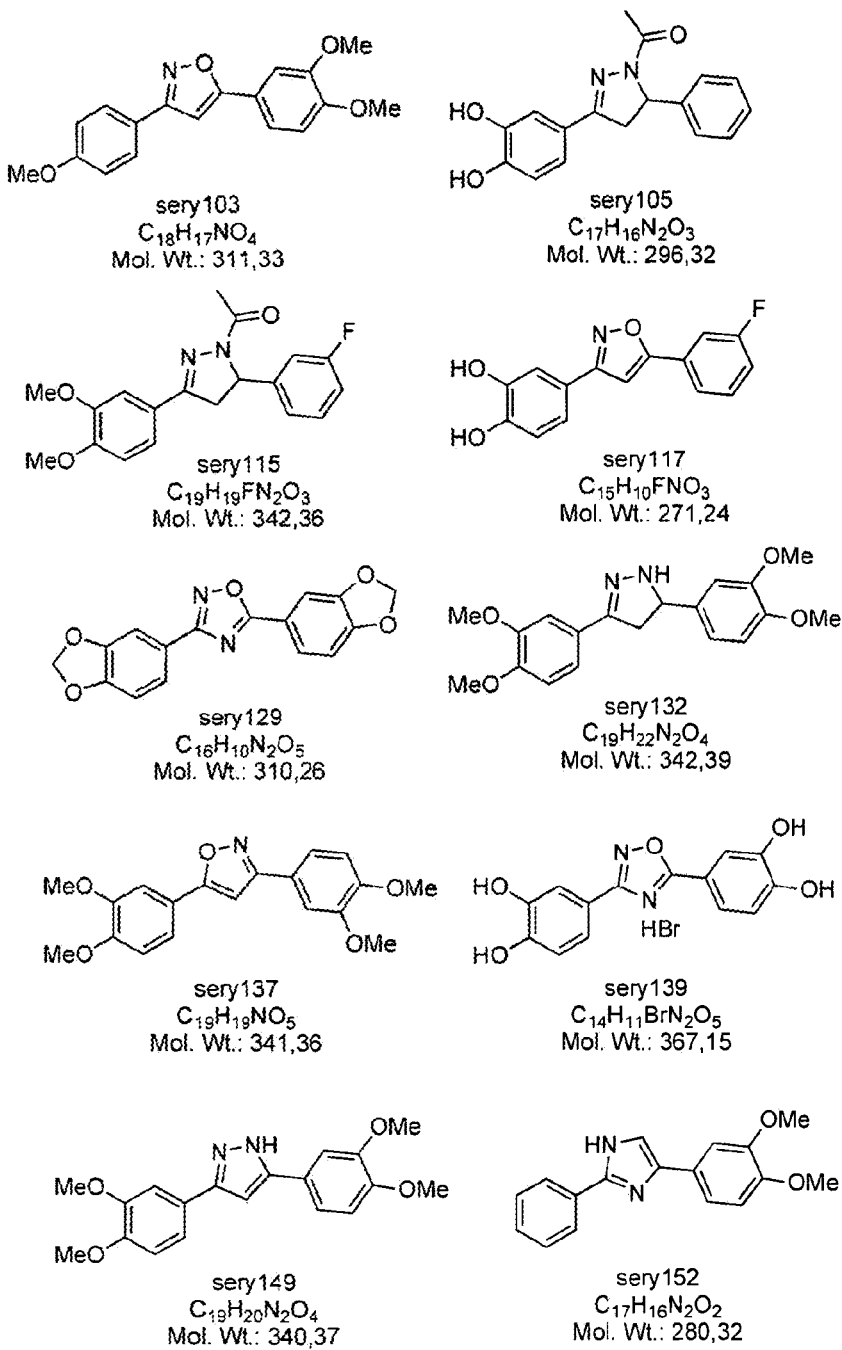
Figure 3:
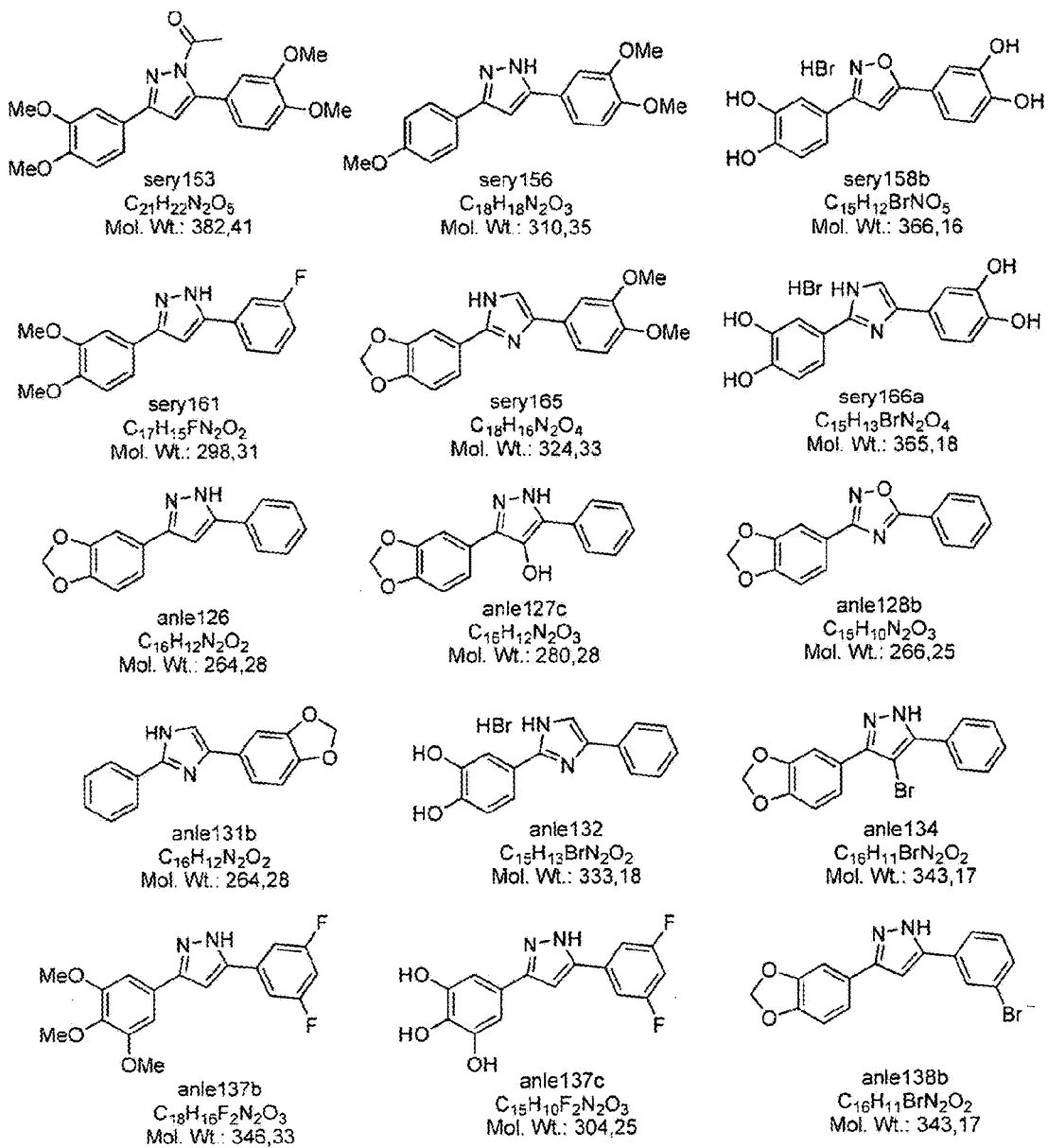
Figure 3:
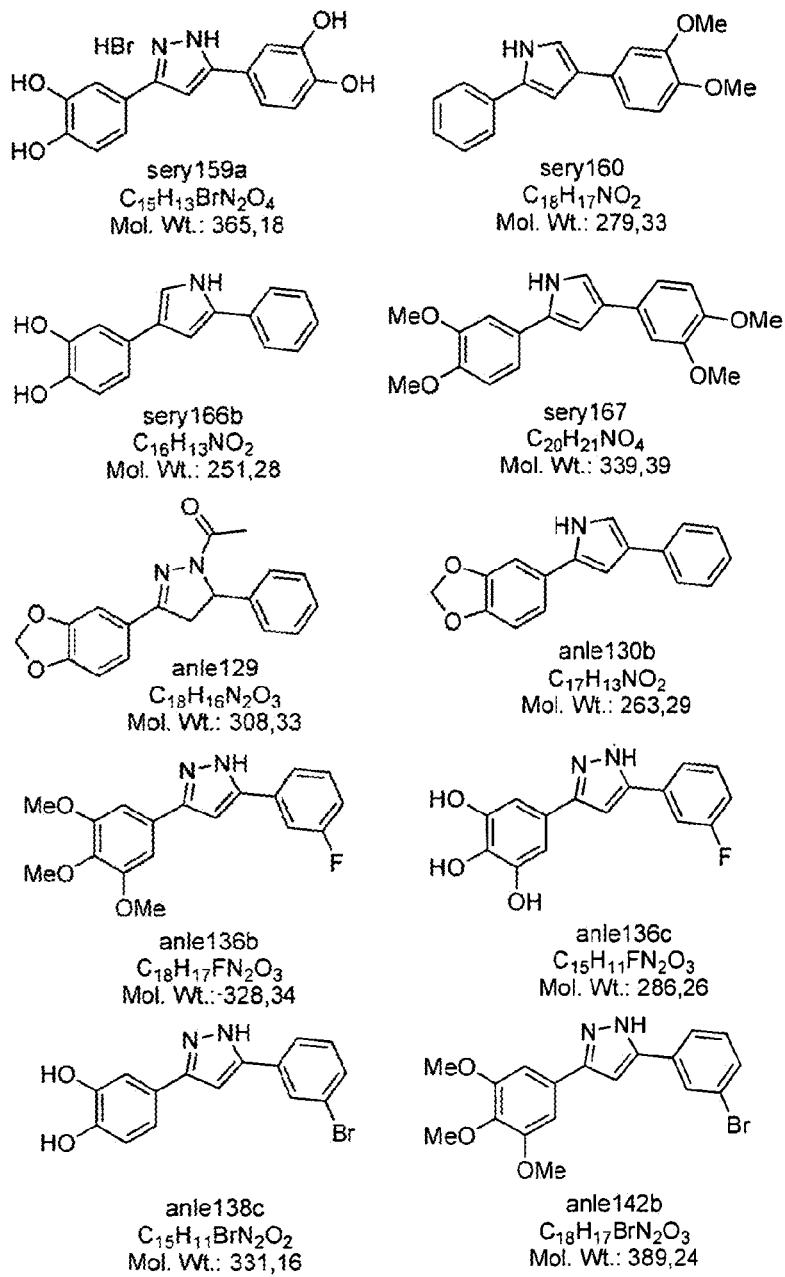
Figure 3:
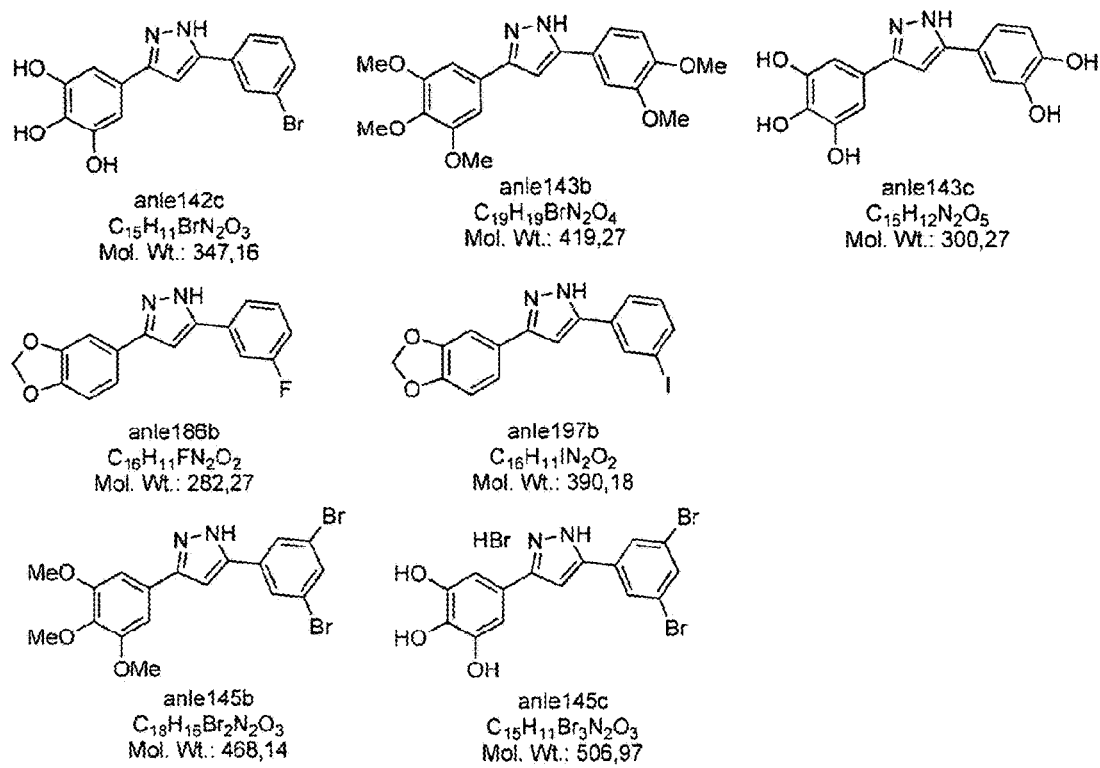
Figure 3:
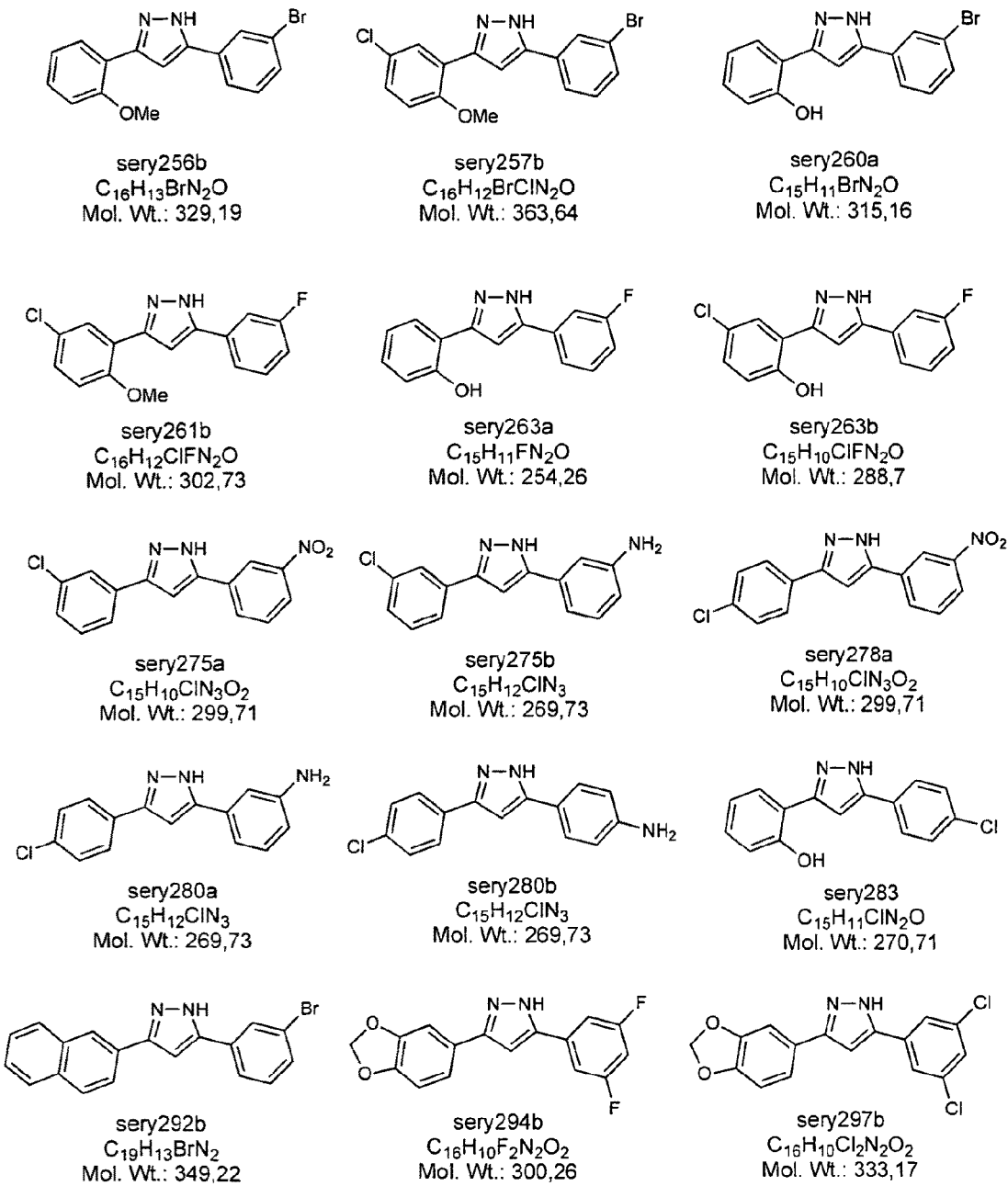
Figure 3:
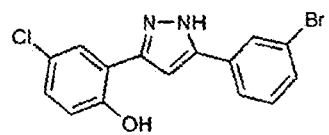
Figure 3:
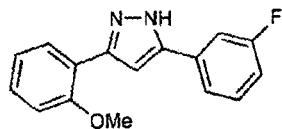
Figure 3:
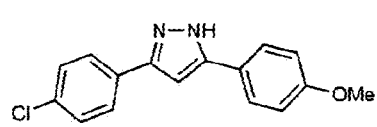
Figure 3:
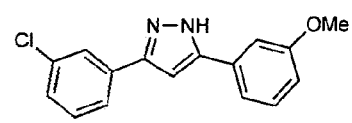
Figure 3:
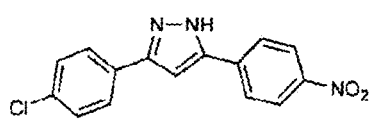
Figure 3:
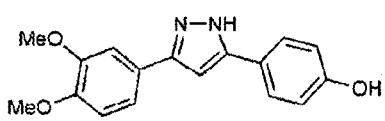
Figure 3:
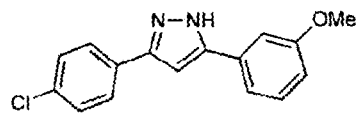
Figure 3:
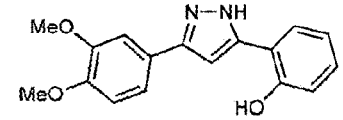
Figure 3:
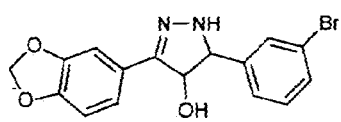
Figure 3:
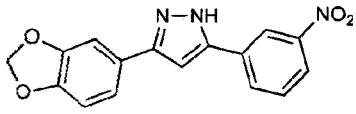
Figure 3:
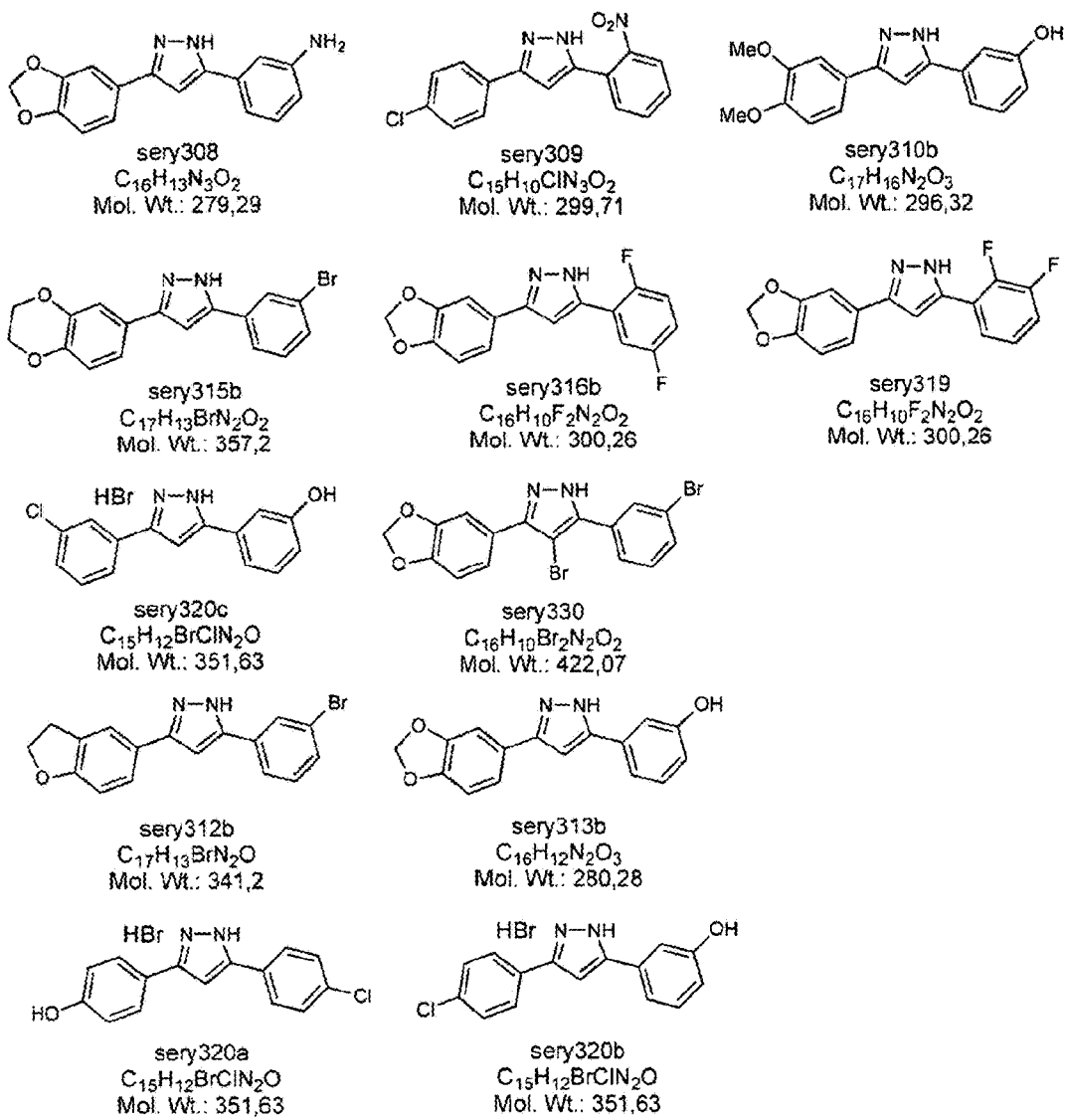

The above examples represent examples of how to synthesise or derivatise the desired compounds. The remaining compounds shown in FIG. 3 were synthesised accordingly. These chemically synthesised substances, together with selected substances of the initial screening, where subjected to further tests, including SIFT assays, cell cultures based assays, in vivo experiments on mice as well as biochemical assays directed to α-synuclein aggregation (see below). A list of substances tested is provided in FIG. 3.

Example 3: Material and Methods Used

Compound Libraries

The libraries screened contain 10.000 compounds each and are called DIVERSet1 and DIVERSet2 by us, because they cover only a part of the larger DIVERSet library (ChemBridge Corp., San Diego, Calif.). DIVERSet is a collection of rationally selected, diverse, drug-like small molecules. The compounds were supplied in dimethyl sulfoxide (DMSO) solution and on 96-well microtiter plates. A database containing molecular structures and some physicochemical data for each of the compounds is available at www.chembridge.com.

Production of Recombinant Mouse PrP 23-231

Recombinant PrP 23-231 was produced and purified essentially as described by Liemann et al. (1998), except that for bacterial expression BL21DE3 RIL E. coli cells (Novagen) were transformed with plasmid pET17b-MmPrP23-231WVVT31 for mouse PrP23-231. Also, the bacteria were grown to an optical density of 0.5 before protein production was induced by addition of 1 mM IPTG and cells harvested two hours later. Then bacteria were lysed by addition of 0.5% Triton X-100 to the lysis buffer and incubation for 30 min at 37° C. instead of using a French press. Furthermore, the gel filtration was replaced by a nickel chelate affinity chromatography step. The final cation exchange chromatography step after refolding was also omitted.

In particular, the PrP prepurified by ion exchange chromatography was subjected to oxidation as described and oxidation was terminated by addition of 0.1 mM EDTA and adjustment of pH to about 6. After addition of 0.1 mM NiCl2 up to 50 mg of PrP were applied to 2 mL chelating sepharose (Pharmacia) precharged with NiCl2 according to the manufactures recommendations and preequilibrated with buffer A (8 M Urea, 10 mM MOPS pH7.0). Binding of PrP to Ni-chelate matrix was performed for at least 3 h at room temperature by continuously inverting the mixture. The matrix was transferred to a polyprep-column (BioRad) and drained from the flow through. The column was washed twice with 5 mL buffer B (8 M Urea, 10 mM MOPS pH7.0, 500 mM NaCl) and then eluted sequentially with 6 times 5 mL buffer D (7.2 M Urea, 10 mM MOPS pH 7.0, 150 mM NaCl, 50 mM Imidazole). Fractions containing purified PrP were pooled, concentrated with a centriprep device and finally diluted 1:50 for refolding into 10 mM MES pH 6.0.

Fluorescent Labelling of Antibodies and Recombinant PrP

L42 monoclonal antibody (r-biopharm, Darmstadt, Germany) was labelled with Alexa Fluor 647 (Alexa-647; Invitrogen, Eugene) according to the manufacturer's manual. Recombinant mouse PrP 23,231 was labelled with the Alexa Fluor 488 (Alexa-488; Invitrogen, Eugene) in 20 mM potassium phosphate buffer, pH 6, 0.1% Nonidet P40, 40 mM sodium bicarbonate buffer, pH 8.3. Unbound fluorophores were separated by gelfiltration on PD10 columns (GE Healthcare, Freiburg, Germany) equilibrated with 20 mM potassium phosphate buffer, pH 6, 0.1% Nonidet P40. Quality control of labelling reaction and ratio was performed by fluorescence correlation spectroscopy (FCS) measurements on an Insight Reader (Evotec Technologies, Hamburg, Germany). The labeling ratio was approximately 1,3 fluorophores per rPrP molecule.

Assay for PrPC-PrPSc Association

PrPSc was prepared from brain of CJD patients according to Safar et al. (Safar et al. (1998)) and aliquots of the final pellet resuspended in 1×PBS+0.1% sarcosyl solution were diluted fivefold into buffer A (20 mM potassium phosphate buffer at pH 6.0, 0.1% Nonidet P40) and sonicated in a water bath sonicator for 60 s. After centrifugation at 1000 rpm for 1 min the supernatant was diluted 100-fold in buffer A for the assay.

A mixture of labelled mouse rPrP and labelled L42 monoclonal antibody was prepared in 20 mM potassium phosphate buffer, pH 6, 0.1% Nonidet P40 so that the labelled molecules were approximately equally abundant at 2-6 nM. In a 20 µL assay volume 8 µL of the rPrP/antibody mixture, 2 µL compound and 10 µL of the diluted PrPSc preparation were mixed. The samples were loaded onto 96-well plates with cover-glass bottom (Evotec-Technologies, Hamburg, Germany) and measured on an Insight Reader.

Single-Particle Measurement and Analysis

FIDA measurements were performed at excitation energies of 200 µW for the 488 nm laser and 300 µW for the 633 nm laser. Scanning parameters were set to 100 µm scan path length, 50 Hz beamscanner frequency, and 2000 µm positioning table movement. The measurement time was 10 s. Fluorescence from the two fluorophores was recorded separately with single photon detectors and photons were summed over time intervals of constant length (bins) using a bin length of 40 µs. The number of red and green fluorescent photon counts was measured and analysed in a two-dimensional intensity distribution histogram, as previously described (Bieschke et al., 2000).

The fluorescence intensity data was evaluated using a 2D-SIFT software module (Evotec-Technologies, Hamburg, Germany) by summing up high-intensity bins in sectors. Cut-off values for bin intensities for each measurement series were adjusted manually according to the control measurements.

Example 4: Therapeutic Application of Novel Potential Antiprion-Compounds in Scrapie Infected Mice after Day 80 Post Infection In order to prove the effectiveness of those novel pot form encephalopathies (TSE) or prion diseases animal experiments were performed, in which compounds having antiprion activity in the SIFT and/or scrapie cell culture assay were used to treat mice infected with the RML strain of scrapie at a late stage of the incubation period. We choose the intraperitoneal application of the compounds at a 14 day time interval at 80 days after infection, because this is typically the time when first subclinical symptoms appear in animals infected with this prion strain. This would correspond to the earliest time a TSE affected human being showing first symptoms of disease would realistically receive a therapeutic treatment. By choosing such very stringent conditions for therapy we wanted to assess the functionality of the tested compounds as prion therapeutics in a realistic setting. Typically TSE therapeutics have to date only been tested for postexposure prophylaxis in animal experiments, where they are applied around the time of infection with prions. In real life there are only very rare occasions, where such a therapeutic regime is feasible for TSE affected individuals. For most TSE patients the time of infection or begin of the incubation time for the familial and sporadic cases (which are the vast majority) is unknown and can not be realized. Therefore the majority of TSE patients will only be able to receive treatment after the occurrence of the first symptoms of TSE.

Experimental Procedures:

6-7 weeks-old, female C57Bl6 mice were inoculated with RML scrapie by intracerebral injection with 30 µL of 1% sterile brain homogenate in phosphate buffered saline (PBS) from mice terminally ill with the RML scrapie-strain. At 80 days post infection these mice were treated with selected novel potential antiprion-compounds or with the vehicle aqueous Dimethylsulfoxide (DMSO). Five potential antiprion-compounds had been selected according to their antiprion activity in a cell culture model for this treatment, which were designated 10353F11 according to the plate-position in the Diverset chemical compound library (Chembridge Corp., San Diego, USA) and anle138b, anle143b, sery106 and sery149. The treatment with these compounds was carried out for 14 consecutive days by intraperitoneal injection of 50 µL per day of the compound 10353F11 dilution respective 25 µL for the other compounds in the vehicle (DMSO). Compound 10353F11 was used at a concentration of 10 mM and for the compounds anle138b, anle143b, sery106 and sery149 100 mM were injected throughout the entire period. The animals were monitored daily for signs of disease by trained animal caretakers from day 80 post infection on. The animals were sacrificed, when they had reached the terminal stage of the disease marked by the clinical symptoms, which are ataxia, tremor, difficulty in righting up from a position lying on its back, and tail stiffness, and were moribund. Typically the disease progress through the terminal stage of disease will lead to the death of the animal within one or two days. From the sacrificed animals one hemisphere and one half of the spleen were freshly frozen at −80° C. for western blot analysis, while the second hemisphere and the second half of the spleen as well as all inner organs were fixed in 4% formaldehyde solution for (immune-) histology.

Results

Figure 4:
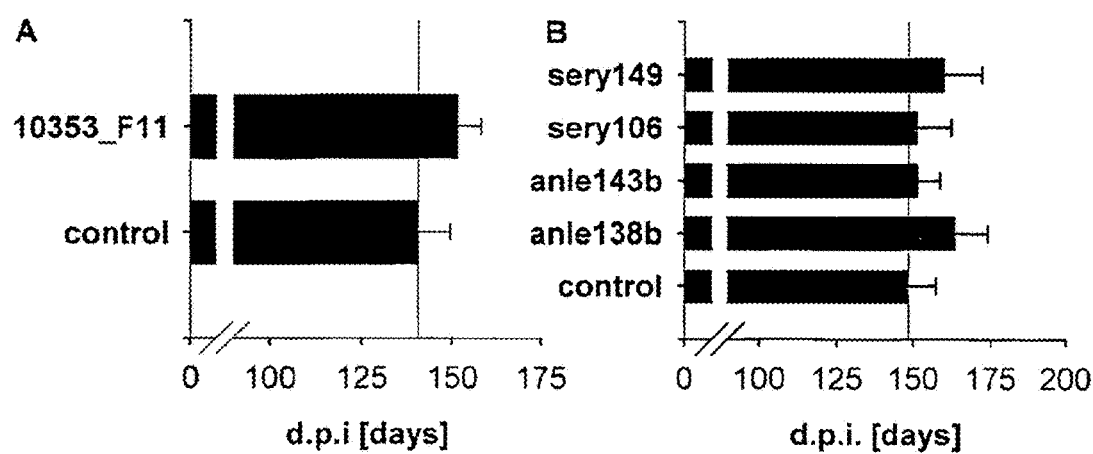
FIG. 4: Effects of treatment on survival time of mice after intracerebral infection with RML scrapie. The compounds were administrated daily for 14 days from day 80 post infection (50 μL 10 mM compound). (A) treatment with compound 10353_F11 prolongs survival of intracerebrally infected mice (p<0.05). In (B) are shown the mean survival times after treatment with different compounds. A daily intraperitoneal injection with compounds anle138b and sery149 significantly prolongs the survival times after challenge with RML scrapie (anle138b: p<0.01; sery149: p<0.05). mean survival times are expressed in days±standard deviation.

As shown in FIG. 4 treatment of mice, which had been intracerebrally infected with the RML scrapie strain, at a late stage of the incubation time (day 80 p.i.) by daily intraperitoneal application of the selected potential anti-prion drugs resulted in a prolongation of the incubation time, until the terminal stage of the scrapie infection was reached, for 10353F11 (FIG. 4 A) and anle138b and sery149 (FIG. 4 B). The average survival time determined for compounds anle138b and sery149 for groups of seven and eight animals each was prolonged by 14.9 and 11.5 days, respectively, in comparison to a group of twelve animals that had received only the vehicle 100% DMSO. For compounds sery106 and anle143b the prolongation of the survival time in a group of eight treated animals compared to the same DMSO-control group was below the level of statistical significance. For compound 10353F11 survival time determined for a group eight animals each was prolonged by 11 days compared to the control group. The observed survival time prolongation in the experiments corresponds roughly to the duration of the treatment. This may imply that the treatment with these drugs has halted the disease progression as long as the drugs were administered. In this case the treatment with these drugs would lead to a prolongation of the lives of TSE-infected individuals and to a stabilization of their health status protecting it from further deterioration by halting the disease progress.

Example 5: Therapeutic Application of a Potential Antiprion-Compound in Scrapie-Infected Mice after Intraperitoneal Infection To prove the effectiveness of this novel antiprion-compound in combating transmissible spongiform encephalopathies (TSE) or prion diseases an additional animal experiment was performed. For this experiment mice were infected intraperitoneal with RML scrapie and treated with compound anle138b, which has proven its antiprion activity in an animal model for late stage prion disease (Example 4). We choose a combination of the intraperitoneal and oral application of the compound and started the treatment right after infection.

Figure 5:
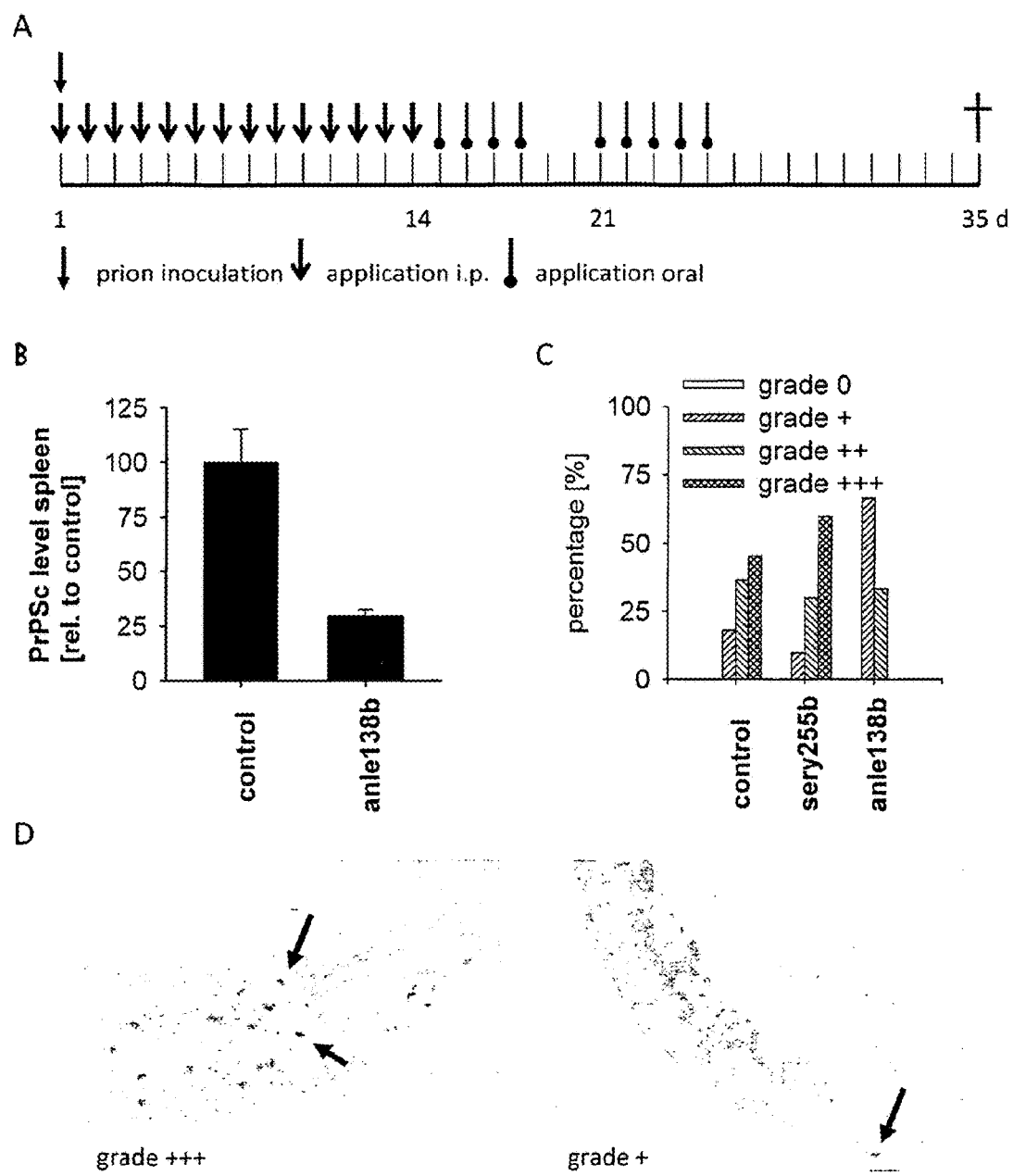
FIG. 5: Influence of treatment on splenic PrPSc level of mice intraperitoneal infected with RML scrapie. (A) After inoculation with scrapie prions the mice were treated once a day with compound (25 μL 100 mM compound for intraperitoneal and 50 mg/kg for oral administration. (B) Densitometric analysis of splenic PrPSc levels in a dot blot assay. Treatment with anle138b induced a strong reduction in PrPSc levels compared to control (p=0.001). (C) Immunohistological analysis of spleens from scrapie-infected mice. After treatment with anle138b the percentage of spleens with low PrPSc deposits increases (grade +) and strong PrPSc deposits are abolished (grade +++). (D) shows two examples of PrPSc stained deposits (arrows) in spleens. left picture shows strong PrPSc staining (grade +++), whereas the right one shows low PrPSc staining (grade +). bars indicate the mean PrPSc level±standard error.

Experimental Procedures:

Scrapie-Infection and Treatment of Mice 6-7 weeks-old, female C57Bl6 mice were inoculated with RML scrapie by intraperitoneal inoculation with 100 µL of 1% sterile brain homogenate in phosphate buffered saline (PBS) from mice terminally ill with the RML scrapie-strain. The treatment of these mice with compound anle138b or with the vehicle aqueous Dimethylsulfoxide (DMSO) started right after infection. The treatment with this compound was carried out for 14 consecutive days by intraperitoneal injection of 25 µL per day of the compound diluted in the vehicle (DMSO) followed by 4 and 5 days oral administration of 50 µL per day of the compound in a mixture of vegetable oil/DMSO via oral gavage (FIG. 5 A). The compound anle138b was used at a concentration of 100 mM for intraperitoneal application and for oral administration 50 mg/kg. The animals were sacrificed on day 35 post infection, when PrPSc is clearly detectable in the spleen of intraperitoneal infected mice. From the sacrificed animals one half of the spleen were freshly frozen at −80° C. for western blot analysis, while the second half of the spleen as well as all inner organs were fixed in 4% formaldehyde solution for immunohistology.

PET Blot

Formalin-fixed brain tissue was cut into 2-mm-thick tissue blocks, decontaminated in concentrated formic acid for 1 hour, postfixed in 4% phosphate-buffered saline-buffered formalin for 48 hours following the protocol of Brown et. al. 1990 and embedded in paraffin. Sections (5-7 µm) were cut on a microtome, placed in a water bath (55° C.), collected on a prewetted 0.45 µm pore nitrocellulose membrane (Bio-Rad, Richmond, Calif.), and dried for at least 30 minutes at 55° C. The nitrocellulose membrane was deparaffinized with xylene. Xylene was replaced with isopropanol, followed by stepwise rehydration. Tween 20 was added at a final concentration of 0.1% to the last rehydration step in distilled $H_2O$. Membranes were dried and stored at room temperature for months without loss of quality of subsequent PrPSc staining.

After prewetting with TBST (10 mmol/L Tris-HCl, pH 7.8; 100 mmol/L NaCl; 0.05% Tween 20) digestion was performed with 250 µg/ml proteinase K (Boehringer) in PK-buffer (10 mmol/L Tris-HCl, pH 7.8; 100 mmol/L NaCl; 0.1% Brij 35) for 8 hours at 55° C. With this step the membrane-attached proteins were fixed to the membrane. After washing three times with TBST, the proteins on the membranes were denatured with 3 mol/L guanidine isothiocyanate in 10 mmol/L Tris-HCl (pH 7.8) for 10 minutes. Guanidine was washed out three times with TBST. Immunodetection was performed after preincubation in blocking solution (0.2% casein in TBST) for 30 minutes. As primary antibody a polyclonal rabbit antibody against recombinant mouse PrP, designated CDC1, was used at a dilution of 1:500 in Antibody-Diluent solution (Ventana). Incubation was for at least 1 hour. After three washes in TBST, incubation for at least 1 hour was performed with an alkaline phosphatase-coupled rabbit anti-mouse antibody (Dako, Hamburg) at a dilution of 1:500. After five washes in TBST for 10 minutes, the membranes were adjusted to alkaline pH by incubating two times for 5 minutes in NTM (100 mmol/L Tris-HCl, pH 9.5; 100 mmol/L NaCl; 50 mmol/L $MgCl_2$). The visualization of the antibody reaction was provided by formazan reaction using NBT/BCIP. Blots were evaluated with an Olympus dissecting microscope.

Results

Spleen tissue extracted after the death of drug-treated and vehicle-treated mice was immunohistochemically stained for the presence of PrPSc deposits and analysed for splenic PrPSc level with immunoblot. As shown in FIG. 5 B the splenic PrPSc level of the treated animals decreases significantly compared to the vehicle-treated mice. Examination of spleen tissue from infected mice shows that PrPSc deposits were reduced after treatment with compound anle138b. The percentage of spleens with low PrPSc deposits increases and strong PrPSc deposits are reduced (FIG. 5 C). In (FIG. 5 D) are shown examples of two PET Blots, PrPSc deposits. The results indicate a clear antiprion efficiency of this compound in peripheral tissues by the chosen experimental set-up and therapeutic regime.

Example 6: Therapeutic Application of Novel Antiprion-Compounds in Scrapie Infected Mice after Day 80 Post Infection In order to prove the observation from example 4 that the survival time prolongation corresponds to the duration of the treatment an animal experiment was performed, in which compounds were administered at a higher dosage and longer duration to treat mice infected with the RML strain of scrapie at a late stage of the incubation period. We chose a combination of the intraperitoneal and oral application of the compounds at 80 days after infection, because this is typically the time when first subclinical symptoms appear in animals infected with this prion strain.

Figure 6:
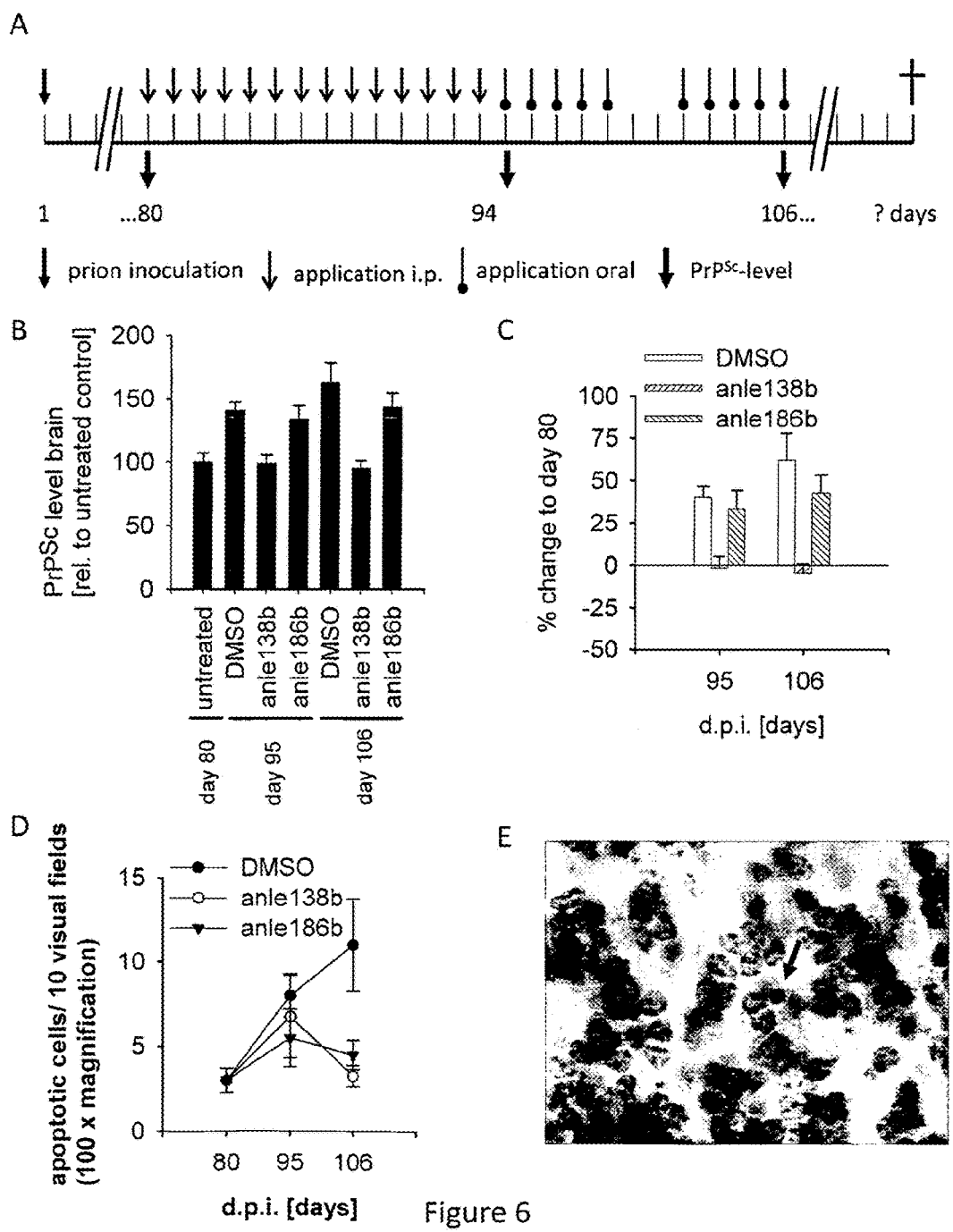
FIG. 6: Immunoblot and histological analysis of mice brain. (A) The treatment of mice after intracerebral inoculation of mice with RML scrapie started 80 days post infection. Compounds were given at indicated time points (25 μL 100 mM compound for i.p. application and 50 mg/kg for oral administration). (B) Quantification of PrPSc levels in brain homogenates of prion-inoculated mice at different time points. Treatment with anle138b blocks PrPSc accumulation in brain completely. The amount of PrPSc on day 106 is still at the level of day 80. Treatment with anle186b leads to a reduction of PrPSc accumulation in mouse brains (C) change of relative PrPSc levels after treatment with compounds compared to untreated control at day 80. (D) histological examination of apoptotic cells (arrow in (E)) in H&E stained brain slices at indicated time points. The line plot shows mean number of apoptotic cells±standard error. (E) show a H&E stained section with an apoptotic cell (arrow).

Experimental Procedures:

6-7 weeks-old, female C57Bl6 mice were inoculated with RML scrapie by intracerebral injection with 30 µL of 1% sterile brain homogenate in phosphate buffered saline (PBS) from mice terminally ill with the RML scrapie-strain. These mice were treated at day 80 post infection with novel antiprion-compounds or with the vehicle DMSO. The two potential antiprion-compounds anle138b and anle186b were used. The treatment with these compounds was carried out for 14 consecutive days by intraperitoneal injection of 25 µL per day of the compound diluted in the vehicle DMSO followed by two oral administrations for 5 days of 50 µL per day of the compound in a mixture of vegetable oil/DMSO via oral gavage (FIG. 6 A). In 3 control mice and 2 mice treated with anle138b the compound was additionally given orally from day 109 to day 136 by providing peanut butter food pellets mixed with the DMSO/compound stock solutions. The compounds were used at a concentration of 100 mM for intraperitoneal application and for oral administration 50 mg/kg. Four animals of each treatment group were sacrificed at the indicated time points (FIG. 6 A). Eight animals of each treatment group were monitored daily for signs of disease by trained animal caretakers from day 80 post infection on. The animals were sacrificed, when they had reached the terminal stage of the disease marked by the clinical symptoms, which are ataxia, tremor, difficulty in righting up from a position lying on its back, and tail stiffness, and were moribund. Typically the disease progress through the terminal stage of disease will lead to the death of the animal within one or two days. From the sacrificed animals one hemisphere and one half of the spleen were freshly frozen at −80° C. for western blot analysis, while the second hemisphere and the second half of the spleen as well as all inner organs were fixed in 4% formaldehyde solution for histology.

Results

PrPSc Level in Brain Homogenates and Apoptotic Cell Death after Infection

Brain homogenates of drug-treated and vehicle-treated mice were analysed for PrPSc levels by immunoblot analysis. As shown in FIG. 6 B the PrPSc level in the brain of all animals examined at the indicated time points from the anle138b-group could be held at the level of untreated mice at day 80, whereas the PrPSc level in the control group increases. The results for anle186b lie in between the control group and anle138b. The increase of PrPSc could be slowed down (FIG. 6 B). FIG. 6 C shows the change of relative PrPSc levels after treatment with compounds compared to untreated control at day 80. The PrPSc level in brains is slighty decreased after treatment with anle138b. After histological examination of H&E stained brain slices at indicated time points the anle138b and anle186b treated mice showed a reduction of pathological changes. The number of apoptotic cells in the cerebellar granule cell layer of infected mice from the treated groups is decreased in comparison to the control group (FIG. 6 D). These results indicate that both compounds can cross the blood-brain-barrier. Therefore the therapy was able to prevent further PrPSc deposition and disease progression in the brain of the animals during treatment. These results imply that the treatment with compound anle138b has halted the disease progression as long as the drugs were administered. These results indicate that it may be possible to modify the disease progress by a therapy using this compound by interfering with PrPSc formation. In this case the treatment would lead to a prolongation of the lives of TSE-infected individuals and to stabilization or maybe an improvement of their health status protecting it from further deterioration by halting the disease progress.

Incubation Time Prolongation

Figure 7:
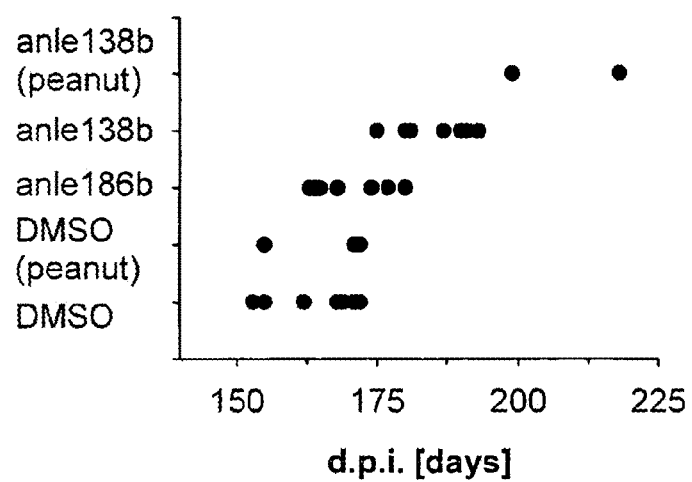
FIG. 7: Prolongation of survival time by daily administration of the compounds of the invention. Mice, which have been intracerebrally infected with the RML scrapie strain, show a prolonged survival time until the terminal stage of the scrapie infection was reached.

As shown in FIG. 7 treatment of mice, which had been intracerebrally infected with the RML scrapie strain, at a late stage of the incubation time (day 80 p.i.) by daily administration of compounds resulted in a prolongation of the survival time, until the terminal stage of the scrapie infection was reached (FIG. 7). Moreover, the longer survival times in the two mice which received an additional treatment from day 109 to day 136 by feeding anle138b mixed with peanut butter indicates that i) survival correlates with duration of treatment, ii) the compound is effective when given orally, and iii) the compound crosses the blood-brain-barrier.

Example 7: Suppression of α-Synuclein Aggregation In Vitro

Synucleinopathies are (neurodegenerative) diseases characterized by the intracellular accumulation of aggregates and fibrils composed mainly of the protein α-synuclein (for review see: Goedert, 2001). The most prominent neurodegenerative synucleinopathies are Parkinson's Disease (PD), Dementia with Lewy bodies (DLB), and multiple system atrophy (MSA).

The aggregation of α-synuclein in vitro has been demonstrated to occur in the presence of substances, such as organic solvents, that mimic dielectric conditions as they exist naturally in the close vicinity of biological membranes (Munishkina et al., 2003). In vitro aggregation assays have been developed that provide model systems for the investigation of central aspects of α-synuclein misfolding and aggregation and for the formation of toxic aggregate species during the disease process (Kostka et al 2008).

In order to test selected compounds for their potential to suppress α-synuclein aggregation we have used an in vitro system, where the organic solvent dimethylsulfoxid (DMSO) at low concentrations (<3%) and—in some experiments—ferric iron was used to induce α-synuclein aggregation in vitro. The multimer formation was monitored using a single particle fluorescence correlation set up by cross-correlation analysis and SIFT-analysis applied to mixtures of α-synuclein monomers labeled with green Alexa488- or red Alexa647-fluorophores, respectively. Such α-synuclein mixtures were aggregated in parallel to samples where a compound was added to the reaction.

Experimental Procedures:
Fluorescence Labeling of α-Synuclein

Recombinant α-synuclein was labeled with amino reactive fluorescent dyes, either with Alexa Fluor-488-O-succinimidyl ester or with Alexa Fluor-647-O-succinimidyl ester (Molecular Probes, USA), respectively. After completion of the reaction unbound dye molecules were separated by size-exclusion chromatography of the reaction mixtures through two successive PD10 columns (Amersham Bioscience, Germany) according to the manufacturers instructions. The labeling efficiency and removal of unbound dye was determined by FCS measurements with suitable dilutions of fractions containing the labeled α-synuclein monomers.

Single Particle Fluorescence Correlation Measurements

In a 20 μl volume in the wells of a special micro-titer plate equipped with a glass cover slide bottom for fluorescence correlation measurements (Evotec-Technologies, Germany) α-synuclein aggregation was performed in a buffer containing 50 mM Tris at pH 7.0 and a mixture of α-synuclein monomers labeled with either Alexa488- or Alexa647-fluorophores, respectively, at a final concentration of approximately 5-10 nM of each α-synuclein species. The measurements were performed on an Insight fluorescence correlation instrument (Evotec-Technologies, Germany) using a 40× microscope objective of 1.2 NA (Olympus, Japan) with FIDA optical settings, a pinhole diameter of 70 μm, and 200 μW excitation with the 488 nm laser as well as 300 μW excitation with the 633 nm laser. Measurement time was 10 s, during which the laser focus was moved through the well by a beam scanner device using a scan path length of 100 μm at a scanning frequency of 50 Hz and a positioning table movement of 2000 μm. This is equivalent to a scanning speed of approximately 10 mm/s. Two-dimensional intensity distribution histograms, were generated and analysed using the 2-D SIFT software (Evotec OAI, Germany).

Results: Suppression of α-Synuclein Aggregation by Compounds

Figure 8:
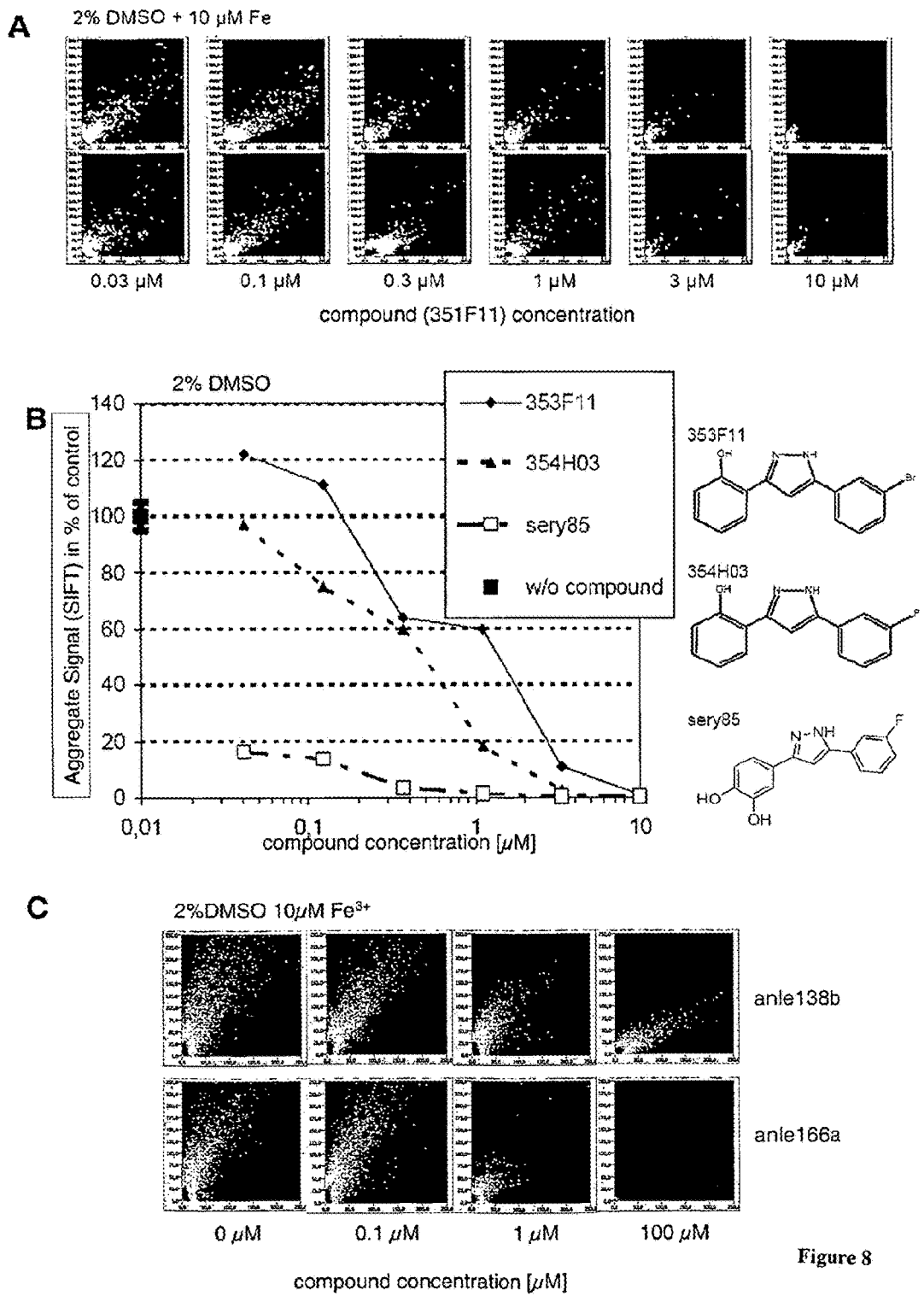
FIG. 8: Suppression of α-synuclein aggregation by the compounds of the invention. (A) The DPP-compound 351F11 is capable of inhibiting the formation of multimeric α-synuclein complexes in a dose-dependent way. (B) (C) Dose-dependent inhibitory effect on α-synuclein aggregation detected for other DPP-related compounds.

The aggregation of α-synuclein caused by DMSO and DMSO/$Fe^{3+}$ is reflected by an formation of multimeric α-synuclein complexes that contain both red and green labeled α-synuclein units in higher numbers. Thus, the control reaction without added inhibitory compounds shows the presence of a large number of complexes that emit high numbers of photons. The addition of the DPP-compound 351F11 to the assay solution is capable of inhibiting the formation of multimeric α-synuclein complexes in a dose-dependent way to a large extent as can be seen in FIG. 8A. Thus, compound 351F11 is able to inhibit efficiently the multimer formation of α-synuclein at a low micro molar concentration in this in vitro model for the pathological protein aggregation found in synucleinopathies. This is a clear indication that compound 351F11 can not only function as an anti-prion compound, but that it has also the potential to become a therapeutic compound for synucleinopathies, like Parkinson's Disease, DLB, and MSA, which interferes with the pathologic mechanism at the molecular level. A dose-dependent inhibitory effect on α-synuclein aggregation can also been detected for the DPP-related compounds investigated (FIG. 8 B,C). Therefore these compounds represent a novel group of substances with a proven capacity to inhibit α-synuclein aggregation in vitro, that will allow the development of a causative therapy against Parkinson's disease and other synucleinopathies.

Furthermore, the inhibitory activity of these compound on both, prion protein- and α-synuclein-aggregation in vitro, may reflect its general anti-aggregatory activity against a broader range of protein aggregation diseases, where protein misfolding into predominantly β-sheet conformations forms the basis for subsequent protein aggregation into amyloid fibrils. Therefore, these compounds and further members of the DPP-class of substances have the potential of being useful as therapeutics for the causative treatment of a whole panel of (neurodegenerative) protein aggregation diseases, including for example Alzheimer's disease, prion disease, Parkinson's disease, multiple system atrophy, Diffuse Lewy body disease, frontotemporal dementia, amyotrophic lateral sclerosis, Huntington disease's, spinocerebellar ataxias and other Poly-Q diseases, hereditary cerebral amyloid angiopathy, familial amyloid polyneuropathy, primary systemic amyloidosis (AL amyloidosis), reactive systemic amyloidosis (AA amyloidosis), type II diabetes, injection-localized amyloidosis, beta-2 microglobulin amyloidosis, hereditary non-neuropathic amyloidosis, Finnish hereditary systemic amyloidosis.

Example 8: Inhibition of PrPSc in Cell Culture

Figure 9:
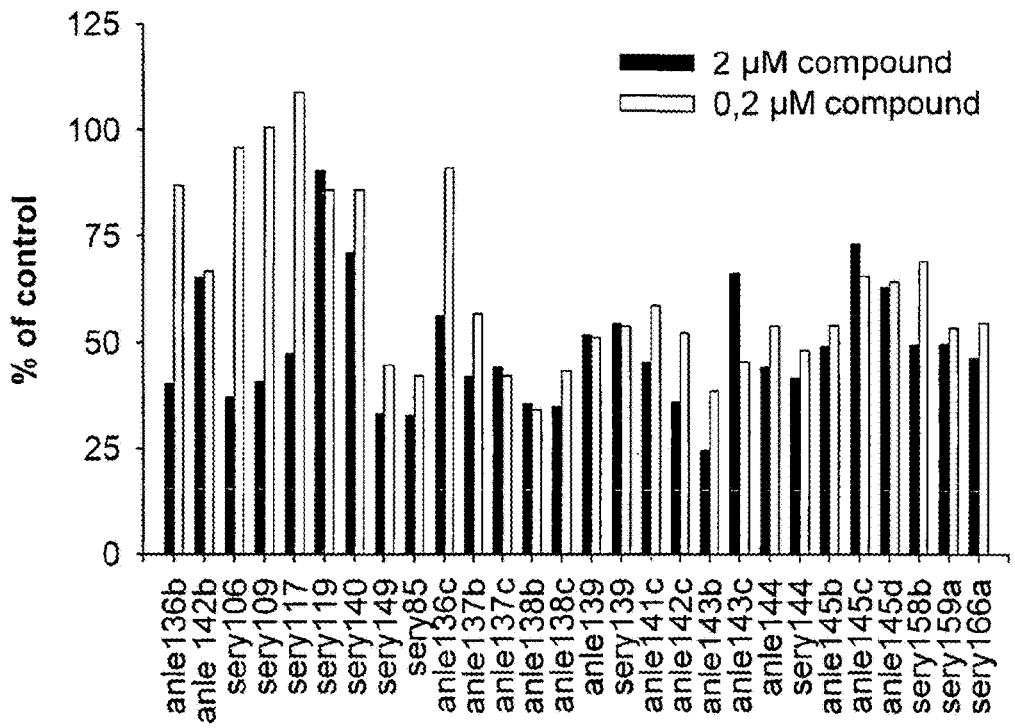
FIG. 9: Prion infected cell cultures treated with DPP-related compounds of the invention. DPP-related compounds exhibited a strong reduction of PrPSc in cell culture at low micromolar and even at sub-micromolar concentrations.
Figure 9:
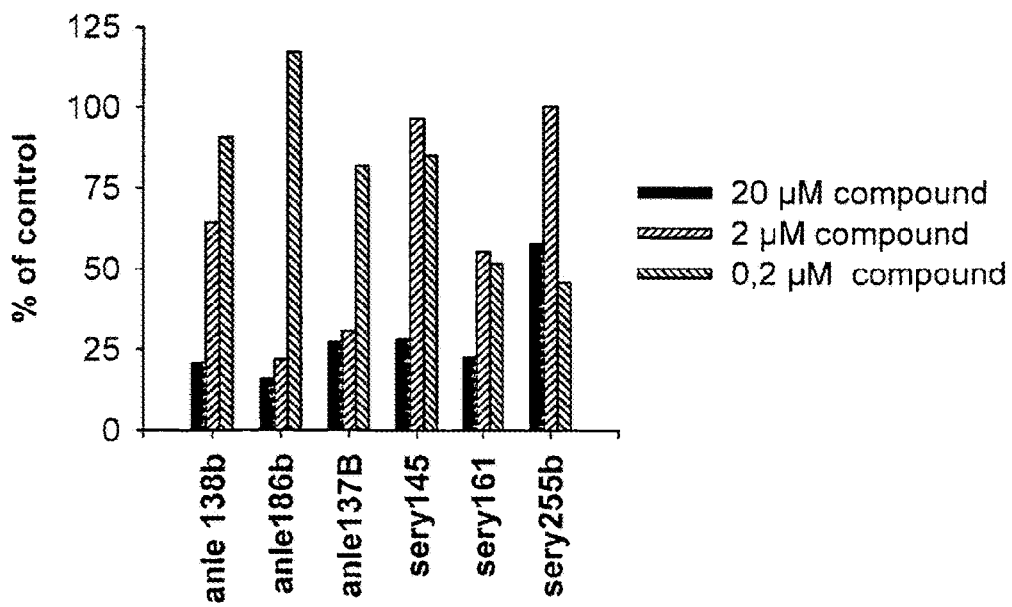

Experimental Procedures:
Prion infected cell cultures were treated with newly synthesized compounds as described for the primary screening described above. Compounds were added at the concentrations indicated in FIG. 9. The structures of the compounds are shown in the following and in FIG. 3.

49

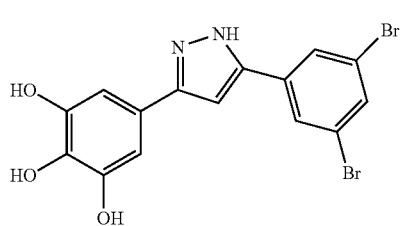

5-(3,5-Dibromophenyl)-3-(3,4,5-trihydroxyphenyl)pyrazole (anle145d)

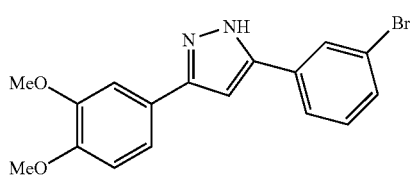

5-(3-Bromophenyl)-3-(3,4-dimethoxyphenyl)pyrazole (sery255b)

Results:

A very high proportion of DPP-related compounds exhibited a strong reduction of PrPSc in cell culture at low micromolar and even at sub-micromolar concentrations. This indicates that these compounds represent a group of related chemicals with anti-prion activity.

50

Example 9: Inhibitory Effect of Different DPP-Derivates on PrP$^{Sc}$ Accumulation in Brain and Spleen Compounds were tested in regard to their inhibitory effect on PrPSc accumulation in vivo by three experimental protocols:

a) C57BL/6 mice were inoculated intracerebrally (i.c.) with 30 µL of 1% brain homogenate (RML scrapie). Treatment was started at 80 days post infection with 1 mg compound per day applied orally mixed with DMSO+peanut butter. PrP$^{Sc}$ level in brain was measured at 120 days post infection by immunoblot analysis.

b) C57BL/6 mice were inoculated intracerebrally (i.c.) with 30 µL of 1% brain homogenate (RML scrapie). Treatment was started at 80 days post infection with 0.84 mg compound (in DMSO) per day applied by intraperitoneal injection for 14 days followed by 2×5 days (with 2 days without treatment in between) of 1 mg compound (in DMSO+ vegetable oil) applied orally by gavage. PrP$^{Sc}$ level in brain was measured at 106 days post infection c) C57BL/6 mice were inoculated intraperitoneally (i.p.) with 100 µL of 1% brain homogenate (RML scrapie). PrP$^{Sc}$ level in the spleen was determined at 35 days post infection following 34 days of treatment with 1 mg compound mixed with DMSO+peanut butter per day.

The relative inhibition of PrP$^{Sc}$ accumulation compared to DMSO-treated groups are shown in table 1 (mean value of DMSO-treated animals at the end of the treatment period was defined as 0% inhibition, mean value of control animals at the start of the treatment period was defined as 100% inhibition).

TABLE 1

Inhibitory effect of different DPP-derivates on PrP$^{Sc}$ accumulation in brain and spleen

| compound | R1 | R2 | R3 | Inhibition [%]** |
|---|---|---|---|---|
| anle138b | (3,4-methylenedioxyphenyl) | | (3-bromophenyl) | 69$^a$; 108$^b$; 62$^c$ |
| sery255b | (3,4-dimethoxyphenyl) | | | 40$^a$; <10$^c$ |
| anle138c | (3,4-dihydroxyphenyl) | | | <10$^a$ |
| sery338b | (3,5-dimethylisoxazole) | | | 27$^a$ |

TABLE 1-continued
Inhibitory effect of different DPP-derivates on PrP$^{Sc}$ accumulation in brain and spleen
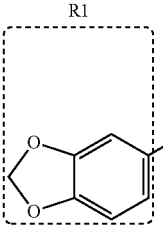
| compound | R1 | R2 | R3 | Inhibition [%]** |
|---|---|---|---|---|
| sery345 | | 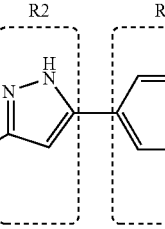 | | <10$^a$ |
| sery378b | | |  | 40$^a$ |
| anle234b | | |  | <10$^a$ |
| sery335b | | | 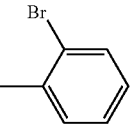 | 60$^a$; 46$^c$ |
| anle186b | | | 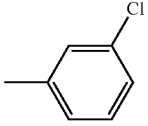 | 31$^b$ |
| anle197b | | | 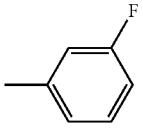 | <10$^c$ |
| anle236b | | | 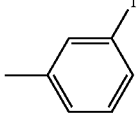 | <10$^a$ |
| sery313 | | | 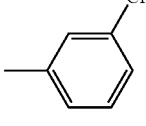 | 37$^c$ |
| anle232b | | | 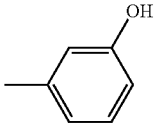 | <10$^a$ |

TABLE 1-continued

Inhibitory effect of different DPP-derivates on PrP$^{Sc}$ accumulation in brain and spleen

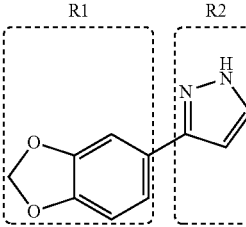

| compound | R1 | R2 | R3 | Inhibition [%]** |
|---|---|---|---|---|
| anle233b | | | 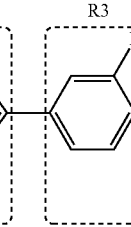 | 17$^a$ |

($^{a,b,c}$ indicate the experimental protocol (as described above) that was used)

The results of these experiments indicate that under these experimental conditions i) the compound anle138b and chemically related compounds provide a strong inhibition of prion amplification in vivo, ii) there is a structure-activity relationship that indicates that for this application under these experimental conditions anle138b represents one relative optimum of activity.

Example 10: The Blood-Brain-Barrier can be Passed and an Interaction with Pathological Protein Aggregates is Observed C57BL/6 mice were inoculated intracerebrally (i.c.) with 30 μL of 1% brain homogenate (RML scrapie). Treatment was started at 80 days post infection with 1 mg compound (sery383) or 3 mg compound (sery363a) per day applied orally mixed with DMSO+peanut butter. PrP$^{Sc}$ level in brain was measured at 120 days post infection by immunoblot analysis.

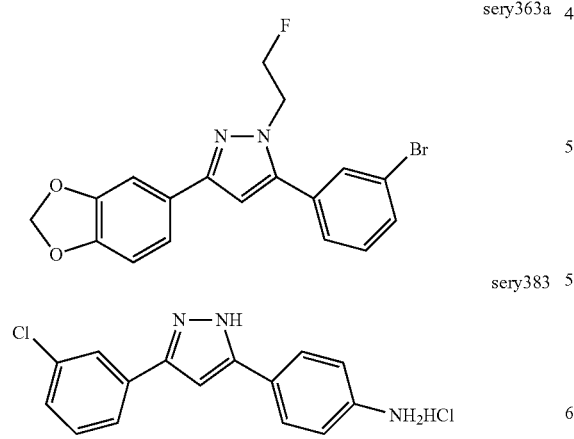

Compared to DMSO-treated controls, sery363a resulted in a reduction of PrPC accumulation by 35%, sery383 resulted in a reduction of PrPC accumulation by 30%.

Sery363a was synthesized and tested in these experiments, because it provides a modification of anle138b that is well suited for isotope labeling, which is needed for use as a diagnostic tracer for PET imaging.

Sery383 was tested in this assay, because this compound, as well as structurally similar compounds containing a —NH2 group and a halogen atom, were found to be highly active for the inhibition of alpha-synuclein aggregation (see example 16, "Inhibition of the formation of α-synuclein aggregates by different compounds")

The results of these experiments indicate that both compounds can pass the blood-brain-barrier and interact with pathological protein aggregates, which shows that these compounds have properties that can be exploited by use as a therapeutic compound as well as a diagnostic compound.

Figure 10:
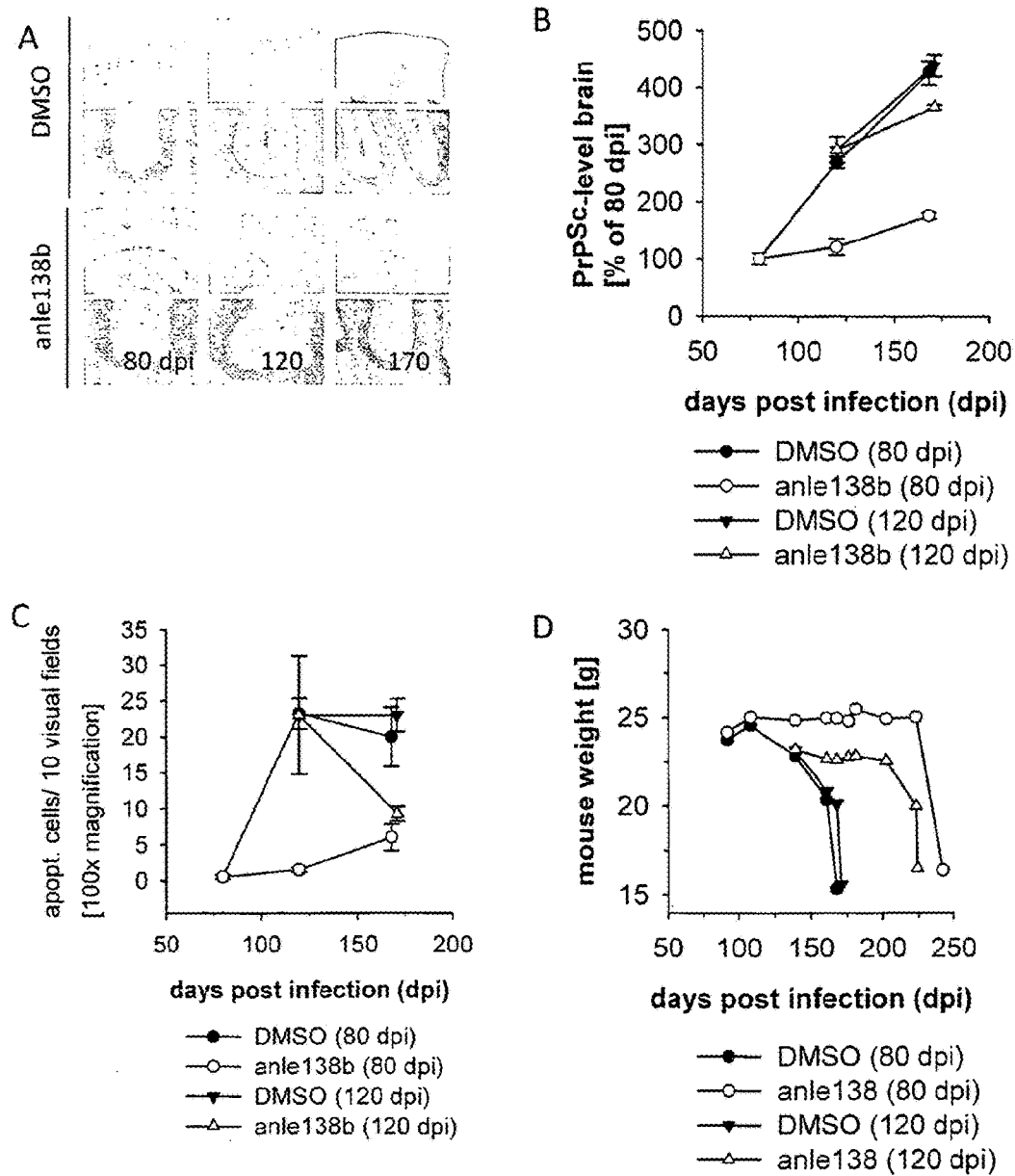
FIG. 10: Influence of daily treatment with anle138b on $PrP^{Sc}$ accumulation and prion pathology in mice infected with RML scrapie. (A) Brain sections stained for $PrP^{Sc}$ (upper row: cortex and hippocampus, lower row: cerebellum) show that anle138b treatment reduces $PrP^{Sc}$ accumulation compared to DMSO-treated animals. (B) Quantification of $PrP^{Sc}$ levels in brain homogenates of prion-inoculated mice at indicated time points shows that $PrP^{Sc}$ accumulation in anle138b-treated mice is strongly reduced, even after start of treatment at a late stage in disease (120 dpi). (C) Histological quantification of apoptotic cells in the cerebellum in H&E stained brain slices shows that inhibition of $PrP^{Sc}$ accumulation results in inhibition of neuronal cell death. (D) Control mice treated with DMSO+peanut butter without compound show progressive weight loss. Treatment with anle138b from 80 dpi onwards prevents weight loss for ~100 days. Treatment from 120 dpi inhibits weight loss for ~70 days. Error bars in B and C indicate standard error (n=4 mice). The legend shown in figure B also applies to figures C and D.

Example 11: Influence of Daily Treatment with anle138b on PrPC Accumulation and Prion Pathology in Mice Infected with RML Scrapie C57BL/6 mice were inoculated intracerebrally (i.c.) with 30 μL of 1% brain homogenate (RML scrapie). Treatment was started at 80 days or 120 days post infection, respectively, with 5 mg compound per day applied orally mixed with DMSO+peanut butter (FIG. 10).

Brain sections stained for PrP$^{Sc}$ (FIG. 10A) show that anle138b treatment reduces PrP$^{Sc}$ accumulation compared to DMSO-treated animals. Quantification of PrP$^{Sc}$ levels in brain homogenates of prion-inoculated mice at different time points shows that PrP$^{Sc}$ accumulation in anle138b-treated mice is strongly reduced, even after start of treatment at a late stage in disease (120 dpi; FIG. 10B). Histological quantification of apoptotic cells in the cerebellum in H&E stained brain slices shows that inhibition of PrP$^{Sc}$ accumulation results in inhibition of neuronal cell death (FIG. 10C). Control mice treated with DMSO+peanut butter without compound show progressive weight loss (FIG. 10D). Treatment with anle138b from 80 dpi onwards prevents weight loss for ~100 days. Treatment from 120 dpi inhibits weight loss for ~70 days.

These experimental findings indicate that compound treatment inhibits PrP$^{Sc}$ accumulation, neuronal cell death and progression of clinical signs of disease, even when treatment is started late after obvious signs of disease are present.

Example 12: Comparison of Different Treatment Protocols

C57BL/6 mice were inoculated intracerebrally (i.c.) with 30 μL of 1% brain homogenate (RML scrapie). Treatment with anle138b at different times and schedules (as indicated in the figure legend of FIG. 11) significantly prolonged the survival times after challenge with RML scrapie (p<0.01). Mean survival times are expressed in days±standard deviation.

Figure 11:
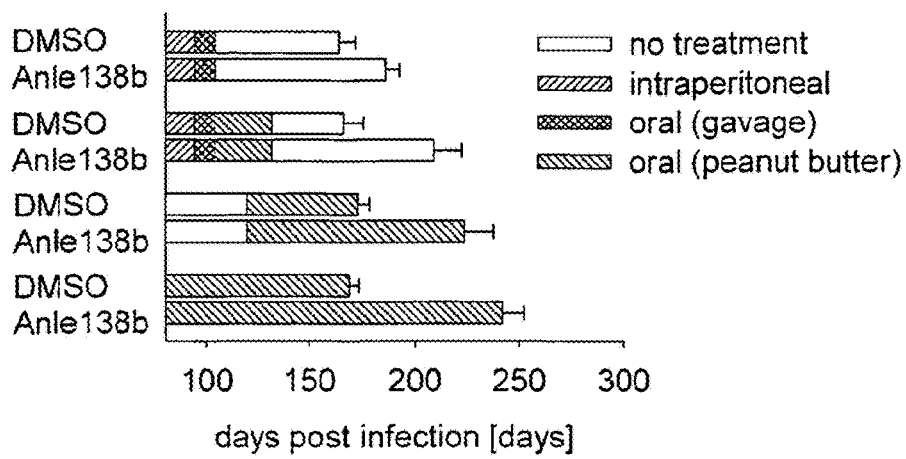
FIG. 11: Comparison of different treatment protocols. Treatment with anle138b at different times and schedules as indicated in the figure significantly prolonged the survival times after challenge with RML scrapie (p<0.01). Mean survival times are expressed in days±standard deviation.

As shown in FIG. 11, these experimental findings indicate that i) compound treatment is effective also after oral application of compound, ii) treatment is also effective when started late at the clinical stage of disease, and iii) that longer treatment results in longer survival.

Figure 12:
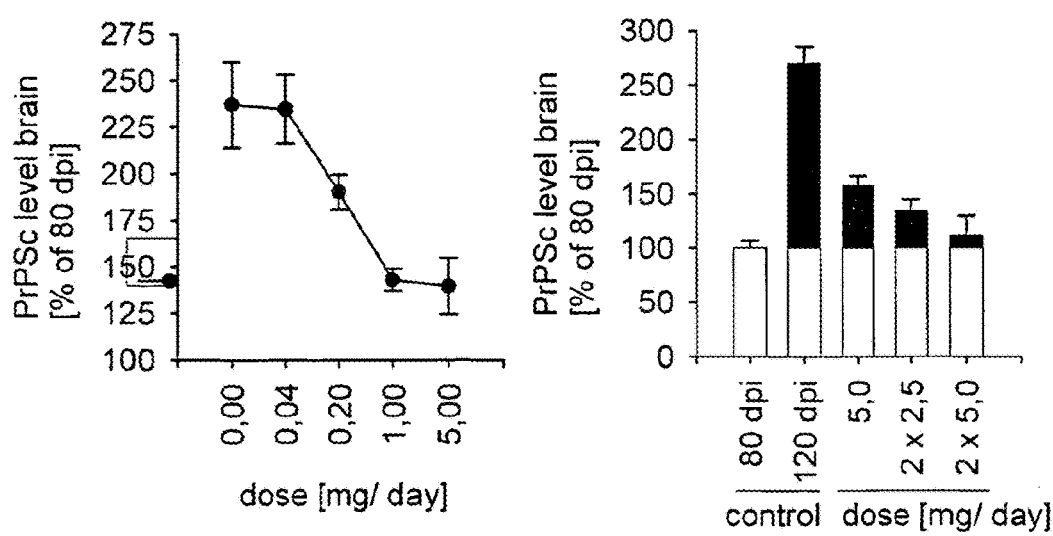
FIG. 12: Dose-dependent effect of anle138b administration on PrPSc levels in brain. C57BL/6 mice were inoculated intracerebrally (i.c.) with 30 µL of 1% brain homogenate (RML scrapie). Treatment was started at 80 days post infection with different amounts of anle138b (as shown in the Figure) applied orally mixed with DMSO+peanut butter. At 120 days post infection, animals were sacrificed and the amount of $PrP^{Sc}$ in the brain was quantified in comparison to animals sacrificed at day 80 post infection. Error bars indicate standard error (n=4 mice).

Example 13: Dose-Dependent Effect of anle138b Administration on PrPSc Levels in Brain C57BL/6 mice were inoculated intracerebrally (i.c.) with 30 μL of 1% brain homogenate (RML scrapie). Treatment was started at 80 days post infection with different amounts of anle138b (as shown in FIG. 12) applied orally mixed with DMSO+peanut butter. At 120 days post infection, animals were sacrificed and the amount of $PrP^{Sc}$ in the brain was quantified in comparison to animals sacrificed at day 80 post infection.

The data provided in FIG. 12 shown that anle138b reduced $PrP^{Sc}$ accumulation in brain in a dose-dependent manner.

Example 14

Figure 13:
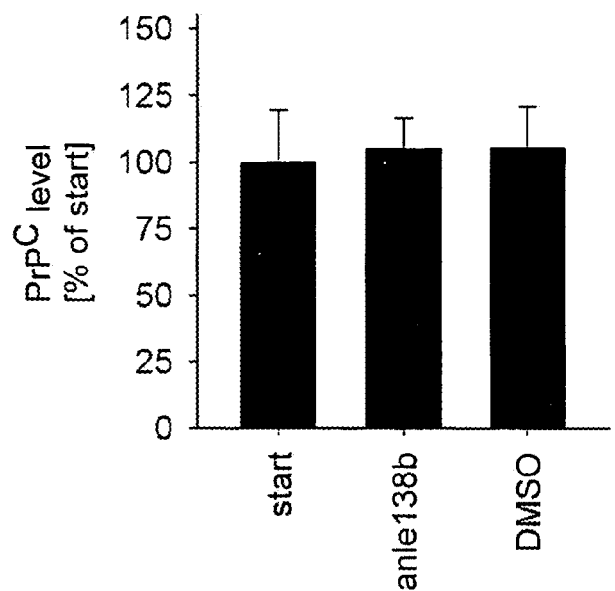
FIG. 13: Quantification of $PrP^c$ by immunoblotting of brain tissue from non-infected mice treated with 1 mg per day anle138b mixed with DMSO+peanut butter for 1 week. Each bar represents four mice in each group.

Quantification of $PrP^c$ by immunoblotting of brain tissue from non-infected mice treated with 1 mg per day anle138b mixed with DMSO+peanut butter for 1 week. As shown in FIG. 13, no reduction in $PrP^c$ level was observed in mice treated with anle138b when compared to control mice.

These experimental findings indicate that the therapeutic effect in scrapie-infected mice is not due to a reduced expression of $PrP^c$ but to an inhibition of the formation of pathological aggregated protein species.

Example 15: Pharmacokinetic Analysis of anle138b

Figure 14:
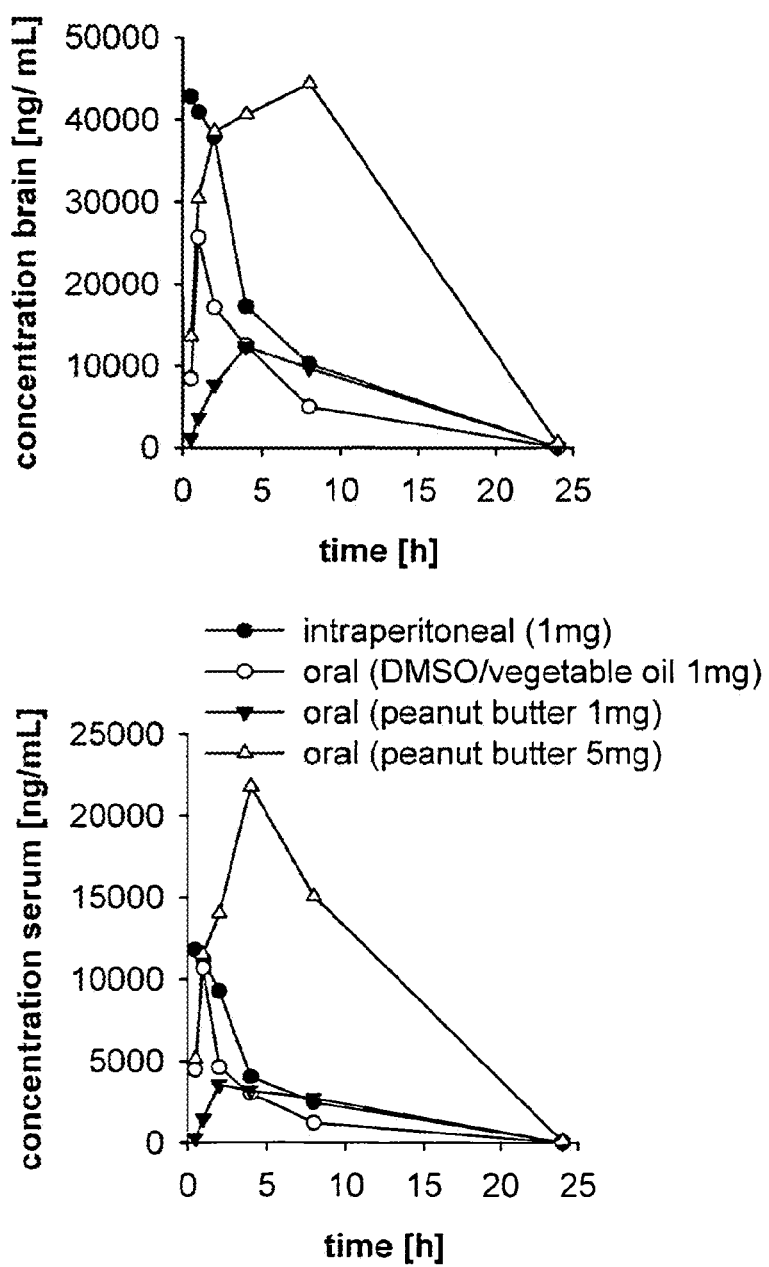
FIG. 14: Pharmacokinetic analysis of Anle138b. A single dose of anle138b was applied to non-infected C57BL/6 mice as indicated. At different time points after application, the amount of compound in the brain and serum was measured for 2 animals per time point and experimental group by LC-MS.

A single dose of anle138b was applied to non-infected C57BL/6 mice as indicated in FIG. 14.

At different time points after application, the amount of compound in the brain and serum was measured for 2 animals per time point and experimental group by LC-MS.

These experimental findings indicate that there is a good oral bioavailability and good brain penetration. anle138c was detected in the blood of the mice, so that it is assumed to be a metabolite of anle138b.

Figure 15:
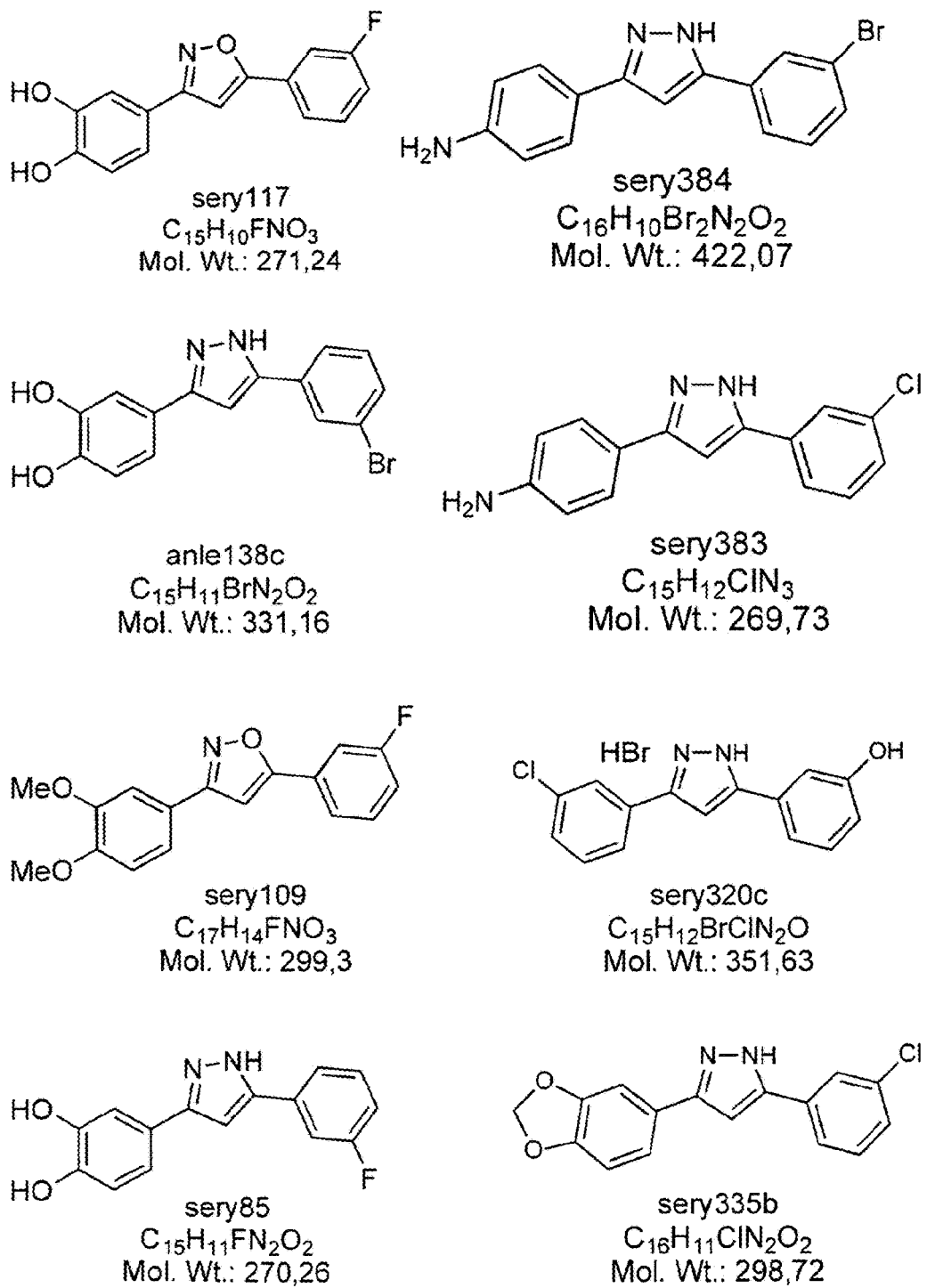
FIG. 15: Inhibition of the formation of α-synuclein aggregates by different compounds. The structures of the compounds tested in Table 2 are shown.
Figure 15:
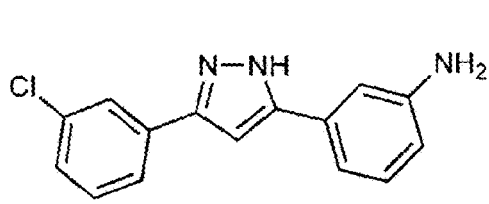
Figure 15:
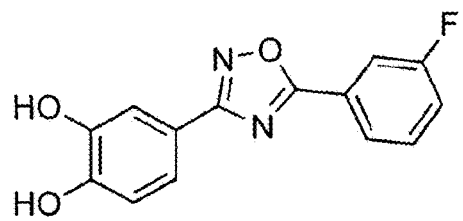
Figure 15:
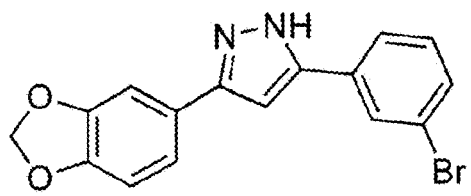
Figure 15:
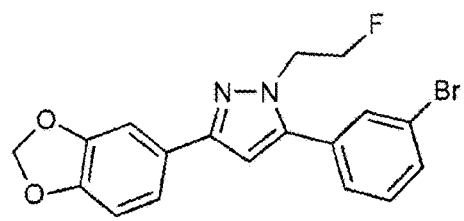
Figure 15:
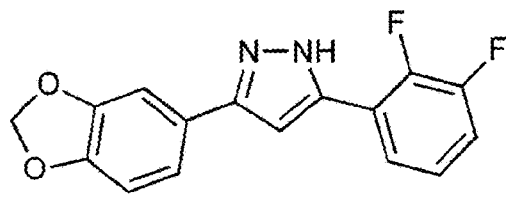
Figure 15:
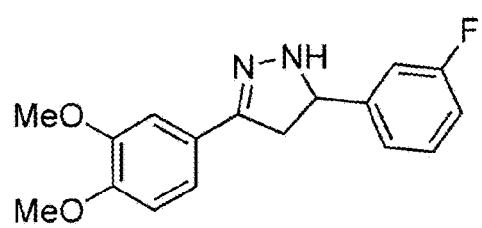
Figure 15:
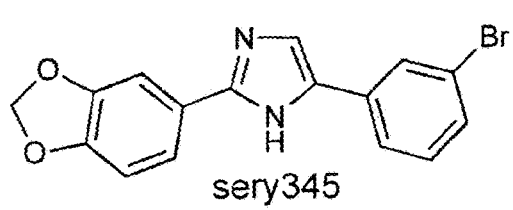
Figure 15:
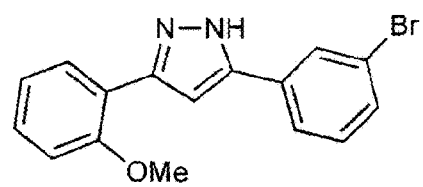
Figure 15:
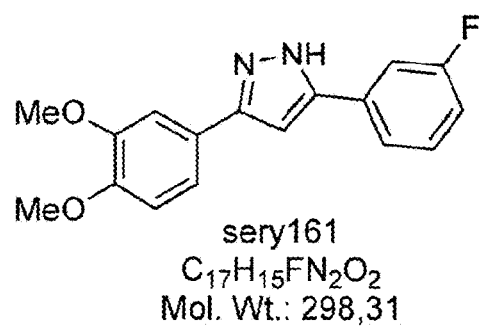
Figure 15:
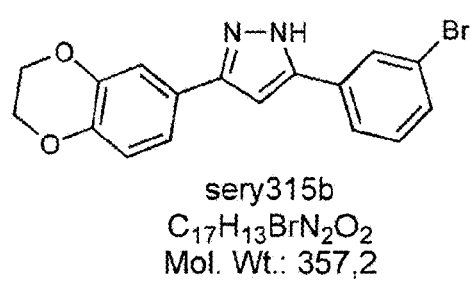
Figure 15:
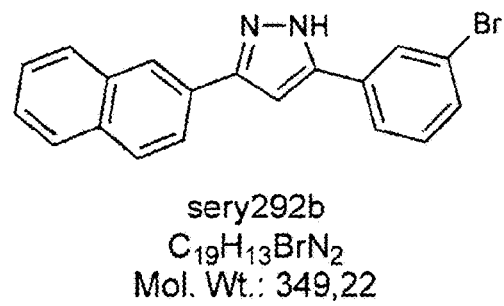
Figure 15:
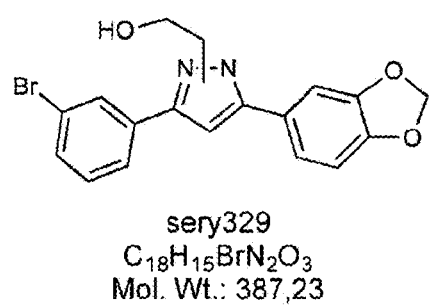
Figure 15:
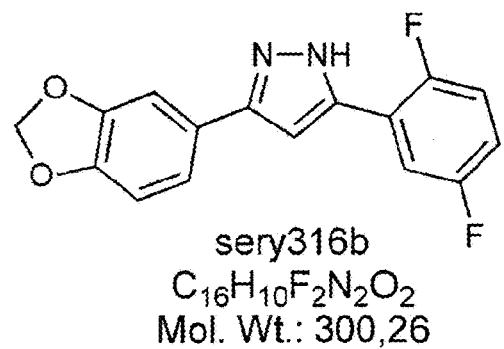

Example 16: Inhibition of the Formation of α-Synuclein Aggregates by Different Compounds Aggregation of α-synuclein was induced by DMSO and 10 μM $FeCl_3$ and analyzed by confocal single molecule spectroscopy as described in Kostka et al. (J Biol Chem (2008) 283: 10992-11003). The effect of different compounds added at a concentration of 10 μM on the effect of the formation of intermediate II oligomers was studied in comparison to controls without compound, as shown in Table 2. The structures of the respective compounds are shown in FIG. 15.

TABLE 2

Inhibition of the formation of α-synuclein aggregates by different compounds.

| Compound | Intermediate II | Compound | Intermediate II | Compound | Intermediate II |
|---|---|---|---|---|---|
| anle138c | <5% | sery85 | <25% | sery145 | <50% |
| sery117 | <5% | sery335b | <25% | sery345 | <50% |
| sery384 | <5% | sery275b | <25% | sery256b | <50% |
| sery383 | <5% | sery140 | <25% | sery161 | <75% |
| sery109 | <5% | anle138b | <25% | sery315b | <75% |
| sery320c | <5% | sery363b | <25% | sery316b | <75% |
|  |  | sery319 | <25% | sery292b | <75% |
|  |  |  |  | sery329 | <75% |

These experimental findings indicate that these compounds inhibit the formation of toxic α-synuclein aggregates, which indicates that these structurally related compounds have the potential to be used for the treatment of protein diseases with protein aggregation, and in particular also for the treatment of diseases in which aggregation of α-synuclein can be observed.

Example 16: Effect of Compounds in an In Vivo Mouse Model of Parkinson's Disease Experimental evidence suggests that in experimental models of Parkinson's disease using mitochondrial toxins such as MPTP and rotenone at suitable concentrations, formation of aggregated α-synuclein can be observed and contributes to neuronal cell death. Mice were treated with MPTP (30 mg/kg bodyweight daily) by intraperitoneal injection on days 1-5 to induce degeneration of dopaminergic neurons in the substantia nigra. Animals (3-10 per experimental group) were treated with different compounds or vehicle (250 mg/kg bodyweight daily, oral application (tube feeding of compound in 12.5 μl DMSO mixed with 487.5 μl olive oil) on days 0-12). Loss of neurons compared to non-MPTP-treated mice (Control, defined as 0% cell death) and MPTP-treated mice that were treated with vehicle only (DMSO; defined as 100% cell death) was quantified on day 12. For quantification of tyrosine hydroxylase (TH)-positive substantia nigra pars compacta (SNpc) cells, 50 μm sections were immunostained with an anti-TH-antibody. Every second section through the SNpc was analyzed using Stereo investigator software (MicroBrightfield, Colchester, Vt., USA). Immunostained cells were counted by the optical fractionator method using a 20× objective. Stereological counts were performed blindly by two independent investigators.

Figure 16:
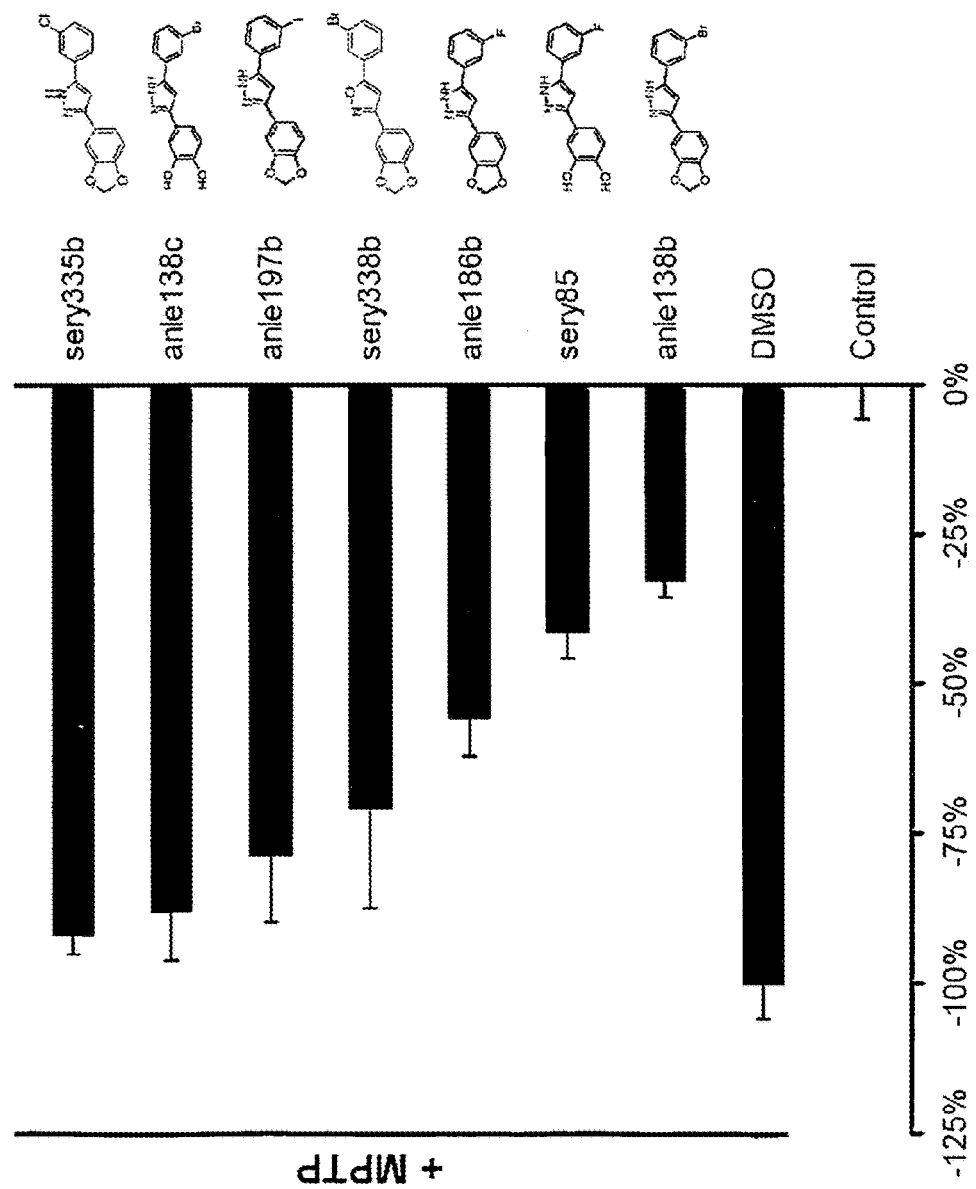
FIG. 16: Quantification of loss of neurons in MPTP-treated mice as compared to non-MPTP-treated mice as evaluated by determining tyrosine hydroxylase (TH)-positive substantia nigra pars compacta (SNpc) cells in 50 µm sections immunostained with an anti-TH-antibody. Every second section through the SNpc was analyzed using Stereo investigator software (MicroBrightfield, Colchester, Vt., USA). Immunostained cells were counted by the optical fractionator method using a 20× objective. Stereological counts were performed blindly by two independent investigators.

The experimental findings as shown in FIG. 16 indicate that the tested compounds reduce cell death in an in vivo model of Parkinson's disease.

Example 17: Effect of anle138c on ABeta Aggregation

Abeta40 with 50 μM concentration was incubated in the following condition for 30 hours: 50 mM sodium phosphate, 50 mM sodium chloride, 0.01% sodium azide, pH 7.4, 37° C., stirred with fine magnetic bars, with or without 50 μM anle138c. DMSO was added to the control sample at the equal concentration of the test sample. DMSO concentration was 2% (vol/vol), and the stock solution of anle138C was 3 mM. The peptide solution was centrifuged at 16000 g for 15 minutes before DLS experiments.

While the largest peak in the monomeric Abeta40 corresponded with a hydrodynamic radius of about 1.5 nm and an oligomer peak at approximately 30 nm (top panel), Abeta40 aggregate state in the presence of anle138C (middle panel) showed an oligomer peak around 20 nm in addition to the monomer peak. Bottom panel displays the size distribution for the amyloid fibrillar state of Abeta40, measured after centrifuging the sample. ABeta aggregation was analysed by dynamic light scattering. DLS measurements were performed as duplicate at 25° C., on a DynaPro Titan (Wyatt Technology Corp., CA) instrument, with a laser of 827.08 nm. The scattering angle was 900. DLS measurement consisted of twenty 10-s long acquisitions. Refractive index (RI) of the solution was set at 1.333 at 589 nm and 20° C., and the RI at the studied wavelength was obtained through Cauchy equation, with a coefficient of 3119 $nm^2$.

The viscosity was 1.019 cp at 20° C. and the temperature-dependent variations were calculated by an aqueous model. The size distribution was determined by a constrained regularization method.

Figure 17:
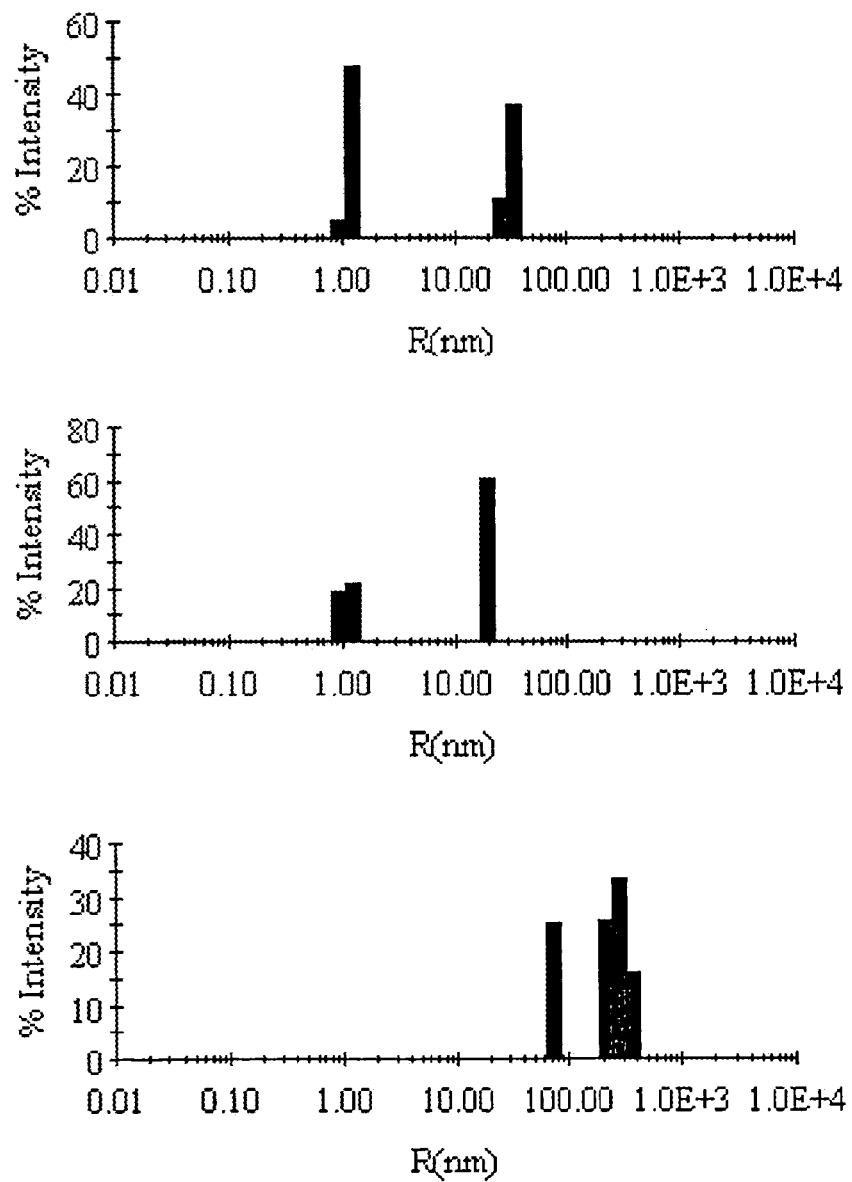
FIG. 17: Effect of anle138C on ABeta aggregation. ABeta aggregation was analysed by dynamic light scattering. Monomeric and oligomeric Abeta40 in the absence (top panel) and presence of anle138C (middle panel). The bottom panel displays the size distribution for the amyloid fibrillar state of Abeta40, measured after centrifuging the sample.

These experimental findings as shown in FIG. 17 indicate that anle138c inhibits formation of large Abeta40 oligomers, which indicates that anle138c and related compounds can also interfere with ABeta aggregation, which can be used for therapeutic and diagnostic purposes in diseases such as Alzheimer's disease that are neuropathologically characterized by deposition of aggregated ABeta.

An alternative embodiment of the compounds of the present invention is summarized in the following items. These compounds can be used in an identical manner to the above mentioned compounds of the invention.

1. A compound represented by formula (I)

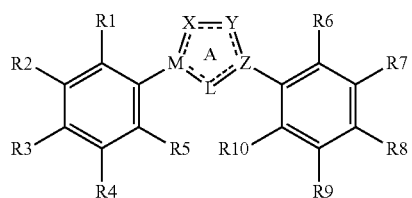

wherein

X, Y and L are independently nondirectionally selected from —C(R11)(R12)-, —C(R13)=, —N(R14)-, —N=, —$N^+$(R17)=, —O— and —S—;

M and Z are independently nondirectionally selected from

- - - - represents an optional double bond;

R1 to R15 or R17 or R18 are independently selected from hydrogen, halo, cyano, hydroxy, nitro, amino, azido, sulfonyl, thio, phosphonyl, carboxy, carbonylamido, alkyl, alkenyl, alkynyl, alkoxy, acyl, acyloxy, acylamino, a carbocyclic group, carbocyclooxy, carbocycloalkyl, carbocycloalkenyl, aryl, arylalkyl, arylalkenyl, arylalkynyl, aryloxy, arylalkoxy, a heterocyclic group, heterocyclooxy, heterocycloalkyl, a heteroaryl group, heteroaryloxy, heteroarylalkyl, heteroarylalkenyl and heteroarylalkoxy, or two adjacent groups may be linked to form a bridging group having 1 to 6 carbon atoms, wherein one or two carbon atoms may be replaced by —O—, —S— or —N(R')—, wherein R' is selected from H and $C_{1-4}$alkyl; each of which is optionally substituted;

as well as a prodrug, ester, solvate or salt thereof;

with the proviso that the compound is not one of the following compounds (a), (b) or (c)

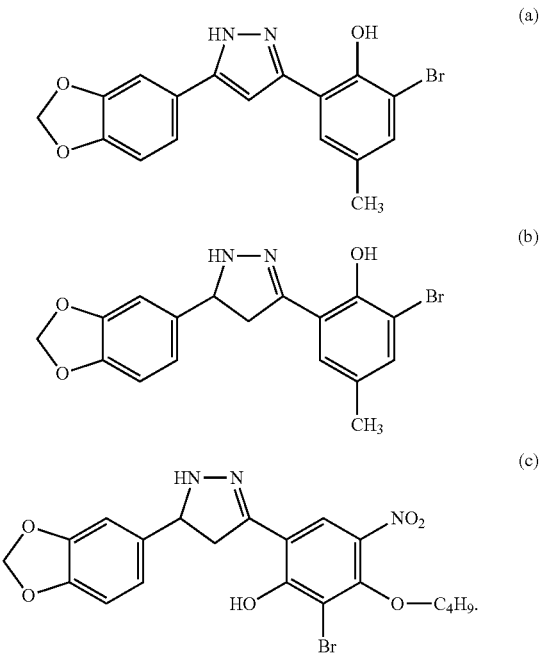

2. The compound according to item 1, wherein ring A is directionally selected from the following structures:

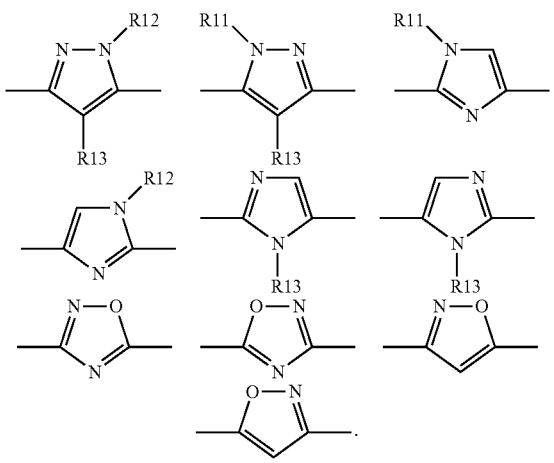

3. The compound according to item 1 or 2, wherein R7 is halo, cyano, hydroxy, nitro, azido, alkoxy, thio, alkylthio, amino, haloalkoxy, alkyl or haloalkyl.

4. The compound according to any one of items 1 to 3, wherein R2 and R3 are each independently selected from hydroxy and C1-6 alkoxy; or R2 and R3 together form a structure —O—$(CH_2)$n-O—, wherein n is 1 to 3, preferably n is 1.

5. A compound represented by formula (I)

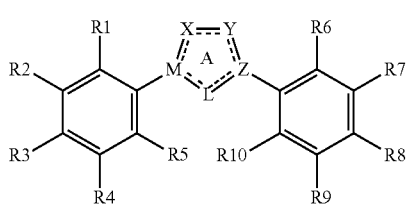

wherein
X, Y and L are independently nondirectionally selected from —C(R11)(R12)-, —C(R13)=, —N(R14)-, —N=, —N⁺(R17)=, —O— and —S—;
M and Z are independently nondirectionally selected from —C(R15)-, —C=,

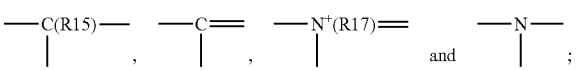

- - - - represents an optional double bond;
R1 to R15 or R17 or R18 are independently selected from hydrogen, halo, cyano, hydroxy, nitro, amino, azido, sulfonyl, thio, phosphonyl, carboxy, carbonylamido, alkyl, alkenyl, alkynyl, alkoxy, acyl, acyloxy, acylamino, a carbocyclic group, carbocyclooxy, carbocycloalkyl, carbocycloalkenyl, aryl, arylalkyl, arylalkenyl, arylalkynyl, aryloxy, arylalkoxy, a heterocyclic group, heterocyclooxy, heterocycloalkyl, a heteroaryl group, heteroaryloxy, heteroarylalkyl, heteroarylalkenyl and heteroarylalkoxy, or two adjacent groups may be linked to form a bridging group having 1 to 6 carbon atoms, wherein one or two carbon atoms may be replaced by —O—, —S— or —N(R')—, wherein R' is selected from H and $C_{1-4}$alkyl; each of which is optionally substituted;
as well as a prodrug, ester, solvate or salt thereof;
for the use in the treatment or prevention of a disease linked to protein aggregation and/or a neurodegenerative disease.

6. Use of a compound represented by formula (I) as defined in item 5 for the preparation of a pharmaceutical composition for treating or preventing a disease linked to protein aggregation and/or a neurodegenerative disease.

7. A method of treating or preventing a disease linked to protein aggregation and/or a neurodegenerative disease comprising administering a therapeutically effective amount of a compound represented by formula (I) as defined in item 5 is applied to a patient in need thereof.

8. A method of identifying a compound for inhibiting aggregation of a protein involved in a disease linked to protein aggregation and/or a neurodegenerative disease, comprising the steps of:
bringing into contact a labeled monomeric protein and a differently labeled aggregate of said protein in the (1) presence and/or (2) absence of a candidate inhibitor of aggregation which is a compound as defined in item 5;
determining the amount of co-localized labels representing the extent of binding of the monomeric protein to the aggregate of said protein; and
comparing the result obtained in the presence and absence of said compound,
wherein a decrease of co-localized labels in the presence of said compound is indicative of the compound's ability to inhibit aggregation of said protein.

9. The method of item 8, wherein said labels are fluorescent labels.

10. The method of item 8 or 9, wherein said labels are attached to an antibody or a fragment of an antibody specifically bound to said protein.

11. The method of item 10, wherein said antibody or fragment of an antibody is capable of discriminating between the aggregated and monomeric protein.

12. The method of any one of items 8 to 11, wherein the amount of co-localized labels is determined by using the method of "scanning for intensely fluorescent targets (SIFT)" or Fluorescence resonance energy transfer (FRET) or high resolution confocal imaging.

13. The method of any one of items 8 to 12, wherein said monomeric and aggregated proteins are selected from the group consisting of prion protein, Amyloid precursor protein (APP), alpha-synuclein, superoxide dismutase, tau, immunoglobulin, Amyloid-A, transthyretin, Beta2-microglobulin, cystatin C, Apolipoproteine A1, TDP-43, Islet amyloid polypeptide, ANF, gelsolin, insulin, lysozyme, fibrinogen, huntingtin and ataxin and other proteins with a Poly-Q stretch, and fragments or derivates of said proteins.

14. The method of item 13, wherein said monomeric protein is prion protein and said aggregated protein is PrPsc.

15. The method of item 13, wherein said monomeric protein is alpha-Synuclein and said aggregated protein is selected from the group consisting of oligomers or protofibrils or fibrils of alpha-Synuclein.

16. A method of selecting compounds with in vivo efficacy in the treatment or prevention of a disease linked to protein aggregation and/or a neurodegenerative disease, comprising:
(a) administering a candidate compound as defined in item 5 to a cell culture or a non-human animal having the aggregatable isoform of the protein as defined in any of items 13 to 15;
(b) quantifying the amount of observable aggregates; and
(c) identifying and selecting a compound which is capable of reducing aggregates or the formation of aggregates of said protein or of increasing the survival time of the cell culture or non-human animal.

17. Use of a compound as defined in item 5 for inhibiting protein aggregation in vitro, in an animal or ex vivo.

18. A pharmaceutical or diagnostic composition comprising a compound as defined in item 5 and optionally a pharmaceutically acceptable carrier.

19. The compound according to any one of items 1 or 5 or the use of item 6 or the method according to any one of items 7 to 16 or the use according to item 17 or the composition according to item 18, wherein said compound is selected from the group consisting of:

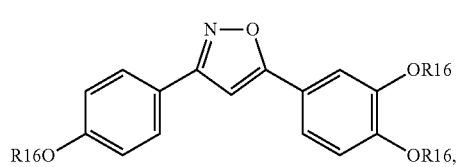

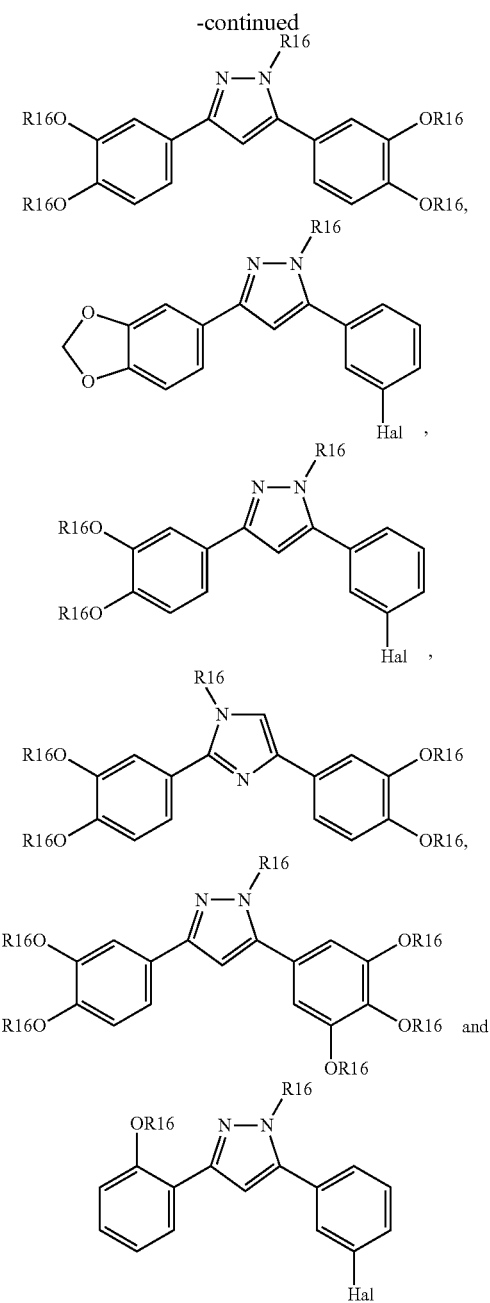

wherein each R16 is independently selected from H and C$_{1-4}$alkyl; or two adjacent R16 groups may be linked to form a bridging group having 1 to 3 carbon atoms; as well as a prodrug, ester, solvate or salt thereof.

20. The method according to any one of items 16 or 19 or the use according to any one of items 17 or 19, the diagnostic composition according to any one of items 18 or 19, wherein said compound is detectably labeled.

21. The method according to any one of items 16, 19 to 20 or the use according to any one of items 17, 19 to 20, wherein two or more of said compounds are used simultaneously.

22. The compound according to any one of items 5 or 19, wherein said disease linked to protein aggregation is characterized by the presence of an aggregated form of at least one protein or a fragment or derivative thereof, wherein the protein is selected from the group consisting of prion protein, Amyloid precursor protein (APP), alpha-synuclein, superoxide dismutase, tau, immunoglobulin, Amyloid-A, transthyretin, Beta2-microglobulin, cystatin C, Apolipoproteine A1, TDP-43, Islet amyloid polypeptide, ANF, gelsolin, insulin, lysozyme, fibrinogen, huntingtin and ataxin and other proteins with a Poly-Q stretch.

23. The compound according to any one of items 5, 19 or 22, wherein said disease is selected from the group consisting of Alzheimer's disease, prion disease, Parkinson's disease, multiple system atrophy, Diffuse Lewy body disease, frontotemporal dementia, amyotrophic lateral sclerosis, Huntington disease's, spinocerebellar ataxias and other Poly-Q diseases, hereditary cerebral amyloid angiopathy, familial amyloid polyneuropathy, primary systemic amyloidosis (AL amyloidosis), reactive systemic amyloidosis (AA amyloidosis), type II diabetes, injection-localized amyloidosis, beta-2 microglobulin amyloidosis, hereditary non-neuropathic amyloidosis, and Finnish hereditary systemic amyloidosis.

24. The compound of item 23, wherein said prion disease is selected from Creutzfeldt-Jakob disease, variant Creutzfeldt-Jakob disease, genetic human prion disease, Bovine Spongiform Encephalopathy (BSE) and Scrapie.

25. A kit comprising the compound as defined in any one of items 5 and 18 to 24 and, in addition, an antibody or antibody fragment specifically binding to said compound; and/or monomeric or aggregated protein as defined in item 13 to 15; and/or monomeric or aggregated protein as defined in item 13 to 15 optionally complexed with said compound; and instructions for use, in one or more containers.

The term "halo" as used herein refers to a halogen atom selected from fluorine, chlorine, bromine and iodine, preferably bromine.

The term "carboxy" as used herein refers to the group —COOH.

The term "alkyl" and "alk" refers to a straight or branched chain alkane (hydrocarbon) radical containing from 1 to 12 carbon atoms, preferably 1 to 6 carbon atoms, more preferably 1 to 4 carbon atoms. Exemplary such groups include, but are not limited to, methyl, ethyl, propyl, isopropyl, n-butyl, t-butyl, isobutyl, pentyl, hexyl, isohexyl, heptyl.

The term "alkenyl" refers to a straight or branched chain hydrocarbon radical containing from 2 to 12 carbon atoms, preferably 2 to 6 carbon atoms, and at least one carbon-carbon double bond. Exemplary such groups include ethenyl or allyl.

The term "alkynyl" refers to a straight or branched chain hydrocarbon radical containing from 2 to 12 carbon atoms, preferably 2 to 6 carbon atoms, and at least one carbon to carbon triple bond. Exemplary such groups include ethynyl.

The term "alkoxy" refers to an alkyl group as described above bonded through an oxygen linkage (—O—).

An "acyl group" in accordance with the present invention is a functional group in which an alkyl, aryl, heterocyclic or heteroaryl is attached to a carbonyl group. Examples of acyl groups are formyl group; C$_{1-6}$ alkyl-carbonyl group such as acetyl group, propionyl group, butyryl group and pivaloyl group; C$_{2-6}$ alkenyl-carbonyl group such as ethenoyl group, propenoyl group and butenoyl group; aroyl group such as benzoyl group, and the like, preferably acetyl group.

The term "acyloxy" as used herein refers to an acyl group which is bound to —O—. Similarly, "acylamino" is an acyl group which is bound to —N(R")— wherein R" is H or C1-6 alkyl.

The term "carbocyclic group" refers to a fully saturated cyclic hydrocarbon group containing from 1 to 4 rings, preferably 1 ring, and 3 to 8 carbons per ring. Exemplary such groups include cyclopropyl, cyclobutyl, cyclopentyl, cyclohexyl, etc.

The term "carbocyclooxy" refers to an carbocyclic group as described above bonded through an oxygen linkage (—O—).

The term "carbocycloalkyl" refers to an alkyl group substituted with an carbocyclic group, wherein the carbocyclic and the alkyl are defined as outlined above.

The term "carbocycloalkenyl" refers to an alkenyl group substituted with an carbocyclic group, wherein the carbocyclic group and the alkenyl are defined as outlined above.

The term "aryl" refers to cyclic, aromatic hydrocarbon groups which have 6 to 20, preferably 6 to 10 backbone carbon atoms and have 1 to 3 aromatic rings, especially monocyclic or bicyclic groups such as phenyl, biphenyl or naphthyl. Where containing two or more aromatic rings (bicyclic, etc.), the aromatic rings of the aryl group may be joined at a single point (e. g. biphenyl), or be fused (e. g. naphthyl, phenanthrenyl and the like).

The term "arylalkyl" refers to an alkyl group substituted with an aryl group, wherein the aryl and the alkyl are defined as outlined above.

The term "arylalkenyl" refers to an alkenyl group substituted with an aryl group, wherein the aryl and the alkenyl are defined as outlined above.

The term "arylalkynyl" refers to an alkynyl group substituted with an aryl group, wherein the aryl and the alkynyl are defined as outlined above.

The term "aryloxy" refers to an aryl group as described above bonded through an oxygen linkage (—O—), for example, phenoxy group, anthryloxy group, biphenylyloxy group and the like, preferably phenoxy group.

The term "arylalkoxy" refers to an alkoxy group substituted with an aryl group, wherein the aryl and the alkoxy are defined as outlined above.

The term "heterocyclic group" refers to fully saturated, or partially or fully unsaturated, cyclic groups (for example, 3 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include ethylene oxide, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamolpholinyl, thiamorpholinyl sulfoxide, thiamoipholinyl sulfone, 1,3-dioxolane and tetrahydro-1, 1-dioxothienyl, and the like. Exemplary bicyclic heterocyclic groups include indolyl, isoindolyl, benzothiazolyl, benzodioxolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo [2,3-c]pyridinyl, furo [3,2-b]pyridinyl] or furo [2,3-b]pyridinyl), dihydrobenzodioxinyl, dihydrodioxidobenzothiophenyl, dihydroisoindolyl, dihydroindolyl, dihydroquinolinyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, dibenzofuranyl, acridinyl, phenanthridinyl, xanthenyl and the like.

The term "heterocyclooxy" refers to an heterocyclic group as described above bonded through an oxygen linkage (—O—).

The term "heterocycloalkyl" refers to an alkyl group substituted with an heterocyclic group, wherein the heterocyclic and the alkyl are defined as outlined above.

The term "heteroaryl" as used herein refers to a 5- to 6-membered aromatic ring, which may contain, as heteroatoms, oxygen, sulphur and/or nitrogen and to which a further aromatic ring may be fused. Non-limiting examples without limitation of heteroaryl groups are benzofuranyl, furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, quinolinyl, isoquinolinyl, purinyl, carbazolyl, benzoxazolyl, benzamidazolyl, indolyl, isoindolyl, pyrazinyl, diazinyl, pyrazine, triazinyltriazine, tetrazinyl, tetrazolyl, benzothiophenyl, benzopyridyl and benzimidazolyl.

The term "heteroaryloxy" refers to an hetaryl group as described above bonded through an oxygen linkage (—O—).

The terms "heteroarylalkyl", "heteroarylalkenyl" and "heteroarylalkynyl" refer to groups wherein an alkyl, alkenyl or alkynyl group is substituted with an heteroaryl group, wherein the heteroaryl and the alkyl, alkenyl and alkynyl are defined as outlined above.

The term "heteroarylalkoxy" refers to an alkoxy group substituted with an heteroaryl group, wherein the heteroaryl and the alkoxy are defined as outlined above.

"Substituted", as used herein, refers to a group substituted with one or more substituents, preferably 1 to 4 substituents, at any available point of attachment. Exemplary substituents include but are not limited to one or more of the following groups: alkyl, alkoxy, halo, hydroxy, carboxy (i.e., —COOH), alkoxycarbonyl, alkylcarbonyloxy, amino (i.e., —NH$_2$), thiol and nitro.

In a preferred alternative embodiment R1 is selected from the group consisting of hydrogen and alkyl, more preferably hydrogen.

In a preferred alternative embodiment R2 is selected from the group consisting of hydroxy and alkoxy.

In a preferred alternative embodiment R3 is selected from the group consisting of hydroxy and alkoxy.

In a further preferred alternative embodiment R2 and R3 are linked together and form a structure —O(CH$_2$)$_n$O—, wherein n is 1 to 3, preferably n is 1.

In a preferred alternative embodiment R4 is selected from the group consisting of hydrogen, hydroxy and alkoxy, more preferably hydrogen.

In a preferred alternative embodiment R5 is selected from the group consisting of hydrogen and alkyl, more preferably hydrogen.

In a preferred alternative embodiment R6 is selected from the group consisting of hydrogen and alkyl, more preferably hydrogen.

In a preferred alternative embodiment R7 is selected from the group consisting of hydrogen, halo, cyano, nitro, hydroxy and alkoxy, more preferably R7 is hydrogen, halo, hydroxy or alkoxy, even more preferably R7 is halo.

In a preferred alternative embodiment R8 is selected from the group consisting of hydrogen, hydroxy and alkoxy.

In a preferred alternative embodiment R9 is selected from the group consisting of hydrogen, halo, hydroxy and alkoxy.

In a preferred alternative embodiment R10 is selected from the group consisting of hydrogen, and alkyl, more preferably hydrogen.

In a preferred alternative embodiment R11 is selected from the group consisting of hydrogen, and alkyl.

In a preferred alternative embodiment R12 is selected from the group consisting of hydrogen, and alkyl.

In a preferred alternative embodiment R13 is selected from the group consisting of hydrogen, and alkyl.

In a preferred alternative embodiment R14 is selected from the group consisting of hydrogen, and alkyl.

In a preferred alternative embodiment R15 is selected from the group consisting of hydrogen, and alkyl.

In another preferred alternative embodiment of the compound of the invention, R7 is halo, cyano, hydroxyl or nitro, azido, alkoxy, thio, alkylthio, amino, haloalkoxy, alkyl or haloalkyl.

In a preferred alternative embodiment, R7 is halo, cyano, hydroxyl or nitro, more preferably halo.

In a further preferred alternative embodiment, R2 and R3 are each independently selected from hydroxy and $C_{1-6}$ alkoxy; or R2 and R3 together form a structure —O—$(CH_2)_n$—O—, wherein n is 1 to 3, preferably n is 1.

In a preferred alternative embodiment the compound is selected from the group consisting of wherein each R16 is independently selected from H and $C_{1-4}$alkyl; or two adjacent R16 groups may be linked to form a bridging group having 1 to 3 carbon atoms; as well as prodrugs, esters, solvates or salts thereof.

In a more preferred alternative embodiment the compound is selected from the group consisting of:

3-(4-Hydroxyphenyl)-5-(3,4-dihydroxyphenyl)isoxazole 3,5-Bis(3,4-dimethoxyphenyl)pyrazole 5-(3-Bromophenyl)-3-(3,4-methylenedioxyphenyl)pyrazole

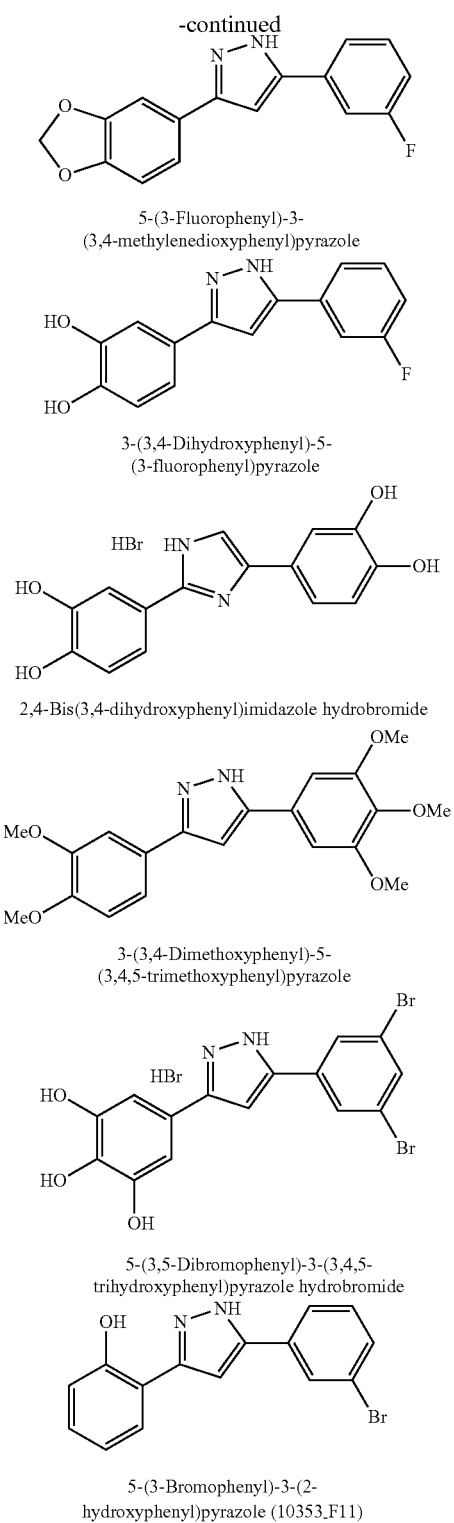

The compounds of the alternative embodiment can be detectably labeled.

REFERENCES

Anselme J. P. Convenient and practical preparation of dibenzoylmethane. *J. Org. Chem.* 32, 3716-3716 (1967)

Bach, S. et al. Isolation of drugs active against mammalian prions using a yeast-based screening assay. *Nat Biotechnol* 21, 1075-1081 (2003).

Bieschke, J. et al. Ultrasensitive detection of pathological prion protein aggregates by dual-color scanning for intensely fluorescent targets. 97, 5468-5473 (2000).

Borchelt, D. R., Taraboulos, A. & Prusiner, S. B. Evidence for synthesis of scrapie prion proteins in the endocytic pathway. *J. Biol. Chem.* 267, 16188-16199 (1992).

Borgelt, C. & Berthold, M. R. in IEEE International Conference on Data Mining (ICDM) 51-58 (IEEE Press, Piscataway, N.J., USA 2002, Maebashi, Japan; 2002).

Butler, D. A. et al. Scrapie-infected murine neuroblastoma cells produce protease-resistant prion proteins. *J. Virol.* 62, 1558-1564 (1988).

Caughey, B. & Raymond, G. J. The scrapie-associated form of PrP is made from a cell surface precursor that is both protease- and phospholipase-sensitive. *J. Biol. Chem.* 266, 18217-18223 (1991).

Caughey, W. S., Raymond, L. D., Horiuchi, M. & Caughey, B. Inhibition of protease-resistant prion protein formation by porphyrins and phthalocyanines. *P Natl Acad Sci* USA 95, 12117-12122 (1998).

Chabry, J., Caughey, B. & Chesebro, B. Specific inhibition of in vitro formation of protease-resistant prion protein by synthetic peptides. *J Biol Chem* 273, 13203-13207 (1998).

Chalquest R. R. Materials and methods for killing nematodes and nematode eggs. PCT Int. Appl. W O 2001054508 A1 (2001)

Chimenti F. et al. Synthesis and selective inhibitory activity of 1-acetyl-3,5-diphenyl-4,5-dihydro-(1H)-pyrazole derivatives against monoamine oxidase. *J. Med. Chem.* 47, 2071-2074 (2004)

Daude N, Marella M, Chabry J. Specific inhibition of pathological prion protein accumulation by small interfering RNAs. J Cell Sci. 2003; 116(Pt 13):2775-9.

Demaimay, R., Chesebro, B. & Caughey, B. Inhibition of formation of protease-resistant prion protein by Trypan Blue, Sirius Red and other Congo Red analogs. 277-283 (2000).

Enari M, Flechsig E, Weissmann C. Scrapie prion protein accumulation by scrapie-infected neuroblastoma cells abrogated by exposure to a prion protein antibody. Proc Natl Acad Sci USA. 2001; 98(16):9295-9.

Giese, A., Bieschke, J., Eigen, M. & Kretzschmar, H. A. Putting prions into focus: application of single molecule detection to the diagnosis of prion diseases. *Arch Virol*, 161-171 (2000).

Giese, A. & Kretzschmar, H. A. Prion-induced neuronal damage—The mechanisms of neuronal destruction in the subacute spongiform encephalopathies. *Curr Top Microbiol* 253, 203-217 (2001).

Gilch, S. et al. Intracellular re-routing of prion protein prevents propagation of PrPSc and delays onset of prion diseases. *EMBO J* 20, 3957-3966 (2001).

Goedert, M., 2001, Alpha-synuclein and neurodegenerative diseases. Nat Rev Neurosci. 2(7):492-501

Hall M. J. et al. A modular synthesis of unsymmetrical tetraarylazadipyrromethenes. *J. Org. Chem.* 70, 5571-5578 (2005)

Harris R. L. N. et al. Synthetic plant growth regulators. The synthesis of C-o-Carboxyphenyl derivatives of some five-membered heterocycles. *Aust. J. Chem.* 30, 2225-2240 (1977)

Hauser C. R. et al. N- and C-benzoylation of p-aminoacetophenone with methyl benzoate by sodium amide. Synthesis of β-diketones having p-acylamino and p-hydroxy groups. *J. Org. Chem.* 22, 909-912 (1957)

Horiuchi, M., Priola, S. A., Chabry, J. & Caughey, B. Interactions between heterologous forms of prion protein: Binding, inhibition of conversion, and species barriers. *P Natl Acad Sci USA* 97, 5836-5841 (2000).

Ihlenfeldt, W. D., Takahashi Y., Abe H. & S., S. Computation and Management of Chemical Properties in CACTVS: An Extensible Networked Approach toward Modularity and Compatibility. *Journal of Chemical Information and Computer Sciences* 34, 109-116 (1994).

Kiachopoulos, S., Heske, J., Tatzelt, J. & Winklhofer, K. F. Misfolding of the prion protein at the plasma membrane induces endocytosis, intracellular retention and degradation. *Traffic* in press (2004).

Kocisko, D. A. et al. New inhibitors of scrapie-associated prion protein formation in a library of 2,000 drugs and natural products (vol 77, pg 10288, 2003). *J Virol* 78, 3202-3202 (2004).

Kocisko, D. A. et al. New inhibitors of scrapie-associated prion protein formation in a library of 2,000 drugs and natural products. *J Virol* 77, 10288-10294 (2003).

Koltermann, A., Kettling, U., Bieschke, J., Winkler, T. & Eigen, M. Rapid assay processing by integration of dual-color fluorescence cross-correlation spectroscopy: High throughput screening for enzyme activity. *P Natl Acad Sci USA* 95, 1421-1426 (1998).

Korbonits D. et al. Ring transformation of 3-(2-aminoaryl)-1,2,4-oxadiazoles into 3-acylaminoindazoles; extension of the Boulton-Katritzky scheme. *J. Chem. Soc. Perkin. Trans.* 1 759-766 (1982)

Kostka M, Högen T, Danzer K M, Levin J, Habeck M, Wirth A, Wagner R, Glabe C G, Finger S, Heinzelmann U, Garidel P, Duan W, Ross C A, Kretzschmar H, Giese A. Single particle characterization of iron-induced pore-forming alpha-synucleinoligomers J Biol Chem. 2008, 283(16):10992-1003.

Li B. et al. An optimized process for formation of 2,4-disubstituted imidazoles from condensation of amidines and α-haloketones. *Org. Process Res. Dev.* 6, 682-683 (2002)

Liemann, S. and R. Glockshuber (1999). "Influence of amino acid substitutions related to inherited human prion diseases on the thermodynamic stability of the cellular prion protein." *Biochemistry* 38(11): 3258-67.

Llewelyn, C. A. et al. Possible transmission of variant Creutzfeldt-Jakob disease by blood transfusion. *Lancet* 363, 417-421 (2004).

Mallucci, G. et al. Depleting neuronal PrP in prion infection prevents disease and reverses spongiosis. *Science* 302, 871-874 (2003).

Munishkina L A, Phelan C, Uversky V N, Fink A L., 2003, Conformational behavior and aggregation of alpha-synuclein in organic solvents: modeling the effects of membranes. Biochemistry 42(9):2720-30.

Nam, N. H. et al. Synthesis and cytotoxicity of 2,5-Dihydroxychalcones and related compounds. *Arch. Pharm. Res.* 27, 581-588 (2004).

Perrier, V. et al. Mimicking dominant negative inhibition of prion replication through structure-based drug design. *P Natl Acad Sci USA* 97, 6073-6078 (2000).

Post, K. et al. Rapid acquisition of beta-sheet structure in the prion protein prior to multimer formation. *Biological Chemistry* 379, 1307-1317 (1998).

Prusiner, S. B. Prions. *P Natl Acad Sci USA* 95, 13363-13383 (1998).

Rudyk, H. et al. Screening Congo Red and its analogues for their ability to prevent the formation of PrP-res in scrapie-infected cells. *J Gen Virol* 81, 1155-1164. (2000).

Safar J, Wille H, Itri V, Groth D, Serban H, Torchia M, Cohen F E, Prusiner S B.: Eight prion strains have PrP(Sc) molecules with different conformations. Nat Med. 1998 October; 4(10):1157-65.

Schätzl, H. M. et al. A hypothalamic neuronal cell line persistently infected with scrapie prions exhibits apoptosis. *J. Virol.* 71, 8821-8831 (1997).

Schwille, P., Bieschke, J. & Oehlenschlager, F. Kinetic investigations by fluorescence correlation spectroscopy: The analytical and diagnostic potential of diffusion studies. *Biophys Chem* 66, 211-228 (1997).

Sethi S, Lipford G, Wagner H, Kretzschmar H. Postexposure prophylaxis against prion disease with a stimulator of innate immunity. Lancet. 2002; 360(9328):229-30

Soto, C. et al. Reversion of prion protein conformational changes by synthetic beta-sheet breaker peptides. *Lancet* 355, 192-197 (2000).

Tatzelt, J., Prusiner, S. B. & Welch, W. J. Chemical chaperones interfere with the formation of scrapie prion protein. *EMBO J* 15, 6363-6373 (1996).

Vanelle P. et al. Functional derivatives of 5-benzo[1,3]dioxol-5-yl-1-methyl-1H-imidazole-2-carbaldehyde and evaluation of leishmanicidal activity. *Eur. J. Med. Chem.* 35, 157-162 (2000).

Vorberg I, Buschmann A, Harmeyer S, Saalmuller A, Pfaff E, Groschup M H. A novel epitope for the specific detection of exogenous prion proteins in transgenic mice and transfected murine cell lines. Virology. 1999 Mar. 1; 255(1):26-31

White A R, Enever P, Tayebi M, Mushens R, Linehan J, Brandner S, Anstee D, Collinge J, Hawke S. Monoclonal antibodies inhibit prion replication and delay the development of prion disease. Nature. 2003; 422(6927):80-3.

Will, R. G. et al. A new variant of Creutzfeldt-Jakob disease in the U K. *Lancet* 347, 921-925 (1996). Bruce, M. E. et al. Transmissions to mice indicate that 'new variant' CJD is caused by the BSE agent. *Nature* 389, 498-501 (1997).

Winklhofer, K. F. & Tatzelt, J. Cationic lipopolyamines induce degradation of PrPSc in scrapie-infected mouse neuroblastoma cells. *Biol Chem* 381, 463-469 (2000).

Winklhofer, K. F., Hartl, F. U. & Tatzelt, J. A sensitive filter retention assay for the detection of PrPSc and the screening of anti-prion compounds. *FEBS Lett.* 503, 41-45 (2001).

The invention claimed is:

1. A method of treating a disease of protein aggregation in a subject comprising administering to a subject in need thereof a therapeutically effective amount of a compound represented by formula (E),

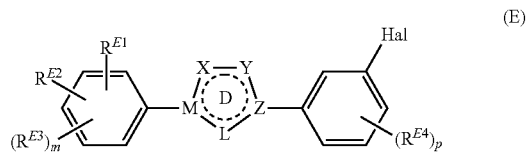

wherein
the ring D is directionally selected from the following structures:

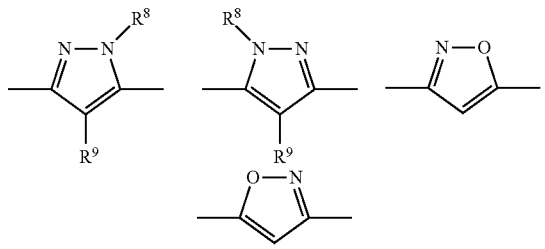

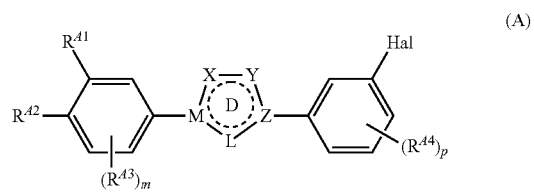

wherein $R^8$ and $R^9$ are independently selected from hydrogen; $C_{1-4}$ alkyl; —$C_{1-4}$ alkylene-halogen; —$C_{1-4}$ alkylene-OH; —$C_{1-4}$ alkylene-$C_{1-4}$ alkoxy; —C(O)—$C_{1-4}$ alkyl; and $C_{6-10}$ aryl, wherein the aryl ring can be optionally substituted by $C_{1-4}$ alkyl or halogen;

Hal is selected from F, Cl, Br, and I;

$R^{E5}$ and $R^{E6}$ are independently selected from hydrogen and $C_{1-6}$ alkyl;

$R^{E7}$ and $R^{E8}$ are independently H or F;

$R^{E9}$ and $R^{E10}$ are independently H or F;

n is 1 to 3;

$R^{E3}$ is a $C_{1-6}$ alkyl group or a $C_{5-10}$ aryl group;

m is 0 to 2;

$R^{E4}$ is a halogen atom, a $C_{1-6}$ alkyl group or a $C_{5-10}$ aryl group;

p is 0 to 2;

wherein (i) $R^{E1}$ and $R^{E2}$ are attached to adjacent carbon atoms and $R^{E1}$ and $R^{E2}$ together form a structure -T-($CR^{E7}R^{E8}$)$_n$—V—, wherein T is selected from $CR^{E9}R^{E10}$m NH and O and V is selected from $CR^{E9}R^{10}$, NH and O, as well as corresponding structures in which a double bond is present;

(ii) $R^E$ is —$NR^{E5}R^{E6}$ and is attached in para-position compared to the carbon atom which binds the phenyl ring to ring D and $R^{E2}$ is selected from hydrogen, halogen, hydroxy, $C_{1-6}$ alkoxy, and —$NR^{E5}R^{E6}$; or (iii) $R^{E1}$ and $R^{E2}$ are independently selected from $C_{1-6}$ alkoxy and hydroxy and are attached meta and para compared to the carbon atom which binds the phenyl ring to ring D;

as well as an ester, solvate or salt of the compound represented by formula (E); wherein the disease of protein aggregation is selected from the group consisting of scrapie, Parkinson's disease, Alzheimer's disease, Creutzfeldt-Jakob disease, multiple system atrophy, dementia with Lewy bodies, and type II diabetes.

2. The method according to claim 1, wherein the disease of protein aggregation is selected from the group consisting of Parkinson's disease, multiple system atrophy, and dementia with Lewy bodies.

3. The method according to claim 1, wherein the disease of protein aggregation is selected from the group consisting of Alzheimer's disease, Creutzfeldt-Jakob disease; and scrapie.

4. The method according to claim 1, wherein the disease of protein aggregation is type II diabetes.

5. The method of claim 1, wherein the compound represented by formula (E) is a compound represented by formula (A)

(A)

wherein $R^{A1}$ and $R^{A2}$ are each independently selected from hydrogen, halogen, hydroxy, $C_{1-6}$ alkoxy, and —$NR^{A5}R^{A6}$, with the proviso that at least one of $R^{A1}$ and $R^{A2}$ is hydroxy, $C_{1-6}$ alkoxy, or —$NR^{A5}R^{A6}$;

alternatively $R^{A1}$ and $R^{A2}$ can together form a structure -T-($CR^{E7}R^{E8}$)$_n$—V—;

$R^{A3}$ is a $C_{1-6}$ alkyl group or a $C_{5-10}$ aryl group;

$R^{A4}$ is a halogen atom, a $C_{1-6}$ alkyl group or a $C_{5-10}$ aryl group; and $R^{A5}$ and $R^{A6}$ are independently selected from hydrogen and $C_{1-6}$ alkyl;

as well as an ester, solvate or salt of the compound represented by formula (A).

6. The method of claim 1 wherein $R^8$ and $R^9$ are selected from hydrogen; $C_{1-4}$ alkyl; —$C_{1-4}$ alkylene-halogen; and $C_{6-10}$ aryl, wherein the aryl ring can be optionally substituted by $C_{1-4}$ alkyl or halogen.

7. The method of claim 1, wherein ring D is directionally selected from the following structures:

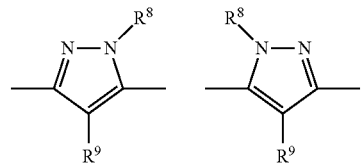

wherein $R^9$ is H.

8. The method of claim 1, wherein the compound is selected from the group consisting of:

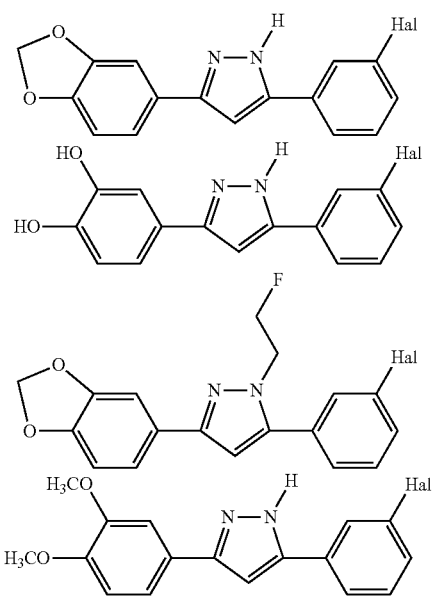

-continued

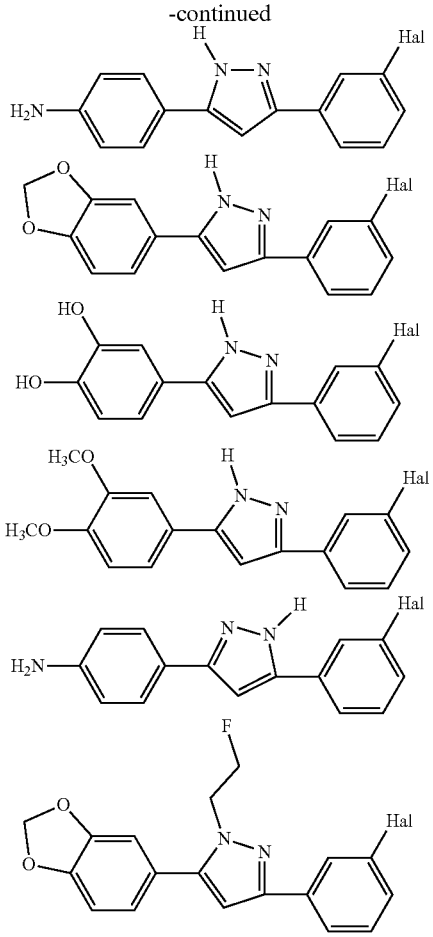

wherein Hal is Cl or Br;
as well as an ester, solvate or salt of these compounds.

9. The method of claim 1, wherein the compound is

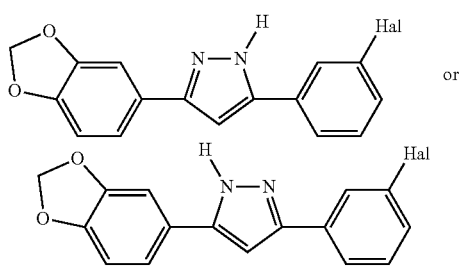

wherein Hal is Cl or Br;
or an ester, solvate or salt thereof.

10. The method of claim 1, wherein the compound is

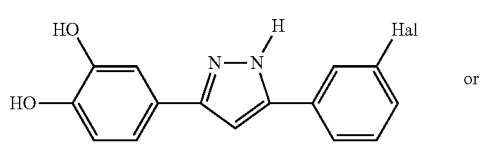

or

-continued

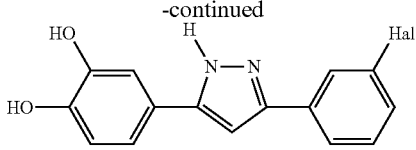

wherein Hal is Cl or Br;
or an ester, solvate or salt thereof.

11. The method of claim 1, wherein the compound is

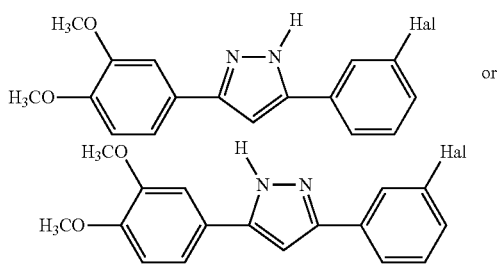

or wherein Hal is Cl or Br;
or an ester, solvate or salt thereof.

12. The method of claim 1, wherein the compound is

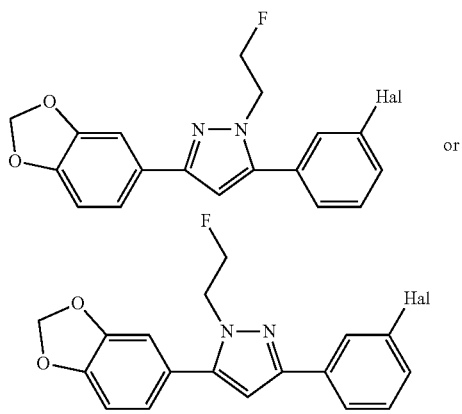

wherein Hal is Cl or Br;
or an ester, solvate or salt thereof.

13. The method of claim 1, wherein the compound is

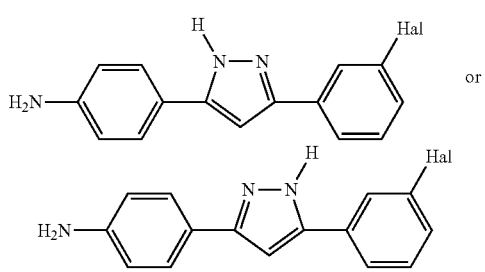

wherein Hal is Cl or Br;
or an ester, solvate or salt thereof.

* * * * *